(12) United States Patent
Bornhop et al.

(10) Patent No.: US 10,627,396 B2
(45) Date of Patent: Apr. 21, 2020

(54) FREE-SOLUTION RESPONSE FUNCTION INTERFEROMETRY

(71) Applicant: VANDERBILT UNIVERSITY, Nashville, TN (US)

(72) Inventors: Darryl J. Bornhop, Nashville, TN (US); Amanda Kussrow, Nashville, TN (US); Michael Kammer, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 0 days.

(21) Appl. No.: 16/073,630

(22) PCT Filed: Jan. 27, 2017

(86) PCT No.: PCT/US2017/015296
§ 371 (c)(1),
(2) Date: Jul. 27, 2018

(87) PCT Pub. No.: WO2017/132483
PCT Pub. Date: Aug. 3, 2017

(65) Prior Publication Data
US 2019/0033301 A1    Jan. 31, 2019

Related U.S. Application Data

(60) Provisional application No. 62/288,926, filed on Jan. 29, 2016.

(51) Int. Cl.
*G01N 21/45* (2006.01)
*G01N 33/536* (2006.01)
(Continued)

(52) U.S. Cl.
CPC .......... *G01N 33/536* (2013.01); *G01N 21/19* (2013.01); *G01N 21/41* (2013.01); *G01N 21/4133* (2013.01); *G01N 21/45* (2013.01); *G01N 2201/0221* (2013.01)

(58) Field of Classification Search
CPC ........ G01N 21/00; G01N 21/19; G01N 21/25; G01N 21/41; G01N 21/4133; G01N 21/45
See application file for complete search history.

(56) References Cited

U.S. PATENT DOCUMENTS 3,567,113 A    3/1971    Stansell et al.
3,687,808 A    8/1972    Merigan, Jr.
(Continued)

FOREIGN PATENT DOCUMENTS

CA    2584824 A1    5/2006
EP    0721016 A2    7/1996
(Continued)

OTHER PUBLICATIONS

Ababou et al., Survey of the year 2005: literature on applications of isothermal titration calorimetry. J Mol Recognit. 2007; 20(1):4-14.
(Continued)

*Primary Examiner* — Jonathan M Hansen
(74) *Attorney, Agent, or Firm* — Ballard Spahr LLP

(57) ABSTRACT

Disclosed are methods for the free solution measurement of molecular interactions by refractive index sensing other than backscattering interferometry. The disclosed methods can have very low detection limits and/or very low sample volume requirements. Also disclosed are various biosensor applications of the disclosed techniques. This abstract is intended as a scanning tool for purposes of searching in the particular art and is not intended to be limiting of the present invention.

26 Claims, 33 Drawing Sheets

(51) Int. Cl.
*G01N 21/19* (2006.01)
*G01N 21/41* (2006.01)

(56) References Cited

U.S. PATENT DOCUMENTS

| | | |
|---|---|---|
| 4,093,759 A | 6/1978 | Otsuki et al. |
| 4,265,554 A | 5/1981 | Clancy et al. |
| 4,268,554 A | 5/1981 | Gras |
| 4,443,106 A | 4/1984 | Yasuda et al. |
| 4,469,863 A | 9/1984 | Ts'o et al. |
| 4,476,301 A | 10/1984 | Imbach et al. |
| 4,587,044 A | 5/1986 | Miller et al. |
| 4,605,735 A | 8/1986 | Miyoshi et al. |
| 4,660,974 A | 4/1987 | Machler et al. |
| 4,667,025 A | 5/1987 | Miyoshi et al. |
| 4,683,195 A | 7/1987 | Mullis et al. |
| 4,683,202 A | 7/1987 | Mullis |
| 4,699,951 A | 10/1987 | Allenson et al. |
| 4,762,779 A | 8/1988 | Snitman |
| 4,789,737 A | 12/1988 | Miyoshi et al. |
| 4,824,941 A | 4/1989 | Gordon et al. |
| 4,828,979 A | 5/1989 | Klevan et al. |
| 4,835,263 A | 5/1989 | Nguyen et al. |
| 4,845,205 A | 7/1989 | Huynh Dinh et al. |
| 4,876,335 A | 10/1989 | Yamane et al. |
| 4,895,431 A | 1/1990 | Tsujiuchi et al. |
| 4,904,582 A | 2/1990 | Tullis |
| 4,908,112 A | 3/1990 | Pace |
| 4,948,882 A | 8/1990 | Ruth |
| 4,950,074 A | 8/1990 | Fabricius et al. |
| 4,958,013 A | 9/1990 | Letsinger |
| 4,976,154 A | 12/1990 | Schneider et al. |
| 4,981,957 A | 1/1991 | Lebleu et al. |
| 4,990,925 A | 2/1991 | Edelsohn et al. |
| 5,023,243 A | 6/1991 | Tullis |
| 5,034,506 A | 7/1991 | Summerton et al. |
| 5,073,024 A | 12/1991 | Valette et al. |
| 5,082,830 A | 1/1992 | Brakel et al. |
| 5,108,179 A | 4/1992 | Myers |
| 5,109,124 A | 4/1992 | Ramachandran et al. |
| 5,112,963 A | 5/1992 | Pieles et al. |
| 5,118,800 A | 6/1992 | Smith et al. |
| 5,118,802 A | 6/1992 | Smith et al. |
| 5,120,131 A | 6/1992 | Lukosz |
| 5,125,740 A | 6/1992 | Sato et al. |
| 5,130,302 A | 7/1992 | Spielvogel et al. |
| 5,134,066 A | 7/1992 | Rogers et al. |
| 5,138,045 A | 8/1992 | Cook et al. |
| 5,165,005 A | 11/1992 | Klainer et al. |
| 5,166,315 A | 11/1992 | Summerton et al. |
| 5,173,747 A | 12/1992 | Boiarski et al. |
| 5,175,273 A | 12/1992 | Bischofberger et al. |
| 5,177,196 A | 1/1993 | Meyer, Jr. et al. |
| 5,185,444 A | 2/1993 | Summerton et al. |
| 5,188,897 A | 2/1993 | Suhadolnik et al. |
| 5,214,134 A | 5/1993 | Weis et al. |
| 5,214,136 A | 5/1993 | Lin et al. |
| 5,215,883 A | 6/1993 | Chu |
| 5,216,141 A | 6/1993 | Benner |
| 5,218,105 A | 6/1993 | Cook et al. |
| 5,235,033 A | 8/1993 | Summerton et al. |
| 5,245,022 A | 9/1993 | Weis et al. |
| 5,254,469 A | 10/1993 | Warren, III et al. |
| 5,258,506 A | 11/1993 | Urdea et al. |
| 5,262,536 A | 11/1993 | Hobbs, Jr. |
| 5,264,423 A | 11/1993 | Cohen et al. |
| 5,264,562 A | 11/1993 | Matteucci |
| 5,264,564 A | 11/1993 | Matteucci |
| 5,268,305 A | 12/1993 | Ribi et al. |
| 5,272,250 A | 12/1993 | Spielvogel et al. |
| 5,273,633 A | 12/1993 | Wang |
| 5,276,019 A | 1/1994 | Cohen et al. |
| 5,278,302 A | 1/1994 | Caruthers et al. |
| 5,286,717 A | 2/1994 | Cohen et al. |
| 5,292,873 A | 3/1994 | Rokita et al. |
| 5,304,487 A | 4/1994 | Wilding et al. |
| 5,305,071 A | 4/1994 | Wyatt |
| 5,309,330 A | 5/1994 | Pillers et al. |
| 5,317,098 A | 5/1994 | Shizuya et al. |
| 5,319,080 A | 6/1994 | Leumann |
| 5,321,131 A | 6/1994 | Agrawal et al. |
| 5,325,170 A | 6/1994 | Bornhop |
| 5,350,697 A | 9/1994 | Swope et al. |
| 5,351,678 A | 10/1994 | Clayton et al. |
| 5,359,044 A | 10/1994 | Cook et al. |
| 5,367,066 A | 11/1994 | Urdea et al. |
| 5,371,241 A | 12/1994 | Brush |
| 5,377,008 A | 12/1994 | Ridgway et al. |
| 5,391,723 A | 2/1995 | Priest |
| 5,393,878 A | 2/1995 | Leumann |
| 5,399,676 A | 3/1995 | Froehler |
| 5,405,938 A | 4/1995 | Summerton et al. |
| 5,405,939 A | 4/1995 | Suhadolnik et al. |
| 5,414,077 A | 5/1995 | Lin et al. |
| 5,416,203 A | 5/1995 | Letsinger |
| 5,426,505 A | 6/1995 | Geiser et al. |
| 5,432,272 A | 7/1995 | Benner |
| 5,434,257 A | 7/1995 | Matteucci et al. |
| 5,446,137 A | 8/1995 | Maag et al. |
| 5,451,463 A | 9/1995 | Nelson et al. |
| 5,453,496 A | 9/1995 | Caruthers et al. |
| 5,455,233 A | 10/1995 | Spielvogel et al. |
| 5,456,245 A | 10/1995 | Bornhop et al. |
| 5,456,885 A | 10/1995 | Coleman et al. |
| 5,457,187 A | 10/1995 | Gmeiner et al. |
| 5,459,255 A | 10/1995 | Cook et al. |
| 5,466,677 A | 11/1995 | Baxter et al. |
| 5,470,967 A | 11/1995 | Huie et al. |
| 5,476,925 A | 12/1995 | Letsinger et al. |
| 5,479,257 A | 12/1995 | Hashimoto |
| 5,484,908 A | 1/1996 | Froehler et al. |
| 5,485,277 A | 1/1996 | Foster |
| 5,485,312 A | 1/1996 | Homer et al. |
| 5,486,603 A | 1/1996 | Buhr |
| 5,489,677 A | 2/1996 | Sanghvi et al. |
| 5,502,177 A | 3/1996 | Matteucci et al. |
| 5,502,561 A | 3/1996 | Hutchins et al. |
| 5,510,475 A | 4/1996 | Agrawal et al. |
| 5,512,439 A | 4/1996 | Hornes et al. |
| 5,512,667 A | 4/1996 | Reed et al. |
| 5,514,785 A | 5/1996 | Van Ness et al. |
| 5,519,126 A | 5/1996 | Hecht |
| 5,519,134 A | 5/1996 | Acevedo et al. |
| 5,525,465 A | 6/1996 | Haralambidis et al. |
| 5,525,711 A | 6/1996 | Hawkins et al. |
| 5,536,821 A | 7/1996 | Agrawal et al. |
| 5,539,082 A | 7/1996 | Nielsen et al. |
| 5,541,306 A | 7/1996 | Agrawal et al. |
| 5,541,307 A | 7/1996 | Cook et al. |
| 5,541,313 A | 7/1996 | Ruth |
| 5,545,730 A | 8/1996 | Urdea et al. |
| 5,550,111 A | 8/1996 | Suhadolnik et al. |
| 5,552,538 A | 9/1996 | Urdea et al. |
| 5,552,540 A | 9/1996 | Haralambidis |
| 5,556,852 A | 9/1996 | Nakamura et al. |
| 5,561,225 A | 10/1996 | Maddry et al. |
| 5,563,253 A | 10/1996 | Agrawal et al. |
| 5,565,552 A | 10/1996 | Magda et al. |
| 5,567,810 A | 10/1996 | Weis et al. |
| 5,567,811 A | 10/1996 | Misiura et al. |
| 5,571,799 A | 11/1996 | Tkachuk et al. |
| 5,574,142 A | 11/1996 | Meyer, Jr. et al. |
| 5,576,427 A | 11/1996 | Cook et al. |
| 5,578,717 A | 11/1996 | Urdea et al. |
| 5,578,718 A | 11/1996 | Cook et al. |
| 5,578,832 A | 11/1996 | Trulson et al. |
| 5,580,731 A | 12/1996 | Chang et al. |
| 5,585,481 A | 12/1996 | Arnold, Jr. et al. |
| 5,587,361 A | 12/1996 | Cook et al. |
| 5,587,371 A | 12/1996 | Sessler et al. |
| 5,587,469 A | 12/1996 | Cook et al. |
| 5,591,584 A | 1/1997 | Chang et al. |
| 5,591,722 A | 1/1997 | Montgomery et al. |
| 5,593,839 A | 1/1997 | Hubbell et al. |

(56) References Cited

U.S. PATENT DOCUMENTS

| | | |
|---|---|---|
| 5,594,121 A | 1/1997 | Froehler et al. |
| 5,595,726 A | 1/1997 | Magda et al. |
| 5,596,086 A | 1/1997 | Matteucci et al. |
| 5,596,091 A | 1/1997 | Switzer |
| 5,597,696 A | 1/1997 | Linn et al. |
| 5,597,909 A | 1/1997 | Urdea et al. |
| 5,599,695 A | 2/1997 | Pease et al. |
| 5,599,923 A | 2/1997 | Sessler et al. |
| 5,599,928 A | 2/1997 | Hemmi et al. |
| 5,602,240 A | 2/1997 | De Mesmaeker et al. |
| 5,608,046 A | 3/1997 | Cook et al. |
| 5,610,289 A | 3/1997 | Cook et al. |
| 5,610,300 A | 3/1997 | Altmann et al. |
| 5,613,013 A | 3/1997 | Schuette |
| 5,614,617 A | 3/1997 | Cook et al. |
| 5,618,704 A | 4/1997 | Sanghvi et al. |
| 5,623,070 A | 4/1997 | Cook et al. |
| 5,625,050 A | 4/1997 | Beaton et al. |
| 5,627,053 A | 5/1997 | Usman et al. |
| 5,631,734 A | 5/1997 | Stern et al. |
| 5,633,312 A | 5/1997 | Kabeta et al. |
| 5,633,360 A | 5/1997 | Bischofberger et al. |
| 5,633,708 A | 5/1997 | Svendsen |
| 5,636,017 A | 6/1997 | Bruno et al. |
| 5,639,873 A | 6/1997 | Barascut et al. |
| 5,646,265 A | 7/1997 | McGee |
| 5,658,873 A | 8/1997 | Bertsch-Frank et al. |
| 5,659,318 A | 8/1997 | Madsen et al. |
| 5,663,312 A | 9/1997 | Chaturvedula |
| 5,663,790 A | 9/1997 | Ekstrom et al. |
| 5,670,633 A | 9/1997 | Cook et al. |
| 5,677,437 A | 10/1997 | Teng et al. |
| 5,677,439 A | 10/1997 | Weis et al. |
| 5,681,941 A | 10/1997 | Cook et al. |
| 5,688,941 A | 11/1997 | Cook et al. |
| 5,694,210 A | 12/1997 | Newell et al. |
| 5,698,518 A | 12/1997 | Carson et al. |
| 5,700,920 A | 12/1997 | Altmann et al. |
| 5,712,321 A | 1/1998 | Cantor et al. |
| 5,714,331 A | 2/1998 | Buchardt et al. |
| 5,719,262 A | 2/1998 | Buchardt et al. |
| 5,740,291 A | 4/1998 | De Lasa et al. |
| 5,770,029 A | 6/1998 | Nelson et al. |
| 5,781,304 A | 7/1998 | Kotidis et al. |
| 5,804,453 A | 9/1998 | Chen |
| 5,815,258 A | 9/1998 | Nakanishi |
| 5,817,462 A | 10/1998 | Garini et al. |
| 5,824,204 A | 10/1998 | Jerman |
| 5,841,914 A | 11/1998 | Shieh et al. |
| 5,846,708 A | 12/1998 | Hollis et al. |
| 5,852,495 A | 12/1998 | Parce |
| 5,867,266 A | 2/1999 | Craighead |
| 5,915,034 A | 6/1999 | Nakajima et al. |
| 5,922,594 A | 7/1999 | Löfås |
| 5,928,627 A | 7/1999 | Kiefer et al. |
| 5,932,474 A | 8/1999 | Tsien et al. |
| 5,953,439 A | 9/1999 | Ishihara et al. |
| 5,976,336 A | 11/1999 | Dubrow et al. |
| 5,995,645 A | 11/1999 | Soenksen et al. |
| 6,008,378 A | 12/1999 | Tsien et al. |
| 6,054,271 A | 4/2000 | Tsien et al. |
| 6,108,458 A | 8/2000 | Hart |
| 6,118,536 A * | 9/2000 | Sakamoto ............... G01N 21/19 356/364 |
| 6,123,798 A | 9/2000 | Gandhi et al. |
| 6,130,439 A | 10/2000 | Le Menn |
| 6,167,910 B1 | 1/2001 | Chow |
| 6,198,532 B1 | 3/2001 | Cabib et al. |
| 6,251,343 B1 | 6/2001 | Dubrow et al. |
| 6,321,791 B1 | 11/2001 | Chow |
| 6,322,683 B1 | 11/2001 | Wolk et al. |
| 6,381,025 B1 | 4/2002 | Bornhop et al. |
| 6,381,925 B2 | 5/2002 | Rejcek et al. |
| 6,451,569 B1 | 9/2002 | Tsien et al. |
| 6,480,282 B1 | 11/2002 | Chinowsky et al. |
| 6,493,090 B1 | 12/2002 | Lading et al. |
| 6,529,279 B2 | 3/2003 | de Groot et al. |
| 6,532,061 B2 | 3/2003 | Ortyn et al. |
| 6,533,914 B1 | 3/2003 | Liu |
| 6,559,947 B1 | 5/2003 | Turner |
| 6,576,430 B1 | 6/2003 | Hsieh et al. |
| 6,660,517 B1 | 12/2003 | Wilding et al. |
| 6,741,361 B2 | 5/2004 | Marron |
| 6,744,950 B2 | 6/2004 | Aleksoff |
| 6,760,103 B2 | 7/2004 | Shakespeare et al. |
| 6,798,509 B2 | 9/2004 | Sonehara et al. |
| 6,809,828 B2 | 10/2004 | Bornhop et al. |
| 6,962,690 B2 | 11/2005 | Kiefer et al. |
| 6,980,299 B1 | 12/2005 | de Boer |
| 7,011,948 B2 | 3/2006 | Chapman et al. |
| 7,045,171 B2 | 5/2006 | Bookbinder et al. |
| 7,130,060 B2 | 10/2006 | Bornhop et al. |
| 7,172,897 B2 | 2/2007 | Blackburn et al. |
| 7,173,986 B2 | 2/2007 | Wu |
| 7,202,076 B2 | 4/2007 | Cunningham et al. |
| 7,300,803 B2 | 11/2007 | Lin et al. |
| 7,835,013 B2 | 11/2010 | Jones et al. |
| 8,120,777 B2 | 2/2012 | Weinberger et al. |
| 8,134,707 B2 | 3/2012 | Bornhop et al. |
| 8,445,217 B2 | 5/2013 | Bornhop |
| 8,450,118 B2 | 5/2013 | Weinberger et al. |
| 8,673,827 B1 | 3/2014 | Hermes |
| 9,273,949 B2 | 3/2016 | Bornhop et al. |
| 9,562,853 B2 | 2/2017 | Bornhop et al. |
| 9,638,632 B2 | 5/2017 | Bornhop |
| 9,990,464 B1 * | 6/2018 | Quinn ............... G01N 35/1097 |
| 2001/0045358 A1 | 11/2001 | Kopf-Sill et al. |
| 2001/0050821 A1 | 12/2001 | Bickleder et al. |
| 2002/0002353 A1 | 1/2002 | Michal et al. |
| 2002/0022603 A1 | 2/2002 | Lichtenberger |
| 2002/0034580 A1 | 3/2002 | Yang et al. |
| 2002/0057432 A1 | 5/2002 | Ortyn et al. |
| 2002/0094528 A1 | 7/2002 | Salafsky |
| 2002/0128234 A1 | 9/2002 | Hubbell et al. |
| 2002/0135772 A1 | 9/2002 | Bornhop et al. |
| 2003/0020915 A1 | 1/2003 | Schueller et al. |
| 2003/0082516 A1 | 5/2003 | Straus |
| 2003/0087099 A1 | 5/2003 | Merrill et al. |
| 2003/0099598 A1 | 5/2003 | Kiefer et al. |
| 2003/0129579 A1 | 7/2003 | Bornhop et al. |
| 2003/0148922 A1 | 8/2003 | Knapp et al. |
| 2004/0058058 A1 | 3/2004 | Shchegolikhin et al. |
| 2004/0110276 A1 | 6/2004 | Amontov et al. |
| 2004/0115721 A1 | 6/2004 | Mao et al. |
| 2004/0218184 A1 | 11/2004 | Jorgenson et al. |
| 2004/0241765 A1 | 12/2004 | Zweig |
| 2005/0004348 A1 | 1/2005 | Miyamoto et al. |
| 2005/0014179 A1 | 1/2005 | Karlsson et al. |
| 2005/0019956 A1 | 1/2005 | Martin et al. |
| 2005/0083505 A1 | 4/2005 | Augustyn et al. |
| 2005/0106570 A1 | 5/2005 | Kataoka et al. |
| 2005/0175273 A1 | 8/2005 | Iida et al. |
| 2005/0190372 A1 | 9/2005 | Dogariu |
| 2005/0227374 A1 | 10/2005 | Cunningham |
| 2005/0244863 A1 | 11/2005 | Mir |
| 2005/0264819 A1 | 12/2005 | Arnz et al. |
| 2006/0012777 A1 | 1/2006 | Talbot et al. |
| 2006/0012800 A1 | 1/2006 | Bornhop et al. |
| 2006/0039004 A1 | 2/2006 | de Boer et al. |
| 2006/0147379 A1 | 7/2006 | Bornhop et al. |
| 2006/0183700 A1 | 8/2006 | Vater et al. |
| 2006/0256343 A1 | 11/2006 | Choma et al. |
| 2006/0263777 A1 | 11/2006 | Tong |
| 2006/0268260 A1 | 11/2006 | Liu et al. |
| 2006/0275179 A1 | 12/2006 | Viovy et al. |
| 2006/0275825 A1 | 12/2006 | Baird et al. |
| 2007/0012777 A1 | 1/2007 | Tsikos et al. |
| 2007/0030841 A1 | 2/2007 | Lee et al. |
| 2007/0048747 A1 | 3/2007 | Leslie et al. |
| 2007/0054339 A1 | 3/2007 | Lin et al. |
| 2007/0146888 A1 | 6/2007 | Schmidt et al. |
| 2007/0195321 A1 | 8/2007 | Soussaline et al. |
| 2008/0160187 A1 | 7/2008 | Murata et al. |
| 2008/0182239 A1 | 7/2008 | Mullinax et al. |

(56) References Cited

U.S. PATENT DOCUMENTS

| | | | |
|---|---|---|---|
| 2008/0186488 A1 | 8/2008 | Kiesel et al. | |
| 2008/0194723 A1 | 8/2008 | Hwang et al. | |
| 2008/0248502 A1 | 10/2008 | Yamaguchi et al. | |
| 2008/0259313 A1 | 10/2008 | Berndt | |
| 2009/0009759 A1 | 1/2009 | Backman et al. | |
| 2009/0103091 A1 | 4/2009 | Jones et al. | |
| 2009/0135421 A1 | 5/2009 | Oldham et al. | |
| 2009/0147264 A1* | 6/2009 | Lotze | C12Q 1/6825 356/477 |
| 2009/0155832 A1 | 6/2009 | Lo et al. | |
| 2009/0185190 A1 | 7/2009 | Weinberger et al. | |
| 2009/0325199 A1 | 12/2009 | Geddes | |
| 2010/0099203 A1 | 4/2010 | Chang et al. | |
| 2010/0184056 A1 | 7/2010 | Weinberger et al. | |
| 2010/0188665 A1 | 7/2010 | Dotson et al. | |
| 2010/0191482 A1 | 7/2010 | Hasson et al. | |
| 2010/0210029 A1* | 8/2010 | Meinhart | G01N 21/05 436/168 |
| 2011/0109907 A1 | 5/2011 | Meyers et al. | |
| 2011/0155927 A1 | 6/2011 | Mitchell et al. | |
| 2011/0157692 A1 | 6/2011 | Lin et al. | |
| 2012/0015376 A1* | 1/2012 | Bornhop | G01N 21/05 435/7.2 |
| 2012/0019834 A1 | 1/2012 | Bornhop | |
| 2012/0199742 A1 | 8/2012 | Wagner et al. | |
| 2013/0021608 A1 | 1/2013 | Bornhop et al. | |
| 2013/0040306 A1 | 2/2013 | Bornhop et al. | |
| 2013/0224886 A1 | 8/2013 | Iwasaki et al. | |
| 2013/0280715 A1 | 10/2013 | Bornhop et al. | |
| 2013/0301055 A1 | 11/2013 | Bornhop et al. | |
| 2013/0309661 A1 | 11/2013 | Bornhop | |
| 2014/0285803 A1* | 9/2014 | Alouini | G01N 21/19 356/364 |
| 2016/0000239 A1 | 1/2016 | Denby et al. | |

FOREIGN PATENT DOCUMENTS

| | | |
|---|---|---|
| EP | 0728520 A1 | 8/1996 |
| EP | 0785280 A2 | 7/1997 |
| EP | 0799797 A1 | 10/1997 |
| EP | 1210581 A1 | 6/2002 |
| EP | 1746385 A1 | 1/2007 |
| EP | 1805498 A2 | 7/2007 |
| EP | 2160590 A1 | 3/2010 |
| EP | 2386060 A2 | 11/2011 |
| EP | 17744954.3 | 8/2018 |
| FR | 2766922 A1 | 2/1999 |
| IL | 260837 | 7/2018 |
| WO | WO-90/05317 A1 | 5/1990 |
| WO | WO-95/22058 A1 | 8/1995 |
| WO | WO-95/25116 A1 | 9/1995 |
| WO | WO-97/02357 A1 | 1/1997 |
| WO | WO-97/027317 | 7/1997 |
| WO | WO-97/029212 A1 | 8/1997 |
| WO | WO-2001/014858 A1 | 3/2001 |
| WO | WO-2002/059579 A1 | 8/2002 |
| WO | WO-2004/023115 A1 | 3/2004 |
| WO | WO-2006/047408 A2 | 5/2006 |
| WO | WO-2007/002178 A2 | 1/2007 |
| WO | WO-2008/144496 A1 | 11/2008 |
| WO | WO-2009/039466 A1 | 3/2009 |
| WO | WO-2010/080710 A2 | 7/2010 |
| WO | WO-2010/129494 A2 | 11/2010 |
| WO | WO-2011/156713 A1 | 12/2011 |
| WO | WO-2012/051429 A1 | 4/2012 |
| WO | WO-2017/132483 | 8/2017 |

OTHER PUBLICATIONS

Abato P, "An enzymatic method for determining enantiomeric excess," *Journal of the American Chemical Society*, 123: 9206-7 (2001).

Abbas AK, et al., Cellular and Molecular Immunology (Saunders, Philadelphia, ed. Fifth, 2003).

Adams et al., The effect of hybridization-induced secondary structure alterations on RNA detection using backscattering interferometry. Nucleic Acid Res. 2013; 41(9):e103.

Adanyi, et al., "Development of immunosensor based on OWLS technique for determining Aflatoxin B1 and Ochratoxin A," Biosens Bioelectron 22:797-802 (2007).

Ahlert J, et al., The calicheamicin gene cluster and its iterative type I enediyne PKS. *Science*, 297:1173-6 (2002).

Alunni S, et al., Mechanisms of inhibition of phenylalanine ammonia-lyase by phenol inhibitors and phenol/glycine synergistic inhibitors. Arch Biochem Biophys. 2003; 412:170-5.

Amendment after Notice of Allowance (Rule 312) dated Jan. 3, 2017 by the U.S. Patent and Trademark Office for U.S. Appl. No. 13/157,803, filed Jun. 10, 2011 now U.S. Pat. No. 9,638,632 on May 2, 2017 (Inventor—Darryl J. Bornhop et al.) (3 pages).

Amendment after Notice of Allowance filed on Feb. 19, 2004 for U.S. Appl. No. 10/053,877, filed Jan. 24, 2002 (Applicant—Vanderbilt University // Inventors—Bornhop et al. //) (8 pages).

Anderson, J.R. et al., Fabrication of topologically complex three-dimensional microfluidic systems in PDMS by rapid prototyping. *Anal Chem.* 72: 3158-64 (2000).

Andersson, A. et at., "TV sherography: quantitative measurement of shear-magnitude fields by use of digital speckle photography," *Applied Optics*, 39: 2565 (2000).

Anonymous (1996-1997) CRC Handbook of Chemistry and Physics (Chemical Rubber Publishing Company, Boca Raton) 77th Ed.).

Anonymous (2001) The human genome. Unsung heroes. Science 291(5507): 1207.

Anuta, "Digital Registration of Multispectral Video Imagery," Society of Photooptical Instrumentation Engineers Journal, vol. 7:168 (1969).

Applicant Initiated Interview Summary (PTOL-413) dated Dec. 2, 2013 for U.S. Appl. No. 13/157,803, filed Jun. 10, 2011 (Applicant—Vanderbilt University // Inventors—Bornhop et al. //) (3 pages).

Applicant Initiated interview Summary (PTOL-413) dated Jul. 23, 2012 for U.S. Appl. No. 12/655,899, filed Jan. 8, 2010 (Applicant—Vanderbilt University // Inventors—Weinberger et al. //) (3 pages).

Applicant Initiated Interview Summary (PTOL-413) dated Sep. 22, 2011 for U.S. Appl. No. 12/331,354, filed Dec. 9, 2008(Applicant—Vanderbilt University // Inventors—Bornhop et al. //) (3 pages).

Arnold F, et al., "Directed Enzyme Evolution," *Meth Mol Biol.* (2003).

Arnold, F.H. "Design by directed evolution," Accounts of Chemical Res. 1998; 31:125-31.

Bachmann, B.O. et al., "Kinetic mechanism of the β-lactam synthetase of Streptomyces clavuligerus," *Biochemistry*, 39: 11187-93 (2000).

Bachmann, O. et al., "β-Lcatam synthetase: A new biosynthetic enzyme," *Proc. Nat. Acad. Sci. USA*. 1998; 95:9082-6.

Baksh, M.M. et al., "Label-free quantification of membrane-ligand interactions using backscattering interferometry," *Nature Biotechnology*, 29: 357-60 (2011).

Baldino, F. et al., "High-resolution in situ hybridization histochemistry," *Methods Enzymol*, 168: 761-77 (1989).

Betzig et al., Single Molecules Observed by near Field Scanning Optical Microscopy. Science. 1993; 262(5138):1422-5.

Bobbitt, D.R. et al., "Direct and Indirect Polarimetry for Detection in Micro bore Liquid Chromatography," Analytical Chemistry, 56: 1577-81 (1984).

Boger, D.L. et al., Discovery of a Potent, Selective, and Efficacious Class of Reversible a-Ketoheterocycle Inhibitors of Fatty Acid Amide Hydrolase Effective as Analgesics. J Med Chem. 2005; 48(6):1849-56.

Bohren CF, et al., "Absoption and Scattering of Light by Small Particles," New York: Wiley (1983).

Borman S, "Combinatorial chemistry," Chemical & Engineering News, 80: 43 (2002).

Bornhop, D.J. et al., Elucidation of the signal origin for label-free, free-solution interactions, Proc Natl Acad Sci. 2016; 113(34):E4931-2.

Swinney, K. et al., "Detection in Capillary Electrophoresis: A Review," *Electrophoresis*. 2000; 21:1239-50.

(56) References Cited

OTHER PUBLICATIONS

Bornhop, D.J. et al., "Polarimetry in capillary dimensions," *Analytical Chemistry*. 1996; 68:1677-84.
Bornhop et al., Free-Solution, Label-Free Molecular Interactions Studief by Back-Scattering Interferometry. Science. 2007; 317(5845):1732-6.
Bornhop, "Microvolume index of refraction determinations by interferometric backscatter," Appl Optics. 34:3234-9 (1995).
Bornhop et al., "Comparison of Free-Solution DNA Hybridization Using Isothermal Titration Calorimetry and Backscattering Interferometry." The 237th ACS National Meeting, Salt Lake City, UT, Mar. 24, 2009, poster abstract.
Bouchara, "Efficient algorithm for computation of the second-order moment of subpixel-edge position," Appl Optics. 43:4550 (2004).
Bowen et al. (2003) "Gas phase detection of trinitrotoluene utilizing a solid-phase antibody immobilized on a gold film by means of surface plasmon resonance spectroscopy" Appl. Spectrosc. 57(8): 906-14.
Bracey, M.H. et al., Structural Adaptations in a Membrane Enzyme Thar Terminates Endocannabinoid Signaling. Science. 2002; 298(5599):1793-6.
Brawer, et al., "Screening for prostatic carcinoma with prostate specific antigen," J. Ural., 147:841-845 (1992).
Bray P, et al., "Human cDNA clones for four species of G Alpha s signal transduction protein," *Proc Natl Sci USA*, 83: 8893-7 (1986).
Brenan, et al., "High throughput, nanoliter quantitative PCR," Drug Discovery Today: Tech, 2:247-53 (2005).
Brockhaus et al., "Thermadynamic studies on the interaction of antibodies with β-amyloid peptide," J Phys Chem B. 111:1238-43 (2007).
Brockman et al., "A Multistep Chemical Modification Procedure to Create DNA Arrays on Gold Surfaces for the Study of Protein-DNA Interactions with Surface Plasmon Resonance Imaging," *J Am Chem Soc*. 121(35):8044-51 (1999).
Burggraf, N. et al., "Holographic Refractive Index Detector for Application in Microchip-based Separation Systems," *Analyst*, 123:1443-7 (1998).
Burke et al., "Stopped-flow enzyme assays on a chip using a microfabricated mixer," Anal Chem, 75(8):1786-91 (2003).
Buynak, J.D. et al., "7-alkylidenecephalosporin esters as inhibitors of human leukocyte elastase," *J. Med. Chem*., 40: 3423-33 (1997).
Buynak, J.D. et al., "Synthesis and Mechanistic Evaluation of 7-Vinylidenecephem Sulfones as P-Lactamase Inhibitors," *J. Am. Chem. Soc*., 116: 10955-65 (1994).
Buynak, J.D. et al., "The Synthesis and β-Lactamase Inhibitory Activity of 6-(Carboxymethylene) Penicillins and 7-(Carboxymethylene) Cephalosporins," *Bioorg. Med. Chem. Lett*., 5: 1513-8 (1995).
Campitelli et al., "Shear horizontal surface acoustic wave based immunosensing system," *Int Conf on Solid State Sensors and Actuators*, Jun. 16-19, 1:187-190 (1997).
Cecchi, A. et al., Carbonic Anhydrase Inhibitors: Inhibition of the Human Isozymes I, II, VA, and IX with a Library of Substituted Difluoromethanesulfonamides. Bioorg med Chem Lett. 2005; 15(23):5192-6.
Choquette et al., "Wavenumber Standards for Near-infrared Spectrometry," Handbook of Vibrational Spectroscopy, John M. Chalmers and Peter R. Griffiths (Editors), 2002, p. 1-7.
Cohen N, et al., "In vitro enzyme evolution: the screening challenge of isolating the one in a million," *Trends in Biotechnol*. 2001; 19(12):507-10.
Collignon et al., "Automated multimodality image registration based on information theory", Information Processing in Medical Imaging (Y. Bizais, C. Barillot and R. Di Paola, eds.), Kluwer Academic Publishers, Dordrecht, pp. 263-274, (1995).
Cravatt, B.F. et al., Chemical Characterization of a Family of Brain Lipids That Induce Sleep. Science. 1995; 268(5216):1506-9.
Crooke, S.T. et al., "Pharmacokinetic properties of several novel oligonucleotide analogs in mice," *J Pharmacol Exp Ther*, 277: 923-937 (1996).

Day, Y.S.N. et al., Direct Comparison of Binding Equilibrium, Thermodynamic, and Rate Constants Determined by Surface- and Solution-Based Biophysical Methods. Protein Sci. 2002; 11(5):1017-25.
DeGrandpre, "Measurement of seawater pCO2 using a renewable-reagent fiber optic sensor with colorimetric detection," *Anal. Chem*., 65: 331-337 (1993).
Dendane et al., "Surface patterning of (bio)molecules onto the inner wall of fused-silica capillary tubes," *Lab Chip*, 8: 2161 (2008).
Deng Y, et al., "On-column Refractive-index detection Based on Retroreflected Beam Interference for Capillary Electrophoresis," *Applied Optics*, 37(6): 998-1005 (1998).
Devane, W.A. et al., Isolation and Structure of a Brain Constituent That Binds to the Cannabinoid Receptor. Science. 1992; 258(5090):1946-9.
Dickinson et al. (1996) A chemical-detecting system based on a crossreactive optical sensor array. Nature 382(6593):697-700.
Dissertation Defense Retrieved from http://calendar.vanderbilt.edu/calendar/2009/11/30/amanda-kathryn-kussrow-dissertation-defense. 95024 on Dec. 22, 2013 (1 page).
Ditchburn RW, "Light," Third Ed. Ed. New York: Academic Press (1976).
Dotson, S.S. et al., "Development of the Ultra Small Volume Polarimeter," Manuscript, Vanderbilt University, 1-11.
Duffy, D.C. et al., "Rapid Prototyping of Microfluidic Systems in Poly(dimethylsiloxane)," *Analytical Chemistry*, 70: 4974-84 (1998).
Election and Preliminary Amendment filed Dec. 19, 2011 for U.S. Appl. No. 12/655,899, filed Jan. 8, 2010 (Applicant—Vanderbilt University // Inventors—Weinberger et al. //) (5 pages).
Election Under Restriction Requirement filed Feb. 18, 2012 for U.S. Appl. No. 12/674,610, filed Oct. 4, 2011 (Applicant—Vanderbilt University // Inventors—Bornhop et al. //) (10 pages).
Examiner-Initiated Interview Summary dated Nov. 3, 2011 for U.S. Appl. No. 11/666,046, filed Jul. 24, 2009 (Applicant—Vanderbilt University // Inventors—Bornhop et al. //) (1 page).
Extended European Search Report dated Jun. 1, 2012 for European Pat. App.No. 05821243.2 filed Oct. 24, 2005 (Applicant—Vanderbilt University // Inventors—Bornhop et al. //) (3 pages).
Extended European Search Report dated Oct. 19, 2012 for European Pat. App. No. 08755681.7 filed May 16, 2008 (Applicant—Vanderbilt Univeristy // Inventors—Jones et al. //) (9 pages).
Fan, et al., "Electrochemical interrogation of conformational changes as a reagentless method for the sequence-specific detection of DNA" Proc Natl Acad Sci USA. 100(16):9134-97 (2003).
Fasman et al., Conformational Changes Associated with F-1 HistoneDeoxyribonucleic Acid Complexes—Circular Dichroism Studies. Biochemistry. 1970; 9(14):2814-22.
Final Rejection dated Aug. 21, 2012 for U.S. Appl. No. 12/655,899, filed Jan. 8, 2010 (Applicant—Vanderbilt University // Inventors—Weinberger et al. //) (18 pages).
Final Rejection dated Aug. 22, 2013 for U.S. Appl. No. 13/157,803, filed Jun. 10, 2011 (Applicant—Vanderbilt University // Inventors—Bornhop et al. //) (17 pages).
Final Rejection dated Feb. 4, 2015 by the U.S. Patent and Trademark Office for U.S. Appl. No. 13/402,104, filed Feb. 22, 2012 now U.S. Pat. No. 9,562,853 on Feb. 7, 2017 (Inventor—Darryl J. Bornhop et al.) (14 pages).
Final Rejection dated Jun. 15, 2016 by the U.S. Patent and Trademark Office for U.S. Appl. No. 13/157,803, filed Jun. 10, 2011 and published as US 2012-0019834 A1 on Jan. 26, 2012 (Inventor—Darryl J. Bornhop; Applicant—Vanderbilt University) (19 Pages).
Final Rejection dated Jun. 23, 2016 by the U.S. Patent and Trademark Office for U.S. Appl. No. 13/402,104, filed Feb. 22, 2012 and published as US-2013-0021608-A1 on Jan. 24, 2013 (Inventor—Darryl J. Bornhop; Applicant—Vanderbilt University) (11 Pages).
Finn, M.G. "Emerging methods for the rapid determination of enantiomeric excess," *Chirality*. 2002; 14: 534-40.
Fintschenko, Y. et al., "Silicon Microtechnology and Microstructures in Separation Science," *Journal of Chromatography A*. 1998; 819:3-12.
Fixman, M. (1962) Radius of Gyration of Polymer Chains. II. Segment Density and Excluded Volume Effects. J Chem Phys. 1962; 36(12):3123-9.

(56) References Cited

OTHER PUBLICATIONS

Fox, S.J. et al., "Assay Innovations Vital to Improving HTS," *Drug Discov Dev*. 2000; 40-3.

Fredrickson, C.K. and Fan, Z.H., Macro-to-Micro Interfaces for Microfluidic Devices. Lab Chip. 2004; 4(6):526-33.

Fricke-Begemann, T. and Burke, J., "Speckle interferometry: three-dimensional deformation field measurement with a single interferogram," Applied Optics. 2001; 40(28):5011-22.

Froestl, W. et al., Phosphinic Acid Analogs of GABA. 1. New Potent and Selective GABAB Agonists. J Med Chem. 1995; 38(17):3297-312.

Garfunkle, J. et al., Optimization of the Central Heterocycle of a-Ketoheterocycle Inhibitors of Fatty Acid Amide Hydrolase. J Med Chem. 2008; 51(15):4392-403.

Gavutis et al., "Lateral ligand-receptor interaction on membranes probed by simultaneous fluorescence-interference detection," *Biophysics J*. 2005; 88(6):4289-302.

Gharagheizi et al. (2014) Group Contribution Model for the Prediction of Refractive Indices of Organic Compounds. J Chem Eng Data 59(6): 1930-1943.

Gibbs, P.R. et al., "Imaging polarimetry for high throughput chiral screening," *Biotechnology Progress*, 19: 1329-1334 (2003).

Gloge, A. et al., "The behavior of substrate analogues and secondary deuterium isotope effects in the phenylalanine ammonia-lyase reaction," *Arch Biochem Biophys*. 1998; 359:1-7.

Golge, A. et al., "Phenylalanine ammonia-lyase: The use of its broad substrate specificity for mechanistic investigations and biocatalysis—Synthesis of Larylalanines," *Chem-A Eur J*. 2000; 6: 3386-90.

Grant CHE 0848788 awarded by the National Science Foundation.

Grant No. F49620-01-1-0429.

Grant No. R01 EB003537-01A2 awarded by National Institutes of Health.

Greisen et al., "PCR primers and probes for the 16S rRNA gene of most species of pathogenic bacteria, including bacteria found in cerebrospinal fluid," J Clin Microbiol. 1994; 32:335-51.

Grosberg and Khokhlov (1994) Statistical Physics of Macromolecules American Institute of Physics, New York.

Grosse A, et al., "Deep wet etching of fused silica glass for hollow capillary optical leaky waveguides in microfluidic devices," *J Micromech Microeng* 2001; 11:257-62.

Guizar-Sicairos et al., "Efficient subpixel image registration algorithms," Optics Letters. 2008; 33:156-15.

Guo, J.H. et al., "Measurement of enantiomeric excess by kinetic resolution and mass spectrometry," *Angewandte Chemie—International Edition*. 1999; 38:1755-8.

Harrison, D.J. et al., "Capillary Electrophoresis and Sample Injection Systems Integrated on a Planar Glass Chip," *Analytical Chemistry*, 64: 1926-1932 (1992).

Harteveld et al., "Detection of Staphylococcal Enterotoxin B employing a piezoelectric crystal immunosensor," *Biosens Bioelectron*. 1997; 12(7):661-7.

Hecht E, "Optics," New York: Addison-Wesley Longman (1998).

Heideman et al., Performance of a highly sensitive optical waveguide Mach-Zehnder interferometer immunosensor, Sensors and Actuators B—Chemical. 1993; 10(3):209-17.

Heideman et al., "Remote opto-chemical sensing with extreme sensitivity: design, fabrication and performance of a pigtailed integrated optical phase-modulated Mach-Zehnder interferometer system," *Sensors and Actuators*, B 61: 100-127 (1999).

Heikkinen, H. et al., "Interpretation of interference signals in label free integrated interferometric biosensors," *Proceedings of the SPIE*, 2006; 6094:60940P-1.

Hell, S.W. & Wichmann, J., Breaking the diffraction resolution limit by stimulated emission: stimulated-emission-depletion fluorescence microscopy. Opt Lett. 1994; 19(11):780-2.

Hodgins, D.S., "Yeast Phenylalanine Ammonia-Lyase—Purification, Properties, and Identification of Catalytically Essential Dehydroalanine," J Biol Chem. 1971; 246:2977.

Hofstetter, O. et al., "Antibodies as chiral selectors for the determination of enantioenrichment," *Enantiomer*. 2001; 6:153-8.

Horton et al., "Interference patterns of a plane-polarized wave from a hollow glass fiber," *J Opt Soc Am*. 1973; 63:1204-10.

Hu et al., The mode of action of centrin—Binding of Ca2+ and a peptide fragment of Kar1p to the C-terminal domain. J Biol Chem. 2004; 279(49):50895-903.

Hubbard et al., "Calmodulin binding by calcineurin," *J Biol Chem*. 1987; 262(31):15062-70.

Hudlicky, T.M. et al., "Microbial Oxidation of Aromatics in Enantiocontrolled Synthesis .1. Expedient and General AsymmetricSynthesis of Inositols and Carbohydrates Via an Unusual Oxidation of a Polarized Diene with Potassium Permanganate," *J Chem Soc Perkin Trans*. 1994; 1:1553-67.

Huntley, "Speckle photography fringe analysis: assessment of current algorithms," Applied Optics. 1989; 28:4316.

International Preliminary Examination Report dated Nov. 28, 2001 for PCT/US2000/020783 filed Aug. 17, 2000 and published as WO 2001/014858 on Mar. 1, 2001 (Applicant—Texas Tech University Health Sciences Center // Inventors—Bornhop et al. //) (5 pages).

International Preliminary Report on Patentability dated Mar. 24, 2010 for PCT/US2008/077145 filed Sep. 20, 2008 and published as WO 2009/039466 on Mar. 26, 2009 (Applicant—Vanderbilt University // Inventors—Bornhop et al. //) (9 pages).

International Preliminary Report on Patentability dated Apr. 16, 2013 for PCT/US2011/056171 filed Oct. 13, 2011 and published as WO 2012/051429 on Apr. 19, 2012 (Applicants—Vanderbilt University // Inventors—Bornhop et al. //) (7 pages).

International Preliminary Report on Patentability dated Jul. 12, 2011 for PCT/US2010/000047 filed Jan. 8, 2010 and published as WO 2010/080710 on Jul. 15, 2010 (Applicants—Molecular Sensing, Inc. et al. // Inventors—Weinberger et al. //) (5 pages).

International Preliminary Report on Patentability dated Nov. 24, 2009 for US/PCT/2008/063879 filed May 16, 2008 and published as WO 2008/144496 on Nov. 27, 2008 (Applicant—Vanderbilt University // Inventors—Jones et al. //) (10 pages).

International Preliminary Report on Patentability dated Dec. 14, 2012 for PCT/US2011/039982 filed Jun. 10, 2011 and published as WO 2011/156713 on Dec. 15, 2011 (Applicants—Vanderbilt University // Inventors—Bornhop et al. //) (5 pages).

International Preliminary Report on Patentability dated Apr. 24, 2007 for PCT/US2005/38168 filed Oct. 24, 2005 and published as WO 2006/047408 on May 4, 2006 (Applicants—Vanderbilt University // Inventors—Bornhop et al. //) (6 pages).

International Preliminary Report on Patentability dated Jul. 25, 2017 by the International Searching Authority for Patent Application No. PCT/US2016/014439, which was filed on Jan. 22, 2016 and published as WO 2016/118812 on Jul. 28, 2016 (Inventor—Bornhop et al.; Applicant—Vanderbilt University;) (8 pages).

International Search Report and Written Opinion dated Mar. 8, 2012 for PCT/US2011/056171 filed Oct. 13, 2011 and published as WO 2012/051429 on Apr. 19, 2012 (Applicants—Vanderbilt University // Inventors—Bornhop et al. //) (8 pages).

International Search Report and Written Opinion dated Aug. 19, 2008 for US/PCT/2008/063879 filed May 16, 2008 and published as WO 2008/144496 on Nov. 27, 2008 (Applicant—Vanderbilt University // Inventors—Jones et al. //) (11 pages).

International Search Report and Written Opinion dated Sep. 30, 2010 for PCT/US2010/000047 filed Jan. 8, 2010 and published as WO 2010/080710 on Jul. 15, 2010 (Applicants—Molecular Sensing, Inc. et al. // Inventors—Weinberger et al. //) (7 pages).

International Search Report and Written Opinion dated Oct. 5, 2011 for PCT/US2011/039982 filed Jun. 10, 2011 and published as WO 2011/156713 on Dec. 15, 2011 (Applicants—Vanderbilt University // Inventors—Bornhop et al. //) (6 pages).

International Search Report and Written Opinion dated Dec. 8, 2008 for PCT/US2008/077145 filed Sep. 20, 2008 and published as WO 2009/039466 on Mar. 26, 2009 (Applicant—Vanderbilt University // Inventors—Bornhop et al. //) (9 pages).

International Search Report and Written Opinion dated Apr. 26, 2006 for PCT/US2005/038168 filed Oct. 24, 2005 and published as WO 2006/047408 on May 4, 2006 (Applicants—Vanderbilt University // Inventors—Bornhop et al. //) (7 pages).

(56) References Cited

OTHER PUBLICATIONS

International Search Report and Written Opinion dated Mar. 24, 2016 by the International Searching Authority for Patent Application No. PCT/US2016/014439, which was filed on Jan. 22, 2016 and published as WO 2016/118812 on Jul. 28, 2016 (Inventor—Bornhop et al.; Applicant—Vanderbilt University;) (13 pages).
International Search Report and Written Opinion dated May 25, 2017 by the International Searching Authority for International Application No. PCT/US2017/015296, which was filed on Jan. 27, 2017 (Applicant—Vanderbilt University) (10 pages).
Issue Notification issued Feb. 1, 2012 for U.S. Appl. No. 12/331,354, filed Dec. 9, 2008 (Applicant—Vanderbilt University // Inventors—Bornhop et al. //) (1 page).
Issue Notification issued on Feb. 22, 2012 for U.S. Appl. No. 11/666,046, filed Jul. 24, 2009 (Applicant—Vanderbilt University // Inventors—Bornhop et al. //) (1 page).
Issue Notification issued on Apr. 5, 2013 for U.S. Appl. No. 12/674,610, filed Oct. 4, 2011 (Applicant—Vanderbilt University // Inventors—Bornhop et al. //) (1 page).
Issue Notification issued on Oct. 27, 2010 for U.S. Appl. No. 12/122,175, filed May 16, 2008 (Applicant—Vanderbilt University // Inventors—Jones et al. //) (1 page).
Issue Notification was issued on Jan. 18, 2017 by the U.S. Patent and Trademark Office for U.S. Appl. No. 13/402,104, filed Feb. 22, 2012 and granted as U.S. Pat. No. 9,562,853 on Feb. 7, 2017 (Inventor—Darryl J. Bornhop et al.) (1 page).
Issue Notification was issued on Feb. 10, 2016 by the U.S. Patent and Trademark Office for U.S. Appl. No. 13/892,642, filed May 13, 2013 and granted as U.S. Pat. No. 9,273,949 on Mar. 1, 2016 (Inventor—Darryl J. Bornhop et al.) (1 page).
Issue Notification was issued on Apr. 12, 2017 by the U.S. Patent and Trademark Office for U.S. Appl. No. 13/157,803, filed Jun. 10, 2011 and granted as U.S. Pat. No. 9,638,632 on May 2, 2017 (Inventor—Darryl J. Bornhop et al.) (1 page).
Ivanov et al., The B to A transition of DNA in solution. J Mol Biol. 1974; 87(4):817-33.
Jacobson, S.C. et al., "Fused Quartz Substrates for Microchip Electrophoresis," *Anal Chem*. 1995; 67:2059-63.
Jacobson, S.C. et al., "Microfluidic devices for electrokinetically driven parallel and serial mixing," *Anal Chem*. 1999; 71:4455-9.
Jass, J. et al., From Liposomes to Supported, Planar Bilayer Structures on Hydrophilic and Hidrophobic Surfaces: an Atomic Force Microscopy Study. Biophys J. 2000; 79(6):3153-63.
Jepsen, S.T. et al., Evaluation of back scatter interferometry, a method for detecting protein binding in solution. Analyst. 2015; 140(3):895-901.
Jepsen S.T. (2016) Back Scatter Interferometric Sensor for Label-Free Medical Diagnostic Assays, Aalborg University (1-120 pages).
Jorgensen, T.M. et al., Back scattering interferometry revisited—A theoretical and experimental investigation, Sensors and Actuators B. 2015; 220:1328-37.
Jung, L.S. et al., Quantitative Interpretation of the Response of Surface Plasmon Resonance Sensors to Adsorbed Films. Langmuir. 1998; 14(19):5636-48.
Kabanov, A.V. et al., "A new class of antivirals: antisense oligonucleotides combined with a hydrophobic substituent effectively inhibit influenza virus reproduction and synthesis of virus-specific proteins in MDCK cells," *FEBS Letters*. 1990; 259(2):327-30.
Kalghatgi, K.K. et al., "Microbial L-phenylalanine ammonia-lyase. Purification, subunit structure and kinetic properties of the enzyme from Rhizoctonia sol ani," *Biochem J*. 1975; 149:65-75.
Kalinina et al., "Nanoliter scale PCR with TaqMan detection," *Nucleic Acid Research*, 1997; 25(10):1999-2004.
Kaltashov et al., Advances and challenges in analytical characterization of biotechnology products: Mass spectrometry-based approaches to study properties and behavior of protein therapeutics. Biotechnol Adv. 2012; 30(1):210-22.
Katritzky et al., Correlation and prediction of the refractive indices of polymers by QSPR. J Chem Inf Comp Sci. 1998; 38(6):1171-6.

Kaupmann, K. et al., Expression Cloning of GABAB Receptors Uncovers Similarity to Metabotropic Gultamate Receptors. Nature. 1997; 386(6622):239-46.
Keen et al., "Rapid detection of single base mismatches as heteroduplexes on Hydrolilnk gels," Trends Genet. 1991; 7:5.
Kenmore, C.K. et al., "Refractive-index Detection by interferometric Backscatter in Packed-capillary High-performance Liquid Chromatography," *J Chromatog A*. 1997; 762:219-25.
Kerker, M. et al., "Scattering of Electomagnetic Waves from Concentric Infinite Cylinders," J Opt Soc Amer. 1961; 51:506-8.
Buynak, J.D. et al., "Synthesis and Biological-Activity of 7-Alkylidenecephems," *J Med Chem*. 1995; 38:1022-34.
Klee et al., "Purification of cyclic 3',5'-nucleotide phosphodiesterase inhibitory protein by affinity chromatography on activator protein couples to sepharose," Biochemistry. 1978; 17:120-6.
Koradi et al. (1996) MOLMOL: A program for display and analysis of macromolecular structures. J Mol Graphics 14(1 ):51-55.
Korbel, G.A. et al., "Reaction microarrays: A method for rapidly determining the enantiomeric excess of thousands of samples," *J Amer Chem Soc*. 2001; 123:361-2.
Krummel, M.F. and Davis, M.M., Dynamics of the Immunological Synapse: Finding, Establishing and Solidifying a Connection. Curr Opin Immunol. 2002; 14(1):66-74.
Kuhlmann, J., "Drug Research: From the Idea to the Product," *Int J Clin Pharmacol Ther*. 1997; 35(12):541-52.
Kunkel, T.A. et al., "Rapid and efficient site-specific mutagenesis without phenotypic selection," *Methods Enzymol*. 1987; 154:367-82.
Kussrow A, et al., "Measurement of Mono- and Polyvalent Carbohydrate-Lectin Binding by Back-Scattering Interferometry," *Anal Chem*. 2009; 81:4889-97.
Kussrow et al., Interferometric Methods for Label-Free Molecular Interaction Studies. Anal Chem. 2012; 84(2):779-92.
Kussrow, "Interogation of Biomolecular Interactions Utilizing Backscattering Interferometry," Dissertation, Vanderbilt University (2009), pp. i-xii and 1-115 (127 pages total), retrieved from http://etd.library.vanderbilt.edu/available/etd-12042009-092927 on Apr. 29, 2013.
Kussrow, A. et al., Universal Sensing by Transduction of Antibody Binding with Backscattering Interferometry. Chembiochem. 2011; 12(3):367-70.
Kypr et al., Circular dichroism and conformational polymorphism of DNA Nucleic Acids Res. 2009; 37(6):1713-25.
Lan et al., "Non-mechanical sub-pixel image shifter for acquiring super-resolution digital images," Optics Express. 2009; 17:22992-3002.
Langone, "Protein A of *Staphylococcus aureus* and related immunoglobulin receptors produced by streptococci and pneumonococci," *Adv Immunol*. 1982; 32:157-252.
Latham et al., "Photobiotin surface chemistry improves label-free interferometric sensing of biochemical interactions," *Angew Chem Int Ed*. 2006; 45:955-8.
Leslie and Lilley, Aqueous solutions containing amino acids and peptides. Part 20. Volumetric behavior of some terminally substituted amino acids and peptides at 298.15 K. Biopolymers. 1985; 24(4):695-710.
Letsinger et al., "Cholesteryl-conjugated oligonucleotides: Synthesis, properties, and activity as inhibitors of replication of human immunodeficiency virus in cell culture," Proc Natl Acad Sci USA. 1989; 86:6553-6.
Levene et al., Zero-mode waveguides for single-molecule analysis at high concentrations. Science. 2003; 299(5607):682-6.
Liang, Y., Applications of isothermal titration calorimetry in protein folding and molecular recognition. J Iran Chem Soc. 2006; 3(3):209-19.
Liedberg et al., Biosensing with Surface-Plasmon Resonance—How It All Started. Biosens Bioelectron. 1995; 10(8):R1-9.
Liu, S.R. et al., "Optimization of high-speed DNA sequencing on microfabricated capillary electrophoresis channels," Anal Chem. 1999; 71:566-73.
Lodish et al. (1990) Molecular Cell Biology (Scientific American Books, New York).
Malacara, D. et al., "Interferogram Analysis for Optical Testing," New York: Marcel Dekker, Inc. (1998).

(56) References Cited

OTHER PUBLICATIONS

Manoharan, M. et al., "Chemical modifications to improve uptake, and bioavailability of antisense oligonucleotides," *Ann NY Acad Sci*. 1992; 660:306-9.
Manoharan, M. et al., "Cholic acid-oligonucleotide conjugates for antisense applications," *Biorg Med Chem Lett*. 1994; 4:1053-60.
Manoharan, M. et al., "Introduction of a Lipophilic Thioether Tether in the Minor Groove of Nucleic Acids for Antisense Applications," *Bioorg Med Chem Lett*. 1993; 3:2765-70.
Manoharan, M. et al., "Lipidic nucleic acids," *Tetrahedron Lett*. 1995; 36: 3651-4.
Manoharan, M. et al., "Oligonucleotide conjugates: alteration of the pharmacokinetic properties of antisense agents," *Nucleosides & Nucleotides*. 1995; 14:969-73.
Manz, A. et al., "Micromachining of Monocrystalline Silicon and Glass for Chemical-Analysis Systems—a Look into Next Century Technology or Just a Fashionable Craze," Trac-Trends in Anal Chem. 1991; 10:144-9.
Manz, A. et al., "Miniaturized Total Chemical-Analysis Systems—a Novel Concept for Chemical Sensing," *Sensors and Actuators B—Chemical*. 1990; 1:244-8.
Marcuse et al., "Light scattering from optical fibers with arbitrary refractive-index distributions," J Opt Soc Am. 1975; 65:367-75.
Marketwired, "Molecular Sensing, Inc. and VIB Enter Agreement in Alzheimer's Disease Research." Internet Publication http://www.marketwired.com/press-release/molecular-sensing-inc-and-vib-enter-agreement-in-alzheimers-disease-research-1231768.htm (2009).
Markov, D. et al., "A Fourier Analysis Approach for Capillary Polarimetry," *Electrophoresis*. 2002; 23(5):809-12.
Markov, D. et al., "Breaking the 10-7 Barrier for RI Measurements in Nanoliter Volumes," *Analytical Chemistry*. 2002; 74:5438-41.
Markov, D. et al., "Nanoliter-scale Non-invasive Flow-Rate Quantification using Micro-Interferometric Backscatter and Phase Detection," *Fresenius' J Anal Chem*. 2001; 371:234-7.
Markov, D.A. et al., "Non-Invasive Fluid Flow Measurements in Microfluidic Channels with Backscatter Interferometry," Submitted to Electrophoresis 2004.
Markov et al., "Label-Free Molecular Interaction Determinations with Nanoscale Interferometry," J Am Chem Soc. 2004; 126:16659-64.
Marsh and Teichman, Relative Solvent Accessible Surface Area Predicts Protein Conformational Changes upon Binding. Structure. 2011; 19(6):859-67.
Martynova L, et al., "Fabrication of plastic micro fluid channels by imprinting methods," *Analytical Chemistry*. 1997; 69:4782-9.
Mathworks, "Registering an Image Using Normalized Cross-Correlation," http://www.mathworks.com/products/demos/image/cross-correlation/imreg.html, last accessed May 15, 2014 (5 pages).
May, O. et al., "Inverting enantioselectivity by directed evolution of hydantoinase for improved production ofL-methionine," Nature Biotechnol. 2000; 18:317-20.
Maystre, F. et al., "Enhanced Polarimetric Detection in Hplc Using a Refractive-Index Equalizer," *Analytical Chemistry*. 1994; 66:2882-7.
Miller, M.T. et al., "Structure of β-lactam synthetase reveals how to synthesize antibiotics instead of asparagine," *Nature Struct Biol*. 2001; 8:684-9.
Miller, M.T. et al., "The catalytic cycle of β-lactam synthetase observed by x-ray crystallographic snapshots," *Proc Nat Acad Sci USA*. 2002; 99:14752-7.
Minor, L.K., Label-Free Cell-Based Functional Assays. Comb Chem High Throughput Screen. 2008; 11(7):573-80.
Miroshnikova et al., "Percussion hole drilling of metals with a fourth-harmonic Nd: YAG laser studied by defocused laser speckle correlation," Applied Optics. 2005; 44:3403.
Mishra, R.K. et al., "Improved leishmanicidal effect of phosphorothioate antisense oligonucleotides by LDL-mediated delivery," *Biochim Biophys Acta*. 1995; 1264:229-327.
Molphy et al., "Surface Modification of Kaolin. 1. Covalent Attachement of Polyethylene Glycol using a Urethane Linker," *Polymer Intl*. 1994; 34:425-31.
Montigiani et al., "Alanine substitutions on calmodulin-binding peptides result in unexpected affinity enhancement," *J Mol Biol*. 1996; 258:6-13.
Morcos, E.F. et al., Free-Solution Interaction Assay of Carbonic Anhydrase to Its Inhibitors Using Back-Scattering Interferometry. Electrophoresis. 2010; 31(22):3691-5.
Moreira et al., Effects of fluorescent dyes, quenchers, and dangling ends on DNA duplex stability. Biochem Biophys Res Co. 2005; 327(2):473-84.
Morrison, et al., "Nanoliter high throughput quantitative PCR," Nucleic Acid Res. 2004; 34(18):e123.
Neifeld, "Information, resolution, and space-bandwidth product," Optics Lett. 1998; 23:1477-9.
Nielson, P.E. et al., "Sequence-selective recognition of DNA by strand displacement with a thymine-substituted polyamide," *Science*. 1991; 254:1497-500.
Non Final Rejection was issued on 030/2/2015 by the U.S. Patent and Trademark Office for U.S. Appl. No. 13/892,642, filed May 13, 2013 now U.S. Pat. No. 9,273,949 on Mar. 1, 2016 (Inventor—Darryl J. Bornhop et al.) (12 pages).
Non Final Rejection dated Jul. 3, 2017 by the USPTO for U.S. Appl. No. 13/879,523, filed Jun. 28, 2013 and published as US 2013-0280715 A1 on Oct. 24, 2013 (Inventor—Darryl J. Bornhop) (13 pages).
Non Final Rejection dated Aug. 21, 2015 by the U.S. Patent and Trademark Office for U.S. Appl. No. 13/402,104, filed Feb. 22, 2012 now U.S. Pat. No. 9,562,853 on Feb. 7, 2017 (Inventor—Darryl J. Bornhop et al.) (11 pages).
Non-Final Rejection dated Jan. 2, 2014 for U.S. Appl. No. 13/409,557, filed Mar. 1, 2012 (Applicant—Vanderbilt University // Inventors—Bornhop et al. //) (35 pages).
Non-Final Rejection dated Feb. 21, 2012 for U.S. Appl. No. 12/655,899, filed Jan. 8, 2010 (Applicant—Vanderbilt University // Inventors—Weinberger et al. //) (20 pages).
Non-Final Rejection dated Mar. 19, 2013 for U.S. Appl. No. 13/157,803, filed Jun. 10, 2011 (Applicant—Vanderbilt University // Inventors—Bornhop et al. //) (16 pages).
Non-Final Rejection dated May 6, 2013 for U.S. Appl. No. 13/409,557, filed Mar. 1, 2012 (Applicant—Vanderbilt University // Inventors—Bornhop et al. //) (19 pages).
Non-Final Rejection dated May 13, 2014 for U.S. Appl. No. 13/402,104, filed Feb. 22, 2012 (Applicant—Vanderbilt University // Inventors—Bornhop et al. //) (11 pages).
Non-Final Rejection dated Jun. 7, 2012 for U.S. Appl. No. 12/674,610, filed Oct. 4, 2011 (Applicant—Vanderbilt University // Inventors—Bornhop et al. //) (21 pages).
Non-Final Rejection dated Jul. 23, 2014 for U.S. Appl. No. 13/157,803, filed Jun. 10, 2011 (Applicant—Vanderbilt University // Inventors—Bornhop et al. //) (17 pages).
Non-Final Rejection dated Oct. 2, 2012 for U.S. Appl. No. 13/157,803, filed Jun. 10, 2011 (Applicant—Vanderbilt University // Inventors—Bornhop et al. //) (17 pages).
Non-Final Rejection dated Nov. 23, 2015 for U.S. Appl. No. 13/157,803, filed Jun. 10, 2011 (Applicant—Vanderbilt University II Inventors—Bornhop et al. //) (18 pages).
Non-Final Rejection dated Mar. 24, 2011 for U.S. Appl. No. 12/331,354, filed Dec. 28, 2008 (Applicant—Vanderbilt University // Inventors—Bornhop et al. //) (15 pages).
Non-Final Rejection dated Apr. 28, 2010 for U.S. Appl. No. 12/122,175, filed May 16, 2008 (Applicant—Vanderbilt University // Inventors—Jones et al. //) (18 pages).
Non-Final Rejection dated Jun. 29, 2010 for U.S. Appl. No. 12/122,175, filed May 16, 2008 (Applicant—Vanderbilt University // Inventors—Jones et al. //) (18 pages).
Non-Final Rejection dated Jul. 8, 2003 for U.S. Appl. No. 10/053,877, filed Jan. 24, 2002 (Applicant—Vanderbilt University // Inventors—Bornhop et al. //) (6 pages).
Notice of Allowance dated Mar. 20, 2013 for U.S. Appl. No. 12/674,610, filed Oct. 4, 2011 (Applicant—Vanderbilt University // Inventors—Bornhop et al. //) (10 pages).

(56) References Cited

OTHER PUBLICATIONS

Notice of Allowance dated Jul. 22, 2010 for U.S. Appl. No. 12/122,175, filed May 16, 2008 (Applicant—Vanderbilt University // Inventors—Jones et al. //) (7 pages).
Notice of Allowance dated Sep. 10, 2010 for U.S. Appl. No. 12/122,175, filed May 16, 2008 (Applicant—Vanderbilt University // Inventors—Jones et al. //) (4 pages).
Notice of Allowance dated Oct. 11, 2011 for U.S. Appl. No. 12/331,354, filed Dec. 9, 2008 (Applicant—Vanderbilt University // Inventors—Bornhop et al. //) (7 pages).
Notice of Allowance dated Nov. 3, 2011 for U.S. Appl. No. 11/666,046, filed Jul. 24, 2009 (Applicant—Vanderbilt University // Inventors—Bornhop et al. //) (8 pages).
Notice of Allowance dated May 28, 2004 for U.S. Appl. No. 10/053,877, filed Jan. 24, 2002 (Applicant—Vanderbilt University // Inventors—Bornhop et al. //) (7 pages).
Notice of Allowance dated Nov. 20, 2003 for U.S. Appl. No. 10/053,877, filed Jan. 24, 2002 (Applicant—Vanderbilt University // Inventors—Bornhop et al. //) (7 pages).
Notice of Allowance dated Oct. 11, 2016 by the U.S. Patent and Trademark Office for U.S. Appl. No. 13/402,104, filed Feb. 22, 2012 now U.S. Pat. No. 9,562,853 on Feb. 7, 2017 (Inventor—Darryl J. Bornhop et al.) (9 pages).
Notice of Allowance dated Oct. 30, 2015 by the U.S. Patent and Trademark Office for U.S. Appl. No. 13/892,642, filed May 13, 2013 now U.S. Pat. No. 9,273,949 on Mar. 1, 2016 (Inventor—Darryl J. Bornhop et al.) (8 pages).
Notice of Allowance dated Oct. 31, 2016 by the U.S. Patent and Trademark Office for U.S. Appl. No. 13/157,803, filed Jun. 10, 2011 now U.S. Pat. No. 9,638,632 on May 2, 2017 (Inventor—Darryl J. Bornhop et al.) (12 pages).
Oberhauser, B. et al, "Effective incorporation of 2'-O-methyl-obligoribonucleotides into liposomes and enhanced cell association through modification with thiocholesterol," *Nucleic Acids Research*, 1992; 20(3):533-8.
Olmsted et al., Toward Rapid, High-Sensitivity, Volume-Constrained Biomarker Quantification and Validation using backscattering Interferometry. Anal Chem. 2014; 86:7566-74.
Olmsted, I.R. et al., Comparison of Free-solution and Surface-Immobilized Molecular Interactions Using a Single Platform, Back-Scattering Interferometry. Anal Chem. 2012; 84(24):10817-22.
Orita et al., "Rapid and sensitive detection of point mutations and DNA polymorphisms using the polymerase chain reaction," Genomics. 1989; 5:874-9.
Overington, J.P. et al., How Many Drug Targets Are There? Nat Rev Drug Discov. 2006; 5(12):993-6.
Papalia, G.A. et al., Comparative Anaylsis of 10 Small Molecules Binding to Carbonic Anhydrase II by Different Investigators Using Biacore Technology. Anal Biochem. 2006; 359(1):94-105.
PDR-Chiral, Development of a New Laser Based Polarimetric Detector and Its Application to High-performance Liquid Chromatography, *HPLC* (1998).
Persson et al., "Lipid-Based Passivation in Nanofluidics," *Nano Letters*. 2012; 12:2260-5.
Pesciotta et al., Back-Scattering Interferometry: A Versatile Platform for the Study of Free-Solution versus Surface-Immobilized Hybridization. Chemistry—an Asian J. 2011; 6(1):70-3.
Pettersen et al., UCSF chimera—A visualization system for exploratory research and analysis. J Comput Chem. 2004; 25(13):1605-12.
Pin, J.P. et al., Activation Mechanism of the Heterodimeric GABAB Receptor. Biochem Pharmacol. 2005; 68(8):1565-72.
Pitter et al., "Focus errors and their correction in microscopic deformation analysis using correlation," Optics Express. 2002; 10:1361-7.
Porat B, "A Course in Digital Signal Processing," New York: Wiley and Sons (1997).
Preliminary Amendment filed Apr. 15, 2013 for U.S. Appl. No. 13/879,523, filed Jun. 28, 2013 (Applicant—Vanderbilt University // Inventors—Bornhop et al. //) (7 pages).
Preliminary Amendment filed Jun. 5, 2009 for U.S. Appl. No. 12/331,354, filed Dec. 9, 2008 (Applicant—Vanderbilt University // Inventors—Bornhop et al. //) (4 pages).
Preliminary Amendment filed Jul. 12, 2010 for U.S. Appl. No. 12/655,899, filed Jan. 8, 2010 (Applicant—Vanderbilt University // Inventors—Weinberger et al. //) (2 pages).
Preliminary Amendment filed Oct. 4, 2011 for U.S. Appl. No. 12/674,610, filed Oct. 4, 2011 (Applicant—Vanderbilt University // Inventors—Bornhop et al. //) (9 pages).
Project et al., A molecular dynamics study of the effect of Ca2+ removal on calmodulin structure. Biophys J. 2006; 90(11):3842-50.
Qian et al., Characterization of antigen-antibody complexes by size-exclusion chromatography coupled with low-angle light-scattering photometry and viscometry. J Chromatogr A. 1997; 787(1-2):101-9.
Quake, S.R. et al., "From micro- to nanofabrication with soft materials," *Science*. 2000; 290:1536-40.
Read et al., "Aseptic meningitis and encephalitis: the role of PCR in the diagnostic laboratory," Clin Microbiol. 1997; 35:691-6.
Reem et al., "Induction and upregulation by interleukin 2 of high-affinity interleukin 2 receptors on thymocytes and T cells," Proc Natl Acad Sci USA. 1985; 82:8663-6.
Reetz, M.T., "Combinatorial and evolution-based methods in the creation of enantioselective catalysts," *Angewandte Chemie—International Edition*. 2001; 40:284-310.
Reetz, M.T., "New methods for the high-throughput screening of enantioselective catalysts and biocatalysts," *Angewandte Chemie—International Edition*. 2002; 41:1335-8.
Response to Office Action filed Feb. 4, 2013 for U.S. Appl. No. 13/157,803, filed Jun. 10, 2011 (Applicant—Vanderbilt University // Inventors—Bornhop et al. //) (10 pages).
Request for Continued Examination filed on Jan. 22, 2014 for U.S. Appl. No. 13/157,803, filed Jun. 10, 2011 (Applicant—Vanderbilt University // Inventors—Bornhop et al. //) (15 pages).
Requirement for Restriction/Election dated Oct. 18, 2011 for U.S. Appl. No. 12/655,899, filed Jan. 8, 2010 (Applicant—Vanderbilt University // Inventors—Weinberger et al. //) (10 pages).
Requirement for Restriction/Election dated Dec. 19, 2011 for U.S. Appl. No. 12/674,610, filed Oct. 4, 2011 (Applicant—Vanderbilt University // Inventors—Bornhop et al. //) (12 pages).
Requirement for Restriction/Election dated Dec. 28, 2010 for U.S. Appl. No. 12/331,354, filed Dec. 9, 2008 (Applicant—Vanderbilt University // Inventors—Bornhop et al. //) (12 pages).
Resetar, S. et al., "Anticipating Technological Change: Combinatorial Chemistry and the Environment," *EPA* (2001).
Response to Final Office action filed Jan. 22, 2014 for U.S. Appl. No. 13/157,803, filed Jun. 10, 2011 (Applicant—Vanderbilt University // Inventors—Bornhop et al. //) (12 pages).
Response to Final Office action filed Oct. 23, 2014 for U.S. Appl. No. 13/157,803, filed Jun. 10, 2011 (Applicant—Vanderbilt University // Inventors—Bornhop et al. //) (12 pages).
Response to Final Rejection dated Oct. 21, 2016 to the U.S. Patent and Trademark Office for U.S. Appl. No. 13/157,803, filed Jun. 10, 2011 now U.S. Pat. No. 9,638,632 on May 2, 2017 (Inventor—Darryl J. Bornhop et al.) (13 pages).
Response to Non Final Rejection dated Feb. 22, 2016 to the U.S. Patent and Trademark Office for U.S. Appl. No. 13/402,104, filed Feb. 22, 2012 now U.S. Pat. No. 9,562,853 on Feb. 7, 2017 (Inventor—Darryl J. Bornhop et al.) (9 pages).
Response to Non Final Rejection dated Jul. 2, 2015 by the U.S. Patent and Trademark Office for U.S. Appl. No. 13/892,642, filed May 13, 2013 now U.S. Pat. No. 9,273,949 on Mar. 1, 2016 (Inventor—Darryl J. Bornhop et al.) (11 pages).
Response to Non-Final Office action filed Oct. 7, 2013 for U.S. Appl. No. 13/409,557, filed Mar. 1, 2012 (Applicant—Vanderbilt University // Inventors—Bornhop et al. //) (9 pages).
Response to Non-Final Office Action filed Nov. 13, 2014 for U.S. Appl. No. 13/402,104, filed Feb. 22, 2012 (Applicant—Vanderbilt University // Inventors—Bornhop et al. //) (14 pages).
Response to Non-Final Rejection filed Oct. 1, 2003 for U.S. Appl. No. 10/053,877, filed Jan. 24, 2002 (Applicant—Vanderbilt University // Inventors—Bornhop et al. //) (2 pages).

(56) References Cited

OTHER PUBLICATIONS

Response to Non-Final Rejection dated Jul. 23, 2012 for U.S. Appl. No. 12/655,899, filed Jan. 8, 2010 (Applicant—Vanderbilt University // Inventors—Weinberger et al. //) (11 pages).
Response to Office Action filed Jun. 29, 2010 for U.S. Appl. No. 12/122,175, filed May 16, 2008 (Applicant—Vanderbilt University // Inventors—Jones et al. //) (17 pages).
Response to Office Action filed Jul. 19, 2013 for U.S. Appl. No. 13/157,803, filed Jun. 10, 2011 (Applicant—Vanderbilt University // Inventors—Bornhop et al. //) (11 pages).
Response to Office Action filed Sep. 21, 2011 for U.S. Appl. No. 12/331,354, filed Dec. 9, 2008 (Applicant—Vanderbilt University // Inventors—Bornhop et al. //) (14 pages).
Response to Office Action filed Dec. 7, 2012 for U.S. Appl. No. 12/674,610, filed Oct. 4, 2011 (Applicant—Vanderbilt University // Inventors—Bornhop et al. //) (13 pages).
Response to Restriction Requirement filed Jan. 20, 2011 for U.S. Appl. No. 12/331,354, filed Dec. 9, 2008 (Applicant—Vanderbilt University // Inventors—Bornhop et al. //) (9 pages).
Response to Restriction Requirement filed Mar. 7, 2013 for U.S. Appl. No. 13/409,557, filed Mar. 1, 2012 (Applicant—Vanderbilt University // Inventors—Bornhop et al. //) (2 pages).
Restriction Requirement dated Jan. 7, 2013 for U.S. Appl. No. 13/409,557, filed Mar. 1, 2012 (Applicant—Vanderbilt University // Inventors—Bornhop et al. //) (6 pages).
Rich et al., "High-resolution and high-throughput protocols for measuring drug/human serum albumin interactions using BIACORE," *Anal Biochem.* 2001; 296:197-207.
Romero, F.A. et al., Potent and Selective a-Ketoheterocycle-Based Inhibitors of the Anandamide and Oleamide Catabolizing Enzyme, Fatty Acid Amide Hydrolase. J Med Chem. 2007; 50(5):1058-68.
Rother, D. et al., "An active site homology model of phenylalanine ammonia-lyase from Petroselinum crispum," Eur J Biochem. 2002; 269:3065-75.
Rouhi, A.M., "Chiral chemistry," *Chemical & Engineering News.* 2004; 82:47-62.
Rouhi, A.M., "Taking a measure of chiral riches—Researchers respond to high demand for ways to measure enantioenrichment quickly," *Chemical & Engineering News.* 2002; 80:51-7.
Rouhi A.M. et al., "Chiral roundup—As pharmaceutical companies face bleak prospects, their suppliers diligently tend the fertile fields of chiral chemistry in varied ways," *Chemical & Engineering News.* 2002; 80:43-50.
Rudolph Research Analytical, "Polarimetry," webpage retried from www.rudolphresearch.com/polarimetry.htm, (last accessed Aug. 3, 2009) (2 pages).
Rychlik W, et al., "New algorithm for determining primer efficiency in PCR and sequencing," J NIH Res. 1994; 6(9):78 (2 pages).
Saetear et al., Quantification of Plasmodium-host protein interactions on intact, unmodified erythrocytes by back-scattering interferometry. Malaria J. 2015; 14:88 (9 pages).
Saha et al., "Comparative study of IgG binding to proteins G and A: Nonequilibrium kinetic and binding constant determination with the acoustic waveguide device," Anal Chem. 2003; 75:835-42.
Saison-Behmoaras, T. et al., "Short modified antisense oligonucleotides directed against ha-ras point mutations induce selective cleavage of the messenger RNA and inhibit T24 cell proliferation," *EMGO J.*, 1991; 10:1111-8.
Schipper, E.F. et al., "The Waveguide Mach-Zender Interferometer as Atrazine Sensor," *Analytical Chemistry.* 1998; 70:1192-7.
Schonfeld, D.L. et al., "Polarimetric assay for the medium-throuput determination of alpha-amino acid racemase activity," *Analytical Chemistry*, 76: 1184-1188 (2004).
Schuster, B. et al., "The Mechanism of Action of Phenylalanine Ammonia-Lyase—the Role of Prosthetic Dehydroalanine," *Proceedings of the National Academy of Sciences of the United States of America.* 1995; 92: 8433-7.
Shea, R.G. et al., "Synthesis, hybridization properties and antiviral activity of lipid-oligodeoxynucleotide conjugates," *Nucl. Acids Res.*, 8: 3777-3783 (1990).

Sidick et al., "Adaptive cross-correlation algorithm for extended scene Shack-Hartmann wavefront sensing," Optics Lett. 2008; 33:213-5.
Sjodahl et al., "Electronic speckle photography: analysis of an algorithm giving the displacement with subpixel accuracy," Applied Optics. 1993; 32:2278-84.
Sjodahl et al., "Measurement of shape by using projected random patterns and temporal digital speckle photography," Applied Optics. 1999; 38:1990-7.
Sjodahl, "Accuracy in electronic speckle photography," Applied Optics. 1997; 36:2875-85.
Sjodahl, "Electronic speckle photography: increased accuracy by nonintegral pixel shifting," Applied Optics. 1994; 33:6667-73.
Skoog et al. (2014) Fundamentals of Analytical Chemistry (Brooks/Cole, Belmont, CA) 9th Ed.
Sørensen, H.S., "Self Calibrating Interferometric Sensor," PhD thesis Riso-PhD-19(EN), Riso National Laboratory, Denmark, Jan. 2006, pp. 1-145 (163 pages).
Sørensen, H.S. et al., "Absolute refractive index determination by microinterferometric backscatter detection," *Analytical Chemistry*, 75: 1946-1953 (2003).
Sørenson, H.S. et al., "Highly sensitive biosensing based on interference from light scattering in capillary tubes," *Appl Phys Lett.* 2006; 89:151108-1 to -3.
Soumet, et al., "Identification by a multiplex PCR-based assay of *Salmonella typhimurium* and *Salmonella enteritidis* strains from environmental swabs of poultry houses," Lett Appl Microbiol. 1999; 29(1):1-6.
Speaker et al., "Characterization of a calmodulin-binding protein that is deficient in trifluoperazine-resistant variants of the macrophage-like cell line J774," Proc Natl Acad Sci USA. 1983; 80:329-33.
StClaire, J.C., "Heat Index Flow Monitoring in Capillaries with Interferometric Backscatter Detection," *Analytical Chemistry.* 2000; 72(19):4726-30.
Stenberg et al., Quantitative-Determination of Surface Concentration of Protein with Surface-Plasmon Resonance Using Radiolabeled Proteins. Journal of Colloid and Interface Science. 1991; 143(2):513-26.
STN Entry retrieved from STN Oct. 10, 2013 (1 page).
Stone, H.A. et al., Engineering Flows in Small Devices: Microfluidics Toward a Lab-on-a-Chip. Annu Rev Fluid Mech. 2004; 36:381-411.
Sulmann et al. (2014) Conformational Changes in Calcium-Sensor Proteins under Molecular Crowding Conditions. Chemistry 20 (22):6756-6762.
Sun et al. (1980) The Coil-Globule Transition—Radius of Gyration of Polystyrene in Cyclohexane. The Journal of Chemical Physics 73, 5971 73(12):5971-5975.
Supplementary European Search Report dated Feb. 10, 2006 for European Pat. App. No. 00959154.6 filed Aug. 17, 2000 (Applicant—Texas Tech Univeristy Health Sciences Center // Inventors—Bornhop et al. //) (4 pages).
Supplementary International Search Report dated Oct. 5, 2012 for US/PCT/2008/063879 filed May 16, 2008 and published as WO 2008/144496 on Nov. 27, 2008 (Applicant—Vanderbilt University // Inventors—Jones et al. //) (8 pages).
Supplementary International Search Report dated May 16, 2012 for PCT/US2005/38168 filed Oct. 24, 2005 and published as WO 2006/047408 on May 4, 2006 (Applicants—Vanderbilt University // Inventors—Bornhop et al. //) (6 pages).
Suzuki, et al., "Planar lipid bilayer reconstitution with a microfluidic system," *Lab Chip.* 2004; 4: 502-5.
Svanbro et al., Complex amplitude correlation for compensation of large in-plane motion in digital speckle pattern interferometry, Applied Optics. 2006; 45:8641-7.
Sviarchuk FP, et al., "Inhibition of HIV proliferation in MT-4 cells by antisense oligonucleotide conjugated to lipophilic groups,"*Biochimi.* 1993; 75(1-2):49-54.
Swinney K, et al., "A chip-scale universal detector for electrophoresis based on backscattering interferometry,"*Analyst.* 2000; 125:1713-7.
Swinney K, et al., "Capillary-Scale Polarimetry for Flowing Streams," *Analyst*, 126: 673-675 (2001).

(56) References Cited

OTHER PUBLICATIONS

Swinney K, et al., "Chip-Scale Universal Detection Based on Backscatter Interferometry," *Analytical Chem.* 2000; 72:2690-5.
Swinney K, et al., "D-beta-Hydroxybutrate Reaction Kinetics Studied in Nanoliter Volumes using a Capillary Polarimeter," Applied Spectroscopy, 54: 1458-1469 (2000).
Swinney K, et al., "Ion Analysis Using Capillary Electrophoresis with Refractive Index Detection," *Microchemical Journal*, 62: 154-163 (1999).
Swinney K, et al., "Laser-Based Capillary Polarimetry," *J. Capillary Electrophoresis and Microchip Technology*, 6: 93-96 (1999).
Swinney K, et al., "Micro-interferometric backscatter detection using a diode laser," *Analytica Chimica Acta*, 400: 265-280 (1999).
Swinney K, et al., Quantification and evaluation of Joule heating in on-chip capillary electrophoresis. *Electrophoresis*, 23:613-20 (2002).
Swinney K, et al., "Nanoliter Volume Polarimetry," Applied Spectroscopy, 56(1): 134-138 (2002).
Swinney K, et al., "Non-Invasive Picoliter Volume Thermometry Based on Backscatter Interferometry," *Electrohporesis*, 22: 2032-2036 (2001).
Swinney K, et al., "Ultrasmall volume refractive index detection using microinterferometry," *Review of Scientific Instruments*, 71: 2684-2692 (2000).
Swinney K, et al., "Universal Detection in Capillary Electrophoresis by Micro-Interferometric Backscatter,"*Analyst*, 124: 221-226 (1999).
Swinney K,e t al., "Universal Detection for Capillary Electrophoresis—Using Micro-Interferometric Backscatter Detection,"*J. MicroColumn Separation*, 11: 596-604 (1999).
Swinney, et la., "A Review of CE Detection Methodologies," *CRC Critical Reviews in Analytical Chemistry*, 30(1): 1-30.
Synnergren et al. "Optical in-plane strain field sensor," Applied Optics, vol. 41:1323-1329 (2002).
Synnergren et al., "Application of digital speckle photography to flash x-ray studies of internal deformation fields in impact experiments," Applied Optics, vol. 36:4030-4036 (1999).
Synnergren et al., "Digital speckle photography: visualization of mesoflow through clustered fiber networks," Applied Optics, vol. 41:1368-1373 (2002).
Takushima et al., "Optical reflectometry based on correlation detection and its application to the in-service monitoring of WDM passive optical network," Optics Express, vol. 15:5318-5326 (2007).
Tan AM, et al., "Rapid fabrication of microfluidic devices in poly(dimethylsiloxane) by photocopying," *Lab on a Chip*, 1: 7-9 (2001).
Tarigan H, et al., "Capillary-Scale Refractive Index Detection by Interferometric Backscatter," *Analytical Chemistry*, 68: 1762-1770 (1996).
Theze, et al., "Interleukin 2 and its receptors: recent advances and new immunological functions," *Immunology Today* 17:481-486 (1996).
Tsukamoto M, et al., "Recent advances in the measurement of enantiomeric excesses," *Advanced Synthesis & Catalysis*, 344: 453-463.
Tumolo et al. (2004) Determination of the refractive index increment (dn/dc) of molecule and macromolecule solutions by surface plasmon resonance. Anal Biochem 333(2):273-279.
Tzeng and Kalodimos (2011) Protein dynamics and allostery: an NMR view. Curr Opin Struc Struc Biol 21(1):62-67.
Török, "Calmodulin conformational changes in the activation of protein kinases," *Biochem Soc Trans* 30:55-61 (2002).
Urwyler, S. et al., Positive Allosteric Modulation of Native and Recombinant β-Amniobutyric AcidB receptors by 2,6-Di-tert-butyl-4-(3-hydroxy-2,2-dimethyl-propyl)-pheol (CGP7930) and Its Aldehyde Analog CGP13501. Mol Pharmacol. 2001; 60(5):963-71.
Van Delden RA et al., "Color indicators of molecular chirality based on doped liquid crystals," Angewandte Chemie—International Edition, 40: 3198 (2001).
Vandonselaar et al. (1994) Trifluoperazine-induced conformational change in Ca(2+)-calmodulin. Nat Struct Biol. 1(11):795-801.
Varma (2016) Article does not explain the origin of free-solution protein interaction signals, PNAS 113(34):E4930.
Velazquez-Campoy and Freire (2006) Isothermal titration calorimetry to determine association constants for high-affinity ligands. Nat Protoc 1(1): 186-191.
Veldhuis GJ, et al., "Highly-sensitive Passive Integrated Optical Spiral-Shaped Waveguide Refractometer," *Applied Physics Letters*, 71(20): 2895-2897 (1997).
Viola et al., "Alignment by maximization of mutual information", International Conference on Computer Vision (E. Grimson, S. Shafer, A. Blake and K. Sugihara, eds.), IEEE Computer Society Press, Los Alamitos, CA, pp. 16-23, 1995.
Vogelstein, et al., "Digital PCR,"*Proc Natl Acad Sci USA*, 96(16):9236-9241 (1999).
Volanthen M, et al., "Multiplexed optical fibre strain sensing using cross-correlation of subcarrier interferometric spectra," *Electronics Letters*, IEE Stevenage, GB, 32(3): 243-244 (1996).
Wang and Bornhop (2005) Dual-capillary backscatter interferometry for high-sensitivity nanoliter-volume refractive index detection with density gradient compensation. Anal Chem 77(24):7872-7877.
Wang et al., "Pseudophase information from the complex analytic signal of speckle fields and its applications. Part I: Microdisplacement observation based on phase-only correlation in the signal domain," Applied Optics, vol. 44:4909-4915 (2005).
Wang et al.,"Optical vortex metrology for nanometric speckle displacement measurement," Optics Express, vol. 14:120-127 (2006).
Wang Z, et al., "Attomole Sensitivity for Proteins and Polypeptides with On-chip CE and Universal Detection by Interferometric Backscatter," *Electrophoresis*, 24(5): 865-873 (2003).
Wang, et al., "High-speed digital-image correlation method," Optics Letters, vol. 34:1955-1957 (2009).
Watkins, "Scattering from side-illuminated clad glass fibers for determination of fiber parameters," *J Opt Soc Am*, 64:767-772 (1974).
Wetmur JG, et al., "DNA Probes: Applications of the Principles of Nucleic Acid Hybridization," *Crit. Rev. Biochem. Mol. Biol.*, 26: 227-259 (1991).
Whitesides et al., "Soft lithography in biology and biochemistry," *Annu Rev Biomed Eng*, 3:335-373 (2001).
Wienken et al. (2010) Protein-binding assays in biological liquids using microscale thermophoresis. Nat Commun. 1:100.
Wu ZY, et al., "Polymer microchips bonded by O-2-plasma activation," *Electrophoresis*, 23: 782-790 (2002).
Yamaguchi, "Fringe formation in speckle photography," J. Opt. Soc. Am. A, vol. 1:81-86 (1984).
Yanik, et al., "Development of a New Laser Based Polarimetric Detector and Its Application to High-performance Liquid Chromatography," PDR—Chiral, 1998.
Yeung, et al., "Electrochemistry-Based Real-Time PCR on a Microchip," Anal Chem, 80:363-368 (2008).
Ymeti, et al., "Realization of a multichannel integrated young interferometer chemical sensor," *Applied Optics*, 42: 5649-5660.
Young, et al., "Novel Recombinant-Antigen Enzyme Immunoassay for Serological Diagnosis of Syphilis," J Clin Microbio, 36(4):913-917 (1998).
Yu et al., "Energy landscape of aptamer/protein complexes studies by single-molecule force spectroscopy," Chem Asian J, 2:284-9 (2007).
Yu et al., "Interaction of an artificial antimicrobial peptide with lipid membranes,"*Biochemica et Biophysica Acta*, 1788: 333-344 (2009).
Zandonella C, "Cell nanotechnology: The tiny toolkit," *Nature*, 423: 10-12 (2003).
Zazopoulos E, et al., "A genomics-guided approach for discovering and expressing cryptic metabolic pathways," *Nature Biotech.*, 21: 187-190 (2003).
Zhang, W. et al., Microscale thermophoresis for the assessment of nuclear protein-binding affinities. Methods Mol Biol. 2014; 1094:269-76.
Zhang et al., "Proteins and cells on PEG immovilized silicon surfaces," *Biomaterials.* 2003; 19:953-60.
Zhao et al. (2011) On the Distribution of Protein Refractive Index Increments. Biophysical Journal 100(9):2309-2317.

(56) References Cited

OTHER PUBLICATIONS

Zhihong et al., "A new sandwich-type assay of estrogen using piezoelectric biosensor immobilized with estrogen response element," Anal Commun, 36:281-283 (1999).

Zhou J, et al., "Spectroscopic studies of substrate interactions with clavaminate synthase 2, a multifunctional a-KG-dependent non-heme iron enzyme: Correlation with mechanisms and reactivities," *J. Am. Chem. Soc.*, 123: 7388-7398(2001).

Zhou JM, et al., "Spectroscopic studies of substrates and cosubstrate binding to the a-ketoglutarate-dependent non-heme iron enzyme clavaminate synthase 2: correlation to reactivities and mechanisms," *Journal of Inorganic Biochemistry*, 74: 350-350 (1999).

Zhou JM, et al., "Substrate binding to the α-keoglutarate-dependent non-heme iron enzyme clavaminate synthase 2: Coupling mechanism of oxidative decarboxylation and hydroxylation," J. Am. Chem. Soc., 120: 13539-13540 (1998).

Preliminary Amendment dated Jun. 6, 2016 to the U.S. Patent and Trademark Office for U.S. Appl. No. 13/857,953, filed Apr. 5, 2013 and published as US 2013-0309661 A1 on Nov. 21, 2013 (Inventor—Darryl J. Bornhop et al.) (5 pages).

Non Final dated Aug. 11, 2016 by the U.S. Patent and Trademark Office for U.S. Appl. No. 13/857,953, filed Apr. 5, 2013 and published as US 2013-0309661 A1 on Nov. 21, 2013 (Inventor—Darryl J. Bornhop et al.) (15 pages).

Response to Non Final dated Dec. 5, 2016 to the U.S. Patent and Trademark Office for U.S. Appl. No. 13/857,953, filed Apr. 5, 2013 and published as US 2013-0309661 A1 on Nov. 21, 2013 (Inventor—Darryl J. Bornhop et al.) (8 pages).

Non Final dated Mar. 24, 2017 by the U.S. Patent and Trademark Office for U.S. Appl. No. 13/857,953, filed Apr. 5, 2013 and published as US 2013-0309661 A1 on Nov. 21, 2013 (Inventor—Darryl J. Bornhop et al.) (25 pages).

Non-Final Office Action dated Feb. 6, 2018 by the U.S. Patent and trademark Office for U.S. Appl. No. 15/199,417, filed Jun. 30, 2016 and published as US 2016/0327480 on Nov. 10, 2016 (Inventor—Bornhop et al.; Applicant—Vanderbilt University;) (12 pages).

Response to Non-Final Office Action filed on May 7, 2018 with the U.S. Patent and trademark Office for U.S. Appl. No. 15/199,417, filed Jun. 30, 2016 and published as US 2016/0327480 on Nov. 10, 2016 (Inventor—Bornhop et al.; Applicant—Vanderbilt University;) (17 pages).

Supplemental Amendment filed on Jun. 11, 2018 with the U.S. Patent and trademark Office for U.S. Appl. No. 15/199,417, filed Jun. 30, 2016 and published as US 2016/0327480 on Nov. 10, 2016 (Inventor—Bornhop et al.; Applicant—Vanderbilt University;) (12 pages).

Final Office Action dated Sep. 13, 2018 by the U.S. Patent and trademark Office for U.S. Appl. No. 15/199,417, filed Jun. 30, 2016 and published as US 2016/0327480 on Nov. 10, 2016 (Inventor—Bornhop et al.; Applicant—Vanderbilt University;) (5 pages).

Supplementary European Search Report dated Nov. 21, 2018 by the European Patent Office for Patent Application No. 1674080.7, which was filed on Jan. 22, 2016 and published as EP 3247988 on Nov. 29, 2017 (Inventor—Bornhop et al.; Applicant—Vanderbilt University;) (10 pages).

Kramer, M.N. et al., Longitudinal Pixel Averaging for Improved Compensation in Backscattering Interferometry. Opt Lett. 2018; 43(3):482-5.

Kramer, M.N. et al., A Highly Compensated Interferometer for Biochemical Analysis. ACS Sens. 2018; 3:1546-52.

Notice of Allowance dated Nov. 30, 2018 by the U.S. Patent and Trademark Office for U.S. Appl. No. 15/199,417, filed Jun. 30, 2016 and published as US 2016/0327480 on Nov. 10, 2016 (Inventor—Bornhop et al.; Applicant—Vanderbilt University;) (7 pages).

\* cited by examiner

Bound to Ca²⁺ and M13

Bound to Ca²⁺ and TFP

FREE-SOLUTION RESPONSE FUNCTION INTERFEROMETRY

CROSS-REFERENCE TO RELATED APPLICATIONS

This Application is a national stage filing under 35 U.S.C. § 371 of International Application No. PCT/US2017/015296, filed on Jan. 27, 2017, which claims the benefit of U.S. Provisional Application No. 62/288,926, filed on Jan. 29, 2016, the contents of which are incorporated herein by reference in their entireties.

ACKNOWLEDGEMENT

This invention was made with government support under Grant No. CHE 1307899 awarded by the National Science Foundation. The government has certain rights in the invention.

BACKGROUND

Contemporary assays have enabled single molecule detection (Betzig and Chichester (1993) Single Molecules Observed by near-Field Scanning Optical Microscopy. *Science* 262(5138):1422-1425; Levene et al. (2003) Zero-mode waveguides for single-molecule analysis at high concentrations. *Science* 299(5607):682-686) have accelerated the sequencing of the human genome (Anonymous (2001) Unsung Heroes. *Science* 291(5507):1207) and facilitated imaging with extraordinary resolution without labels (Hell S W & Wichmann J (1994) Breaking the Diffraction Resolution Limit by Stimulated-Emission—Stimulated-Emission-Depletion Fluorescence Microscopy. *Opt Lett* 19(11):780-782). To most closely study an interaction in the natural state, an assay would interrogate the processes (reaction, molecular interaction, protein folding event, etc.) without perturbation. Label-free chemical and biochemical investigations (Liedberg et al. (1995) Biosensing with Surface-Plasmon Resonance—How It All Started. *Biosens Bioelectron* 10(8):R1-R9; Yu et al. (2014) Shedding new light on lipid functions with CARS and SRS microscopy. *Bba-Mol Cell Biol L* 1841(8):1120-1129) transduce the desired signal without an exogenous label (fluorescent, radioactive, or otherwise) representing an essential step toward this goal. Many label-free methods require one of the interacting species to be either tethered or immobilized to the sensor surface, introducing a potential perturbation to the natural state of the species (Moreira et al. (2005).

However, back-scattering interferometry (BSI) is a free-solution label-free technique with the added benefit of sensitivity that rivals fluorescence (Bornhop et al. (2007) Free-solution, label-free molecular interactions studied by back-scattering interferometry. *Science* 317(5845):1732-1736). There are other techniques performed in free solution, such as mass spectrometry (MS) (Cubrilovic et al. (2014) Quantifying Protein-Ligand Binding Constants Using Electrospray Ionization Mass Spectrometry: A Systematic Binding Affinity Study of a Series of Hydrophobically Modified Trypsin Inhibitors. *J Am Soc Mass Spectr* 23(10):1768-1777; Kaltashov et al. (2012) Advances and challenges in analytical characterization of biotechnology products: Mass spectrometry-based approaches to study properties and behavior of protein therapeutics. *Biotechnol Adv* 30(1):210-222) and nuclear magnetic resonance (NMR) (Hu et al. (2004) The mode of action of centrin—Binding of Ca2+ and a peptide fragment of Karlp to the C-terminal domain. *J Biol Chem* 279(49):50895-50903; Tzeng and Kalodimos (2011) Protein dynamics and allostery: an NMR view. *Curr Opin Struc Biol* 21(1):62-67) and the widely used isothermal titration calorimetry (ITC) (Ababou and Ladbury (2007) Survey of the year 2005: literature on applications of isothermal titration calorimetry. *Journal of Molecular Recognition* 20(1):4-14; Liang, Y. (2006) Applications of isothermal titration calorimetry in protein folding and molecular recognition. *J Iran Chem Soc* 3(3):209-219). As with NMR, ITC has many advantages, but exhibits modest sensitivity and often requires large sample quantities. Another increasingly popular free-solution approach is micro-scale thermophoresis (MST). Yet, for MST to operate label-free, one of the binding partners must have a significant absorption/fluorescence cross-section (Wienken et al. (2010) Protein-binding assays in biological liquids using microscale thermophoresis. *Nat Commun* 1; Zhang et al. (2014) Microscale thermophoresis for the assessment of nuclear protein-binding affinities. *Methods Mol Biol* 1094:269-276). BSI represents an attractive alternative to these methods because of its high sensitivity, small sample volume requirement, optical simplicity and broad applicability (Baksh et al. (2011) Label-free quantification of membrane-ligand interactions using backscattering interferometry. *Nat Biotechnol* 29(4):357-360; Kussrow et al. (2012) Interferometric Methods for Label-Free Molecular Interaction Studies. *Anal Chem* 84(2):779-792; Olmsted et al. (2014) Toward Rapid, High-Sensitivity, Volume-Constrained Biomarker Quantification and Validation using Backscattering Interferometry. *Anal Chem* 86(15):7566-7574; Saetear et al. (2015) Quantification of Plasmodium-host protein interactions on intact, unmodified erythrocytes by back-scattering interferometry. *Malaria J* 14). Whereas ITC and MST have well known or established theoretical descriptions, the fundamental mechanistic basis for the signal observed in BSI is less well understood.

Accordingly, there remains a need in the art for systems and methods for free-solution, label-free detection of intermolecular interactions between analytes, preferably with low detection limits and/or low sample volume requirements.

SUMMARY

As embodied and broadly described herein, the invention, in one aspect, relates to free-solution analytical methods for use in the detection of molecular interactions between non-immobilized analytes and/or characteristic properties of a sample.

Disclosed are free-solution analytical methods comprising detecting molecular interactions between a first non-immobilized analyte and a second non-immobilized analyte, wherein the detection is performed by refractive index sensing other than backscattering interferometry or by circular dichroism.

Also disclosed are free-solution analytical methods comprising the steps of: (a) providing a refractive index sensor for reception of a fluid sample to be analyzed; (b) introducing a first sample comprising a first non-immobilized analyte to be analyzed and a second sample comprising a second non-immobilized analyte to be analyzed onto the sensor, wherein the first analyte is allowed to interact with the second analyte; (c) interrogating the fluid sample with light; (d) detecting the light after interaction with the fluid sample, wherein the detected light is not backscattered; and (e) detecting a molecular interaction between the first and second analyte.

Also disclosed are free-solution analytical methods comprising detecting molecular interactions between a first non-immobilized analyte and a second non-immobilized analyte, wherein the determination comprises determining the degree of polymerization, protein folding, protein aggregation, blood oxygenation, the conformational state of an ion channel or membrane protein, or the hydration state of an ion channel or membrane protein, and wherein the determination is performed by refractive index sensing.

Also disclosed are free-solution analytical methods comprising determining the degree of polymerization, protein folding, protein aggregation, blood oxygenation, the conformational state of an ion channel or membrane protein, or the hydration state of an ion channel or membrane protein, and wherein the determination is performed by refractive index sensing.

Also disclosed are systems comprising a refractive index sensor for detecting molecular interactions between a first non-immobilized analyte and a second non-immobilized analyte, and a pressure change compensator.

Also disclosed are free-solution analytical methods comprising detecting a molecular change, wherein the detection is performed by refractive index sensing other than back-scattering interferometry.

Unless otherwise expressly stated, it is in no way intended that any method or aspect set forth herein be construed as requiring that its steps be performed in a specific order. Accordingly, where a disclosed method or system does not specifically state that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

BRIEF DESCRIPTION OF THE FIGURES

The accompanying figures, which are incorporated in and constitute a part of this specification, illustrate several aspects and together with the description serve to explain the principles of the invention.

FIG. 4A shows a representative CD spectra of the DNA duplex (inset shows the A-form to B-form transition monitored at 270 nm by ellipticity). FIG. 4B shows a representative correlation for BSI signal and ellipticity.

FIG. 11A shows a representative image of ten parallel rays impinged on a chip from the right that are allowed to refract and reflect and exit to the right and interfering. FIG. 11B shows a representative image of a many beam optical ray trace of a semicircular channel in a microfluidic chip.

FIG. 16A shows a representative image of a hand-held Reichert RI Detector. FIG. 16B shows representative data illustrating the response of a hand-held RI detector for glycerol calibration standards. FIG. 16C shows representative data illustrating label-free, free-solution detection of Cyfra 21-1 in PBS using a hand-held RI detector. FIG. 16D shows representative data illustrating the comparison of signal at 50 ng/mL using a hand-held RI detector and a BSI detector.

Figure 1A:
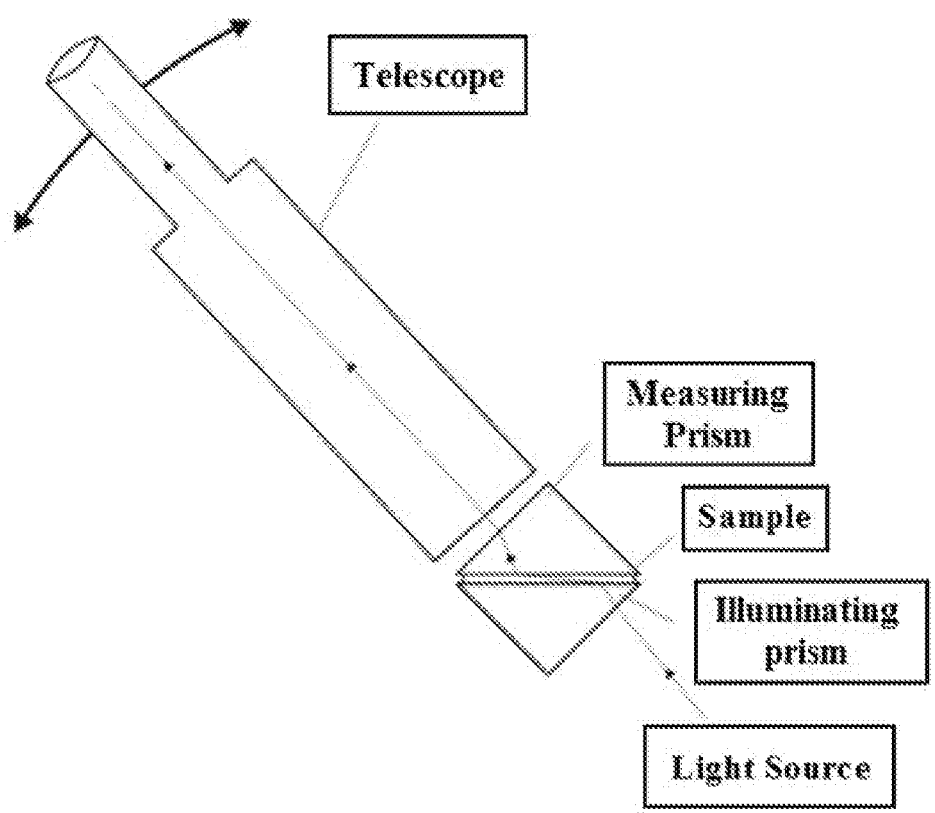
FIG. 1A and FIG. 1B show representative block diagrams of a refractometer (1A) and a forward scattering interferometer (1B).

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which may need to be independently confirmed.

A. Definitions

As used in the specification and the appended claims, the singular forms "a," "an" and "the" include plural referents unless the context clearly dictates otherwise. Thus, for example, reference to "a substrate," "a polymer," or "a sample" includes mixtures of two or more such substrates, polymers, or samples, and the like.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the terms "optional" or "optionally" means that the subsequently described event or circumstance may or may not occur, and that the description includes instances where the event or circumstance occurs and instances where it does not.

As used herein, the term "polymer" refers to a relatively high molecular weight organic compound, natural or synthetic (e.g., polyethylene, rubber, cellulose), whose structure can be represented by a repeated small unit, the monomer (e.g., ethane, isoprene, β-glucose). Synthetic polymers are typically formed by addition or condensation polymerization of monomers.

As used herein, the term "copolymer" refers to a polymer formed from two or more different repeating units (monomer residues). By way of example and without limitation, a copolymer can be an alternating copolymer, a random copolymer, a block copolymer, or a graft copolymer.

As used herein, the term "bioassay" refers to a procedure for determining the concentration, purity, and/or biological activity of a substance.

As used herein, the term "chemical event" refers to a change in a physical or chemical property of an analyte in a sample that can be detected by the disclosed systems and methods. For example, a change in refractive index (RI), solute concentration and/or temperature can be a chemical event. As a further example, a biochemical binding or association (e.g., DNA hybridization) between two chemical or biological species can be a chemical event. That is, a chemical event can be the formation of one or more interaction products of the interaction of a first analyte with a second analyte. As a further example, a disassociation of a complex or molecule can also be detected as an RI change. As a further example, a change in temperature, concentration, and association/dissociation can be observed as a function of time. As a further example, bioassays can be performed and can be used to observe a chemical event.

As used herein, the terms "equilibrium constant" and "Kc" and "Keq" refer to the ratio of concentrations when equilibrium is reached in a reversible reaction. For example, for a general reaction given by the equation:

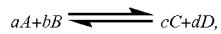

$$aA + bB \rightleftharpoons cC + dD,$$

the equilibrium constant can be expressed by:

$$K_c = \frac{[C]^c[D]^d}{[A]^a[B]^b}.$$

An equilibrium constant can be temperature- and pressure-dependent but has the same value, irrespective of the amounts of A, B, C, and D. A specific type of equilibrium constant that measures the propensity of a larger object to separate (dissociate) reversibly into smaller components is a "dissociation constant" or "Kd." A dissociation constant is the inverse of an "affinity constant."

As used herein, the term "dissociation rate" is a concentration dependent quantity and involves the "dissociation rate constant" or "$K_D$." The dissociation rate constant relates the rate at which molecules dissociate to the concentration of the molecules. A dissociation can be described as AB→A+B, and the rate of dissociation (dissociation rate) is equal to $K_D$[AB]. In general, the larger the value of $K_D$, the faster the inherent rate of dissociation.

As used herein, the term "association rate" is a concentration dependent quantity and involves the "association rate constant" or "$K_A$." The association rate constant relates the rate at which molecules associate to the concentration of the molecules. An association can be described as A+B→AB, and the rate of association (association rate) is equal to $K_A[A][B]$. In general, the larger the value of $K_A$, the faster the inherent rate of association.

As used herein, the term "free-solution" refers to a lack of surface immobilization. The term is not meant to exclude the possibility that one or more molecules or atoms of analyte may associate with a surface. Rather, the term can describe the detection of an analyte without the requirement for surface immobilization during analysis.

As used herein, the terms "label-free" and "unlabeled" describe a detection method wherein the detectability of an analyte is not dependent upon the presence or absence of a detectable label. For example, "label-free" can refer to the lack of a detectable label. It is understood that the ability of a label to be detected can be dependent upon the detection method. That is, an analyte having a moiety capable of serving as a detectable label for a first detection method can be considered "label-free" or "unlabeled" when a second detection method (wherein the label is not detectable) is employed. In a further aspect, the analytes employed in the disclosed systems and methods can lack detectable labels.

As used herein, the term "detectable label" refers to any moiety that can be selectively detected in a screening assay. Examples include without limitation, radiolabels (e.g., $^3$H, $^{14}$C, $^{35}$S, $^{125}$I, $^{131}$I) affinity tags (e.g. biotin/avidin or streptavidin), metal binding domains, epitope tags, FLASH binding domains (see U.S. Pat. Nos. 6,451,569; 6,054,271; 6,008,378 and 5,932,474), glutathione or maltose binding domains, photometric absorbing moieties, fluorescent or luminescent moieties (e.g. fluorescein and derivatives, GFP, rhodamine and derivatives, lanthanides etc.), and enzymatic moieties (e.g. horseradish peroxidase, β-galactosidase, β-lactamase, luciferase, alkaline phosphatase). Such detectable labels can be formed in situ, for example, through use of an unlabeled primary antibody which can be detected by a secondary antibody having an attached detectable label. Further examples include imaging agents such as radioconjugate, cytotoxin, cytokine, Gadolinium-DTPA, a quantum dot, iron oxide, and manganese oxide.

Disclosed are the components to be used to prepare the compositions of the invention as well as the compositions themselves to be used within the methods disclosed herein. These and other materials are disclosed herein, and it is understood that when combinations, subsets, interactions, groups, etc., of these materials are disclosed that while specific reference of each various individual and collective combinations and permutation of these compounds may not be explicitly disclosed, each is specifically contemplated and described herein. For example, if a particular compound is disclosed and discussed and a number of modifications that can be made to a number of molecules including the compound are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific aspect or combination of aspects of the methods of the invention.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

B. Refractive Sensing

In one aspect, disclosed are systems comprising a refractive index sensor for detecting molecular interactions between a first non-immobilized analyte and a second non-immobilized analyte, and a pressure change compensator. In a further aspect, both analytes are unlabeled. In a still further aspect, at least one of the analytes is present in an amount of less than about $1.0 \times 10^{-3}$ M.

In various aspects, refractive sensing refers to the measurement of the refractive index of a sample, for example, a fluid sample. The refractive index or change in refractive index of a sample can be used to determine a variety of biologically important measurements including, but not limited to, an equilibrium constant, a dissociation constant, a dissociation rate, an association rate, a concentration of an analyte, and the presence of an analyte. Refractive index measurements are also used in other applications such as, for example, process control and the detection of explosives (Bowen et al. (2003) "Gas phase detection of trinitrotoluene utilizing a solid-phase antibody immobilized on a gold film by means of surface plasmon resonance spectroscopy" *Appl. Spectrosc.* 57(8): 906-914).

Various devices and techniques for measuring refractive index are known. These include the Abbe-type refractometer (see FIG. 1A), and sensors based on surface plasmon resonance. Optical waveguides can also be used. The presence of a liquid adjacent to an optical waveguide can alter the effective modal index of light propagating within the waveguide. This modification of index can be measured using techniques that are sensitive to changes in optical path length. For example, interferometer structures have been used to measure index changes and hence to sense the presence of proteins (Heideman et al. (1993) "Performance of a highly sensitive optical wave-guide Mach-Zehnder interferometer immunosensor" *Sensors and Actuators B-Chemical* 10(3): 209-217) (see FIG. 1B).

Referring to FIG. 1A, a block diagram of an exemplary Abbe-type refractometer is illustrated. As shown, the sample is contained between two prisms, the illuminating prism and the measuring prism. The light source generates light, which enters the sample from the illuminating prism. The surface of the illuminating prism is matted, so that light enters the sample at all possible angles, including those almost parallel to the surface. The light is then refracted at the critical angle at the bottom surface of the measuring prism and directed into the telescope. Additionally, two Amici prisms that can be rotated are located within the telescope (not shown), which can be used to correct the dispersion. The telescope is used to measure the position of the border between dark and light areas. Knowing the angle and refractive index of the measurement prism allows for the refractive index of the sample to be calculated.

Figure 1B:
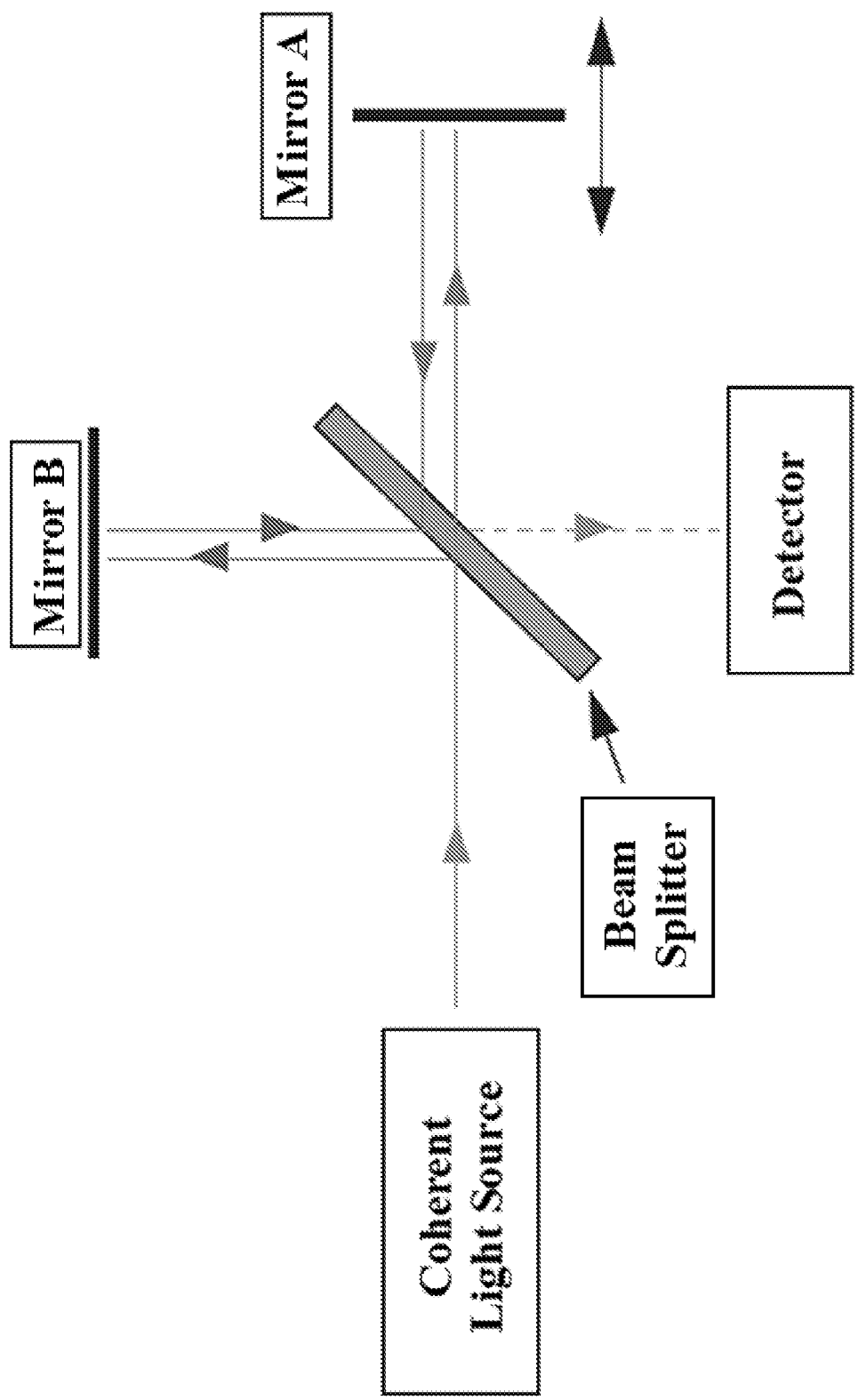

Referring to FIG. 1B, a block diagram of an exemplary Michelson interferometer is illustrated. As shown, a coherent light source emits light that hits a beam splitter. A portion of the light is transmitted directly through beam splitter to mirror A, while some is reflected in the direction of mirror B. Both beams are then reflected back onto the beam splitter to produce an interference pattern incident on the detector. If an angle is observed between the two returning beams the detector will record a sinusoidal fringe pattern. Alternatively, if there is perfect spatial alignment between the two returning beams, the detector will record a constant intensity over the beam dependent on the differential path length.

Accordingly, the disclosed invention provides a method for detecting molecular interactions between a first non-immobilized analyte and a second non-immobilized analyte, wherein the detection is performed by refractive index sensing other than backscattering interferometry. Examples of refractive index (RI) detectors include, but are not limited to, RI detectors based on the angle of deviation method of measurement, RI detectors based on the Fresnel method of RI measurement, a Christiansen effect detector, an interferometer detector, or a differential refractometer detector. Additional examples include a refractomax 521 RI detector, a RID-20A RI detector, a RID-10A RI detector, a Waters RI detector, a Waters RI detector, a Wyatt RI detector, a HPLC, an Acquity RI detector, a 1260 Infinity RI detector, an Optilab RI detector, a Knauer RI detector, a Shimadzu RI detector, a Shodex RI detector, a LC-4000 Series RI detector, or other suitably sensitive RI detectors.

In a further aspect, detection is performed by refractive index sensing other than forward scattering or side scattering interferometry.

In various aspects, the first and/or second analyte may be contained in, e.g. flowed through, a capillary dimensioned flow channel such as a capillary tube. The cross-sectional depth of the channel is limited only by the coherence length of the light and its breadth is limited only by the width of the light beam. Preferably, the depth of the channel is from 1 to 10 µm, but it may be from 1 to 20 µm or up to 50 µm or more, e.g. up to 1 mm or more. However, sizes of up to 5 mm or 10 mm or more are possible. Suitably, the breadth of the channel is from 0.5 to 2 times its depth, e.g., equal to its depth. In various aspects, the channel may comprise a substantially circular, generally semi-circular, or rectangular cross-section.

The sample is typically a liquid, and can be flowing or stationary. However, the sample can also be a solid or a gas in various aspects of the present invention. The first and/or further materials will normally be solid but in principle can be liquid, e.g., can be formed by a sheathing flow of guidance liquid(s) in a microfluidic device, with the sample being sheathed flow of liquid between such guidance flows. The sample may also be contained in a flow channel of appropriate dimensions in substrate such as a microfluidic chip. The method may therefore be employed to obtain a read out of the result of a reaction conducted on a "lab on a chip" type of device.

The invention includes apparatus for use in performing a method as described, which apparatus comprises a source of spatially coherent light, a sample holder for receiving a sample upon which to perform the method positioned in a light path from the light source, a detector for detecting light, and data processing means for receiving measurements of light intensity from the detector and for conducting an analysis thereon, wherein the analysis comprised determining an equilibrium constant, a dissociation constant, a dissociation rate an association rate, calculating a change in hydrodynamic volume, entropy, or enthalpy, the concentration of the first and/or second analyte, identifying the presence of the first and/or second analyte, or identifying the presence of a third analyte. In various aspects, the analysis comprises quantification of the sample.

In a further aspect, the RI sensor comprises a channel formed in a substrate, the channel has a longitudinal direction and a transverse direction, and a light source for generating a light, wherein the light is elongated in the longitudinal direction of the channel In various aspects, the channel of the present invention can be formed from a substrate such as a piece of silica or other suitable optically transmissive material. In various aspects, the material of composition of the substrate has a different index of refraction than that of the sample to be analyzed. In a further aspect, as refractive index can vary significantly with temperature, the substrate can optionally be mounted and/or connected to a temperature control device. In a still further aspect, the substrate can be tilted, for example, about 7°, such that scattered light from channel can be directed to a detector.

In a further aspect, the channel has a generally semi-circular cross-sectional shape. A unique multi-pass optical configuration is inherently created by the channel characteristics, and is based on the interaction of the unfocused laser beam and the curved surface of the channel that allows interferometric measurements in small volumes at high sensitivity. Alternatively, the channel can have a substantially circular or generally rectangular cross-sectional shape. In a still further aspect, the substrate and channel together comprise a capillary tube. In yet a further aspect, the substrate and channel together comprise a microfluidic device, for example, a silica substrate, or a polymeric substrate [e.g., polydimethylsiloxane (PDMS) or polymethyl methacrylate (PMMA)], and an etched channel formed in the substrate for reception of a sample, the channel having a cross sectional shape. In an even further aspect, the cross sectional shape of a channel is semi-circular. In a still further aspect, the cross sectional shape of a channel is square, rectangular, or elliptical. In yet a further aspect, the cross sectional shape of a channel can comprise any shape suitable for use in a BSI technique. In an even further aspect, a substrate can comprise one or multiple channels of the same or varying dimensions. In various aspects, the channel can have a radius of from about 5 to about 250 micrometers, for example, about 5, 10, 20, 30, 40, 50, 75, 100, 150, 200, or 250 micrometers. In still other aspects, the channel can have a radius of up to about 1 millimeter or larger, such as, for example, 0.5 millimeters, 0.75 millimeters, 1 millimeter, 1.25 millimeters, 1.5 millimeters, 1.75 millimeters, 2 millimeters, or more.

In various aspects, the source of coherent light is a laser, suitably a He—Ne laser or a diode laser or VCSEL. The laser light may be coupled to the site of measurement by known wave-guiding techniques or may be conventionally directed to the measurement site by free space transmission.

In various aspects, the detected light is representative of the refractive index of the sample. The measured refractive index can be indicative of a number of properties of the sample including, but not limited to, the presence or concentration of a solute substance, e.g., a reaction product, pressure, temperature, or flow rate (e.g., by determining when a thermal perturbation in a liquid flow reaches a detector).

In one aspect, the detector is a CCD array of suitable resolution.

The apparatus can comprise means for controlling the temperature of the sample, e.g., a heater and/or a Peltier cooler and a temperature measuring device.

The invention includes apparatus as described herein, wherein the sample holder is configured to allow a sample to flow there through and wherein the sample holder is connected to receive a separated sample from a sample separation device in which components of a mixed sample are separated, e.g., by capillary electrophoresis, capillary electrochromatography, or HPLC. Accordingly, viewed from another perspective, the invention provides chromatography apparatus having a refractive index measuring unit as described herein as a detector.

More generally, the sample holder of the apparatus described above can be a flow through passage so that the contents of the channel may be continuously monitored to observe changes in the content thereof. These changes may include the temporary presence of cells and the out flow from the sample holder may be diverted to a selected one of two or more outlet channels according to the measurements of refractive index observed in the sample holder, e.g., to achieve sorting of cells in response to such measurements. The sample holder can contain a stationary analytical reagent (e.g., a coating of an antibody, oligonucleotide, or other selective binding agent) and changes in the refractive index caused by the binding of a binding partner to the reagent may be observed. In view of the small sample size which it is possible to observe, the sample holder can contain a biological cell and metabolic changes therein may be observed as changes in the refractive index of the cell.

Thus, in various aspects, the sample solution and the reference solution may be picked up individually into a cell such as, for example, a capillary tube. Each sample is then loaded into a tray for reading. In a further aspect, the tray can have several cells (e.g., capillaries) integrated into it. In this way, the samples are delivered to the individual cells for introduction into the sensor for analysis.

In one aspect, the invention relates to a method for detecting molecular interactions between a first non-immobilized analyte and a second non-immobilized analyte, wherein the detection is performed by refractive index sensing other than backscattering interferometry, wherein the detection comprises determining refractive index variations in the intensity of reflections of light which has passed through the first and second analyte. In a further aspect, detection is performed by refractive index sensing other than forward scattering or side scattering interferometry.

Refractive index can be negatively affected by changes in pressure. Moreover, as the concentration of the analyte decreases, even smaller changes in pressure can have a significantly greater impact. Thus, in various aspects, the system may comprise a pressure change compensator. A pressure change compensator can balance the pressure inside and outside of the detection system by compensating for variations in the volume of the liquid within the system, which may be due to variations in the ambient pressure and/or temperature. Examples of pressure compensators include, but are not limited to, a back-pressure restrictor and a capillary restrictor.

A change in environmental temperature can also negatively impact a RI detector. Thus, in various aspects, the system may comprise a temperature change compensator. A temperature change compensator can balance the temperature inside and outside of the detection system by compensating for variations in the temperature of the liquid within the system, which may be due to, for example, variations in the ambient pressure and/or temperature. Alternatively, the temperature change compensator can change the temperature of the incoming mobile phase to match that of the solvent in the detector. Examples of temperature compensators include, but are not limited to, a thermostat cabinet, a thermoelectric temperature controller (e.g., Peltier) and a heat exchanger.

C. Circular Dichroism

Circular dichroism (CD) is the difference in the absorption of left-handed circularly polarized light (L-CPL) and right-handed circularly polarized light (R-CPL) and occurs when a molecule contains one or more chiral chromophores (light-absorbing groups). CD has a wide range of applications including, but not limited to, analyzing the structure of small molecules, DNA, peptides, nucleic acids, carbohydrates, and proteins, identifying charge-transfer transitions, determining geometric and electronic structure, and analyzing molecular interactions. CD spectra are measured using a circular dichroism spectrometer (see FIG. 2).

Accordingly, the disclosed invention provides a method for detecting molecular interactions between a first non-immobilized analyte and a second non-immobilized analyte, wherein the detection is performed by circular dichroism.

Figure 2:
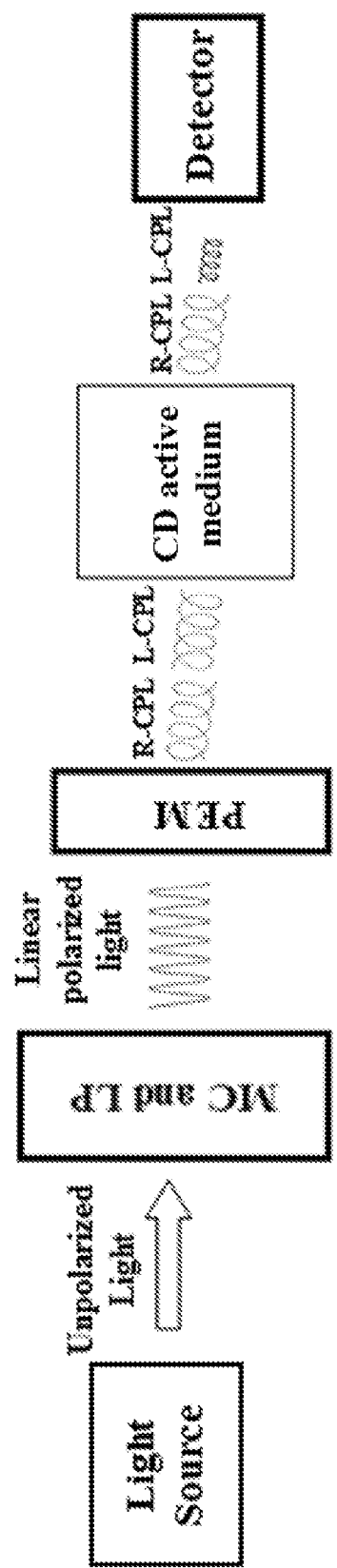
FIG. 2 shows a representative block diagram of a circular dichroism spectrometer.

Referring to FIG. 2, a block diagram of an exemplary CD spectrometer is illustrated. As shown, the light source emits light that hits the monochromator (MC). A narrow band of wavelengths then pass through the linear polarizer (LP), which splits the unpolarized monochromatic beam into two linearly polarized beams. Next, one of the two linearly polarized beams passes through the photoelastic modulator (PEM), which consists of a plate made of a transparent, optically isotropic material bonded to a piezoelectric quartz crystal. When an alternating electric field is applied, the light emerging from the PEM switches from L-CPL to R-CPL and back with the frequency of the applied electric field. If the sample exhibits CD, the amount of light absorbed varies periodically with the polarization of the incident light. This, in turn, causes the intensity of the light that reaches the detector to exhibit sinusoidal intensity variations at the frequency of the field applied. Thus, the detector output consists of a signal with a small alternating current (AC) component superimposed on a direct current (DC) component. The AC component is filtered out and amplified. The ratio of the AC to the DC component is directly proportional to the circular dichroism of the sample, and this quantity is recorded as a function of wavelength to provide a CD spectrum.

D. Methods for Free-Solution Determination of Molecular Interactions

In contrast to conventional techniques that observe immobilized analytes—which necessarily limit conformational and translational freedom for analytes and are, thus, in vitro measurements—free-solution analysis techniques mimic in vivo measurements, because analytes enjoy unrestricted freedom in all three dimensions during measurement.

In one aspect, disclosed are free-solution analytical methods comprising detecting molecular interactions between a first non-immobilized analyte and a second non-immobilized analyte, wherein the detection is performed by refractive index sensing other than backscattering interferometry or by circular dichroism. In a further aspect, detection is performed by refractive index sensing other than forward scattering or side scattering interferometry.

In one aspect, disclosed are free-solution analytical methods comprising the steps of: (a) providing a refractive index sensor for reception of a fluid sample to be analyzed; (b) introducing a first sample comprising a first non-immobilized analyte to be analyzed and a second sample comprising a second non-immobilized analyte to be analyzed onto the sensor, wherein the first analyte is allowed to interact with the second analyte; (c) interrogating the fluid sample with light; (d) detecting the light after interaction with the fluid sample, wherein the detected light is not backscattered; and (e) detecting a molecular interaction between the first and second analyte.

In one aspect, disclosed are free-solution analytical methods comprising detecting molecular interactions between a first non-immobilized analyte and a second non-immobilized analyte, wherein the determination comprises determining the degree of polymerization, protein folding, protein aggregation, blood oxygenation, the conformational state of an ion channel or membrane protein, or the hydration state of an ion channel or membrane protein, and wherein the determination is performed by refractive index sensing. In a further aspect, the method comprises the steps of: (a) providing a refractive index sensor for reception of a fluid sample to be analyzed; (b) introducing a first sample comprising a first non-immobilized analyte to be analyzed and a second sample comprising a second non-immobilized analyte to be analyzed onto the sensor, wherein the first analyte is allowed to interact with the second analyte to form one or more interaction products; (c) interrogating the fluid sample with light; (d) detecting the deflected and/or refracted light after interaction with the fluid sample, wherein the light is not backscattered; and (e) detecting a molecular interaction between the first and second analyte.

In one aspect, disclosed are free-solution analytical methods comprising determining the degree of polymerization, protein folding, protein aggregation, blood oxygenation, the conformational state of an ion channel or membrane protein, or the hydration state of an ion channel or membrane protein, and wherein the determination is performed by refractive index sensing. In a further asepct, refractive index sensing is not via backscattering interferometry.

In a further aspect, the light is not scattered.

In a further aspect, refractive index sensing is via a refractometer. In a still further aspect, refractive index sensing is via interferometry. In yet a further aspect, refractive index sensing is via forward scattering interferometry. In an even further aspect, refractive index sensing is via backscattering interferometry. In a still further aspect, refractive index sensing is via a hand-held refractive index sensing device.

It is contemplated that the method can be used to determine, for example, one or more of an equilibrium constant, a dissociation constant, a dissociation rate, a dissociation rate constant, an association rate, and/or an association rate constant of the interaction. In a further aspect, the method can be used to determine, for example, the concentration of the first and/or second analyte. In a still further aspect, the method can be used to determine, for example, the presence of the first and/or second analyte. In yet a further aspect, the method can be used to determine, for example, the presence of a third analyte.

Each of the one or more analytes can be introduced onto the sensor in a sample. Two or more analytes can be present in the same or in different samples. Each of the one or more analytes can independently be present in a suitable concentration, for example, a concentration of less than about $5.0 \times 10^{-4}$ M, of less than about $1.0 \times 10^{-4}$ M, of less than about $5.0 \times 10^{-5}$ M, of less than about $1.0 \times 10^{-5}$ M, of less than about $5.0 \times 10^{-6}$ M, of less than about $1.0 \times 10^{-6}$ M, of less than about $5.0 \times 10^{-7}$ M, of less than about $1.0 \times 10^{-7}$ M, a concentration of less than about $5.0 \times 10^{-8}$ M, of less than about $1.0 \times 10^{-8}$ M, of less than about $5.0 \times 10^{-9}$ M, of less than about $1.0 \times 10^{-9}$ M, of less than about $1.0 \times 10^{-10}$ M, of less than about $5.0 \times 10^{-10}$ M of less than about $5.0 \times 10^{-11}$ M, of less than about $1.0 \times 10^{-11}$ M, of less than about $5.0 \times 10^{-12}$ M, of less than about $1.0 \times 10^{-12}$ M, of less than about $5.0 \times 10^{-13}$ M, of less than about $1.0 \times 10^{-13}$ M, of less than about $5.0 \times 10^{-14}$ M, of less than about $1.0 \times 10^{-14}$ M, of less than about $5.0 \times 10^{-15}$ M, or of less than about $1.0 \times 10^{-15}$ M.

In one aspect, the interaction can be a biomolecular interaction. For example, two analytes can associate to provide an interaction product (e.g., adduct, complex, or new compound). In a still further aspect, an analyte can dissociate to provide two or more interaction products. In yet a further aspect, more than two analytes can be involved in the interaction.

In a further aspect, the first and/or second analyte is a complex. In a still further aspect, the complex is a chemical or biochemical complex. In yet a further aspect, the complex was formed prior to the introducing step. In an even further aspect, the complex was formed subsequent to the introducing step.

The disclosed techniques can determine the interaction between one or more analytes by monitoring, measuring, and/or detecting the formation and/or steady state relative abundance of one or more analyte interaction products from the interaction of the one or more analytes. The determination can be performed qualitatively or quantitatively. Interaction rate information can be derived from various measurements of the interaction.

In a further aspect, the first sample is combined with the second sample prior to introduction. That is, the analytes are combined (and potentially interacting) prior to performing the disclosed methods. In this aspect, the step of introducing the first sample and the step of introducing the second sample are performed simultaneously.

In a further aspect, the first sample is combined with the second sample after introduction. That is, the analytes can be combined at a point before the sensor, or at a point on the sensor, when performing the disclosed methods. In this aspect, the step of introducing the first analyte and the step of introducing the second analyte are performed either simultaneously or sequentially. In a further aspect, the detecting step is performed during the interaction of the first analyte with the second analyte.

Thus, in various aspects, the first and second samples are introduced simultaneously. In a further aspect, the first and second samples are introduced sequentially. In a still further aspect, the first analyte is allowed to interact with the second analyte prior to introducing the first and/or second sample onto the sensor. In yet a further aspect, the first analyte is allowed to interact with the second analyte after introducing the first and/or second sample onto the sensor. In an even further aspect, the first analyte is allowed to interact with the second act while introducing the first and/or second sample onto the sensor.

A first sample (e.g., a solution including a first non-immobilized analyte to be analyzed) can be introduced onto the refractive index sensor. The first sample can be provided having a known concentration of the first analyte. A baseline response can then be established by directing light onto the first sample.

A second sample (e.g., a solution including a second non-immobilized analyte to be analyzed) can then be introduced onto the refractive index sensor. In various aspects, the second sample can be provided as a pre-mixed sample of the first non-immobilized analyte and the second non-immobilized analyte or provided by adding a sample comprising the second non-immobilized analyte to the first sample. In one aspect, the first sample is a solution of the first analyte, which is displaced on the sensor by the introduction of the second sample, which is a solution of both the first analyte and the second analyte. The second sample can be provided having a known concentration of the first analyte, which can be the same as the concentration of the first analyte in the first solution. The second sample can also be provided having a known concentration of the second analyte. Light can then be directed onto the sensor.

Figure 3:
FIG. 3 shows a representative diagram of exemplary reference and sample contents.

In various aspects, a reference sample can be introduced onto the refractive index sensor. The reference sample can be introduced onto the refractive index sensor prior to or subsequent to introduction of the first and/or second sample. In a further aspect, the reference sample comprises a first non-immobilized analyte to be analyzed. In a still further aspect, the method further comprises the steps of: (a) interrogating the reference sample with light; (b) detecting the light after interaction with the reference sample, wherein the detected light is not backscattered; (c) determining a characteristic of the reference sample; and (e) employing the characteristic of the reference sample to compensate for background interference effects in the determination of the molecular interaction between the first and second analyte. Exemplary reference samples are illustrated in FIG. 3.

In various aspects, the reference sample can be a ligand alone in the absence of the matrix, more often referred to as a blank. Reference samples are typically comprised of the ligand in the experimental matrix (cell vesicle, cell lysate, serum, urine, other biofluids, etc.) that does not contain the receptor. Examples include, but are not limited to, cell-based matrices that do not contain the receptor, null lipoparticles (devoid of the target receptor), empty viral particle/bacteriophage scaffolds, and an experimental matrix stripped of receptor.

In various aspects, the reference sample can be the experimental matrix containing the receptor with a nonbinding analyte molecule that is similar to the ligand. Examples include, but are not limited to, a denatured ligand, an isotype matched antibody for a different compound, a compound with a similar structural backbone as the ligand that has additional or removed functional groups (e.g., phenol versus 2,4,6-trinitrophenol, dopamine versus 3-methoxytyramine, tyrosine versus 3-nitrotyrosine, serotonin versus tryptophan, histamine versus histidine), a nonsense nucleic acid strand of the same length, a nucleic acid stand with >3 base-pair mismatch, a compound of similar size as the ligand known to not bind the receptor, and other molecules known to non-specifically bind to the matrix (e.g., cholesterol for membrane based experiments).

In various aspects, the reference sample can be the ligand with the experimental matrix containing the receptor (cell-based matrices, tissues-based matrices, serum, urine, other biofluids, etc.) that has been treated to inhibit binding. Examples include, but are not limited to, enzyme treatment of the receptor, blocking of the receptor with an antibody, blocking of the receptor with a known binding compound, blocking of the receptor with an inhibitor, denaturation of the receptor, receptor without the cofactors necessary for binding, (e.g., calmodulin without $Ca^{2+}$, concanavalin A without $Mn^{2+}$ and $Ca^{2+}$, recoverin without $Ca^{2+}$, etc.).

In a further aspect, the first analyte and/or the second analyte is/are unlabeled. While the disclosed methods can be used in connection with unlabeled analytes, it is contemplated that the analytes can be optionally labeled. Such labeling can be convenient for preceding, subsequent, or simultaneous analysis by other analytical methods. In a still further aspect, at least one of the analytes is unlabeled. In yet a further aspect, both analytes are unlabeled.

In a further aspect, the first and/or second analyte is one or more of an antibody, an antigen, a protein, a small molecule, a drug, a receptor, a cell, an oligonucleotide, a carbohydrate, an enzyme, a substrate, a DNA, an aptamer, a RNA, a nucleic acid, a biomolecule, a molecular imprint, a protein mimetic, an antibody derivative, a lectin, a cell membrane, an ion, a virus particle, a bacteria, and a microRNA.

In a further aspect, detecting a molecular interaction comprises determining a change in a physical or chemical property of the first and/or second sample. In a still further aspect, the change in a physical or chemical property of the first and/or second sample corresponds to the formation of one or more interaction products.

In a further aspect, detecting a molecular interaction comprises determining an equilibrium constant, a dissociation constant, a dissociation rate, or an association rate. In a still further aspect, detecting comprises determining the concentration of the first and/or second analyte. In yet a further aspect, detecting comprises identifying the presence of a third analyte. In an even further aspect, calculating a change in hydrodynamic volume, entropy, or enthalpy.

In a further aspect, detecting a molecular interaction comprises determining a change in a physical or chemical property of the fluid sample. In a still further aspect, the change in physical or chemical property of the fluid sample corresponds to the formation of one or more interaction products.

In a further aspect, the molecular interaction is the formation of one or more covalent bonds, electrostatic bonds, hydrogen bonds, or hydrophobic interactions. In a further aspect, the molecular interaction is a binding event between one or more of antibody-antigen, protein-protein, small molecule-small molecule, small molecule-protein, drug-receptor, antibody-cell, virus-cell, virus-protein, bacteria-cell, bacteria-protein, virus-DNA, virus-RNA, bacteria-DNA, bacteria-RNA, protein-cell, oligonucleotide-cell, carbohydrate-cell, cell-cell, enzyme-substrate, protein-DNA, protein-aptamer, DNA-DNA, RNA-DNA, DNA-RNA, protein-RNA, small molecule-nucleic acid, biomolecule-molecular imprint, biomolecule-protein mimetic, biomolecule-antibody derivatives, lectin-carbohydrate, biomolecule-carbohydrate, small molecule-cell membrane, ion-protein, and protein-protein.

In a further aspect, the molecular interaction comprises one or more of a change in conformational structure of the first and/or second analyte and a change in hydration of the first and/or second analyte. In a still further aspect, the molecular interaction comprises a change in conformational structure of the first and/or second analyte. In yet a further aspect, the molecular interaction comprises a change in hydration of the first and/or second analyte. In an even further aspect, the molecular interaction comprises a change in conformational structure of the first and/or second analyte and a change in hydration of the first and/or second analyte.

In a further aspect, the molecular interaction lacks a change in mass. In a still further aspect, the molecular interaction is a chemical reaction.

In various aspects, the first and/or second sample is a fluid sample. In a further aspect, a fluid sample can comprise at least one of a liquid or a gas. In particular aspects, a fluid sample comprises a solution of one or more analytes and one or more liquid solvents. A solution can be provided in an organic solvent or in water. In certain aspects, the solution can comprise man-made preparations or naturally occurring substances. In certain aspects, the solution can comprise a body fluid (e.g., peripheral blood, urine, cerebrospinal fluid, pulmonary lavage, gastric lavage, bile, vaginal secretions, seminal fluid, aqueous humor, vitreous humor, serum, and saliva) from a human, a mammal, another animal, or a plant.

In a further aspect, the refractive index sensor comprises a prism.

In a further aspect, the refractive index sensor comprises a substrate having a first channel formed therein for reception of a fluid sample to be analyzed and wherein the first and second analyte are introduced into the channel. Generally, the substrate and channel can comprise any material suitable for containing and providing a sample for analysis and capable of being interrogated by light. In one aspect, the substrate and channel together comprise a capillary tube. In a further aspect, wherein the substrate and channel together comprise a microfluidic device.

In a further aspect, the microfluidic device comprises a polymeric substrate and an etched channel formed in the substrate for reception of a fluid sample, the channel having a cross sectional shape. In a further aspect, the polymeric substrate can be selected from rigid and transparent plastics. In various further aspects, the polymeric substrate comprises one or more polymers selected from polycarbonate, polydimethylsiloxane, fluorosilicone, polytetrafluoroethylene, poly(methyl methacrylate), polyhexamethyldisilazane, polypropylene, starch-based polymers, epoxy, and acrylics.

In a further aspect, the microfluidic device comprises a silica substrate and an etched channel formed in the substrate for reception of a fluid sample, the channel having a cross sectional shape, which can be substantially circular, substantially semi-circular, or substantially rectangular, as disclosed herein.

In a further aspect, the first channel is configured for reception of two or more fluid samples by having at least two inlets positioned at opposing locations of the channel, and at least one outlet positioned at a point between the at least two inlets, thereby defining a right side of the channel and a left side of the channel and wherein the first sample is introduced into the right side of the channel and the second sample is introduced into the left side of the channel.

It is contemplated the substrate can comprise one or more than one channel. Thus, in a further aspect, the substrate further comprises a second channel. In a still further aspect, the first analyte is introduced into the first channel and the second analyte is introduced into the second channel. In yet a further aspect, the first and second analyte are introduced into the first channel.

In a further aspect, the substrate further comprises a reference channel. In a still further aspect, the method further comprises the steps of: (a) introducing a reference sample; (b) interrogating the reference sample with light; (c) detecting the light after interaction with the reference sample, wherein the detected light is not backscattered; (d) determining a characteristic of the reference sample; and (e) employing the characteristic of the reference sample to compensate for background interference effects in the determination of the molecular interaction between the first and second analyte in the first channel.

The disclosed methods can provide real-time, free-solution detection of molecular interactions with very low detection limits. That is, in one aspect, the invention relates to a free-solution analytical method for detecting molecular interactions comprising the step of detecting a molecular interaction between two non-immobilized analytes, wherein at least one of the analytes is present during the determination at a concentration of less than about $5.0 \times 10^4$ M. In various further embodiments, the concentration can be less than about $1.0 \times 10^4$ M, for example, less than about $5.0 \times 10^{-5}$ M, less than about $1.0 \times 10^{-5}$ M, less than about $5.0 \times 10^{-6}$ M, less than about $1.0 \times 10^{-6}$ M, less than about $5.0 \times 10^{-7}$ M, less than about $1.0 \times 10^{-7}$ M, less than about $5.0 \times 10^{-8}$ M, less than about $1.0 \times 10^{-8}$ M, less than about $5.0 \times 10^{-9}$ M, or less than about $1.0 \times 10^{-9}$ M. In a further aspect, the concentration can be less than about $5.0 \times 10^{-1}$ M, for example, less than about $1.0 \times 10^{-10}$ M, less than about $5.0 \times 10^{-11}$ M, less than about $1.0 \times 10^{-11}$ M, less than about $5.0 \times 10^{-12}$ M, less than about $1.0 \times 10^{-12}$ M, less than about $5.0 \times 10^{-13}$ M, less than about $1.0 \times 10^{-13}$ M, less than about $5.0 \times 10^{-14}$ M, less than about $1.0 \times 10^{-14}$ M, less than about $5.0 \times 10^{-15}$ M, or less than about $1.0 \times 10^{-15}$ M.

The disclosed methods can provide real-time, free-solution detection of molecular interactions with very low sample volume requirements. That is, in one aspect, the invention relates to a free-solution analytical method for detecting molecular interactions comprising the step of detecting a molecular interaction between two non-immobilized analytes, wherein at least one of the analytes is present during the determination in a solution with a volume in the detection zone of less than about 500 µL. In various further embodiments, the sample volume can be less than about 250 µL, for example, less than about 100 µL, less than about 10 µL, less than about 1 µL, less than about 500 nL, less than about 250 nL, less than about 100 nL, less than about 10 nL, less than about 1 nL, less than about 500 pL, less than about 250 pL, or less than about 100 pL.

In a further aspect, the first and/or second sample comprises an additive. In a still further aspect, the additive is selected from an alcohol, an acid, a base, a high refractive index solvent, a surfactant, and an intercalating agent. In yet a further aspect, the alcohol is deuterated. In an en even further aspect, the alcohol is fluorous.

In a further aspect, the disclosed methods further comprise the step of determining a change in refractive index. In a still further aspect, the change in refractive index is at least about $10^{-3}$ RIU. In yet a further aspect, the change in refractive index is at least about $10^{-4}$ RIU. In an even further aspect, the change in refractive index is at least about $10^{-5}$ RIU. In a still further aspect, the change in refractive index is at least about $10^{-6}$ RIU. In yet a further aspect, the change in refractive index is at least about $10^{-7}$ RIU. In an even further aspect, the change in refractive index is at least about $10^{-8}$ RIU.

In a further aspect, the disclosed methods further comprise the step of performing a chromatographic separation and/or an electrophoretic separation on the sample before, during, or after the determining the determining step. In a still further aspect, the method further comprises the step of performing a chromatographic separation or an electrophoretic separation on the sample prior to the determining the determining step. In yet a further aspect, the method further comprises performing a chromatographic separation or an electrophoretic separation on the sample during the determining the determining step. In an even further aspect, the method further comprises performing a chromatographic separation or an electrophoretic separation on the sample after the determining the determining step. In a still further aspect, the method further comprises performing a chromatographic separation and an electrophoretic separation on the sample prior to the determining the determining step. In yet a further aspect, the method further comprises performing a chromatographic separation and an electrophoretic separation on the sample during the determining the determining step. In an even further aspect, the method further comprises performing a chromatographic separation and an electrophoretic separation on the sample after the determining the determining step.

E. Methods for Determining a Characteristic Property of a Sample

In one aspect, disclosed are methods for determining a characteristic property of a sample, the method comprising the steps of: (a) providing a refractive index sensor for reception of a fluid sample to be analyzed; (b) introducing a fluid sample to be analyzed onto the sensor; (c) interrogating the fluid sample with light; (d) detecting the light after interaction with the fluid sample, wherein the detected light is not backscattered; and (e) determining the characteristic property of the sample. In a further aspect, the fluid sample to be analyzed comprises an analyte. In a still further aspect, the analyte is non-immobilized. In yet a further aspect, the analyte is unlabeled.

In one aspect, disclosed are free-solution analytical method comprising detecting a molecular change, wherein the detection is performed by refractive index sensing other than backscattering interferometry. In a further aspect, the detection is performed by refractive index sensing other than forward scattering or side scattering interferometry. In a still further aspect, detecting a molecular change comprises determining the degree of polymerization, protein folding, protein aggregation, blood oxygenation, the conformational state of an ion channel or membrane protein, or the hydration state of an ion channel or membrane protein.

In a further aspect, the light is not scattered.

In a further aspect, the refractive index sensor comprises a substrate having a first channel formed therein for reception of a fluid sample to be analyzed and wherein the sample is introduced into the channel. Generally, the substrate and channel can comprise any material suitable for containing and providing a sample for analysis and capable of being interrogated by light. In one aspect, the substrate and channel together comprise a capillary tube. In a further aspect, wherein the substrate and channel together comprise a microfluidic device.

In a further aspect, a channel is formed in the substrate and the method further comprises the steps of: (a) introducing a reference sample in the second channel; (b) determining a characteristic of the reference sample; and (c) employing the characteristic of the reference sample to compensate for background interference effects in the determination of the characteristic of the sample in the first channel.

In a further aspect, the substrate has a channel formed therein with a generally hemispherical cross sectional shape. In a still further aspect, the channel is formed with first and second curved portion, each curved portion defining a 90° arc, and a first flat portion connecting the first and second curved portions.

In a further aspect, the sample is positioned inside a channel formed in a substrate, the channel has a longitudinal direction and a transverse direction, and the light is elongated in the longitudinal direction of the channel. In a still further aspect, the light is incident on at least a portion of the channel greater than 4 mm in length along the longitudinal direction.

In various aspects, the light source generates an easy to align optical beam that is incident on the etched channel for generating scattered light. In a further aspect, the light source generates an optical beam that is collimated, such as, for example, the light emitted from a HeNe laser. In a still further aspect, the light source generates an optical beam that is not well collimated and disperses in, for example, a Gaussian profile, such as that generated by a diode laser.

Typically, two types of lasers can be employed. In various aspects, one laser (the diode) creates a laser beam that is elongated in the longitudinal direction of the channel. In further aspects, the other (HeNe) creates a laser beam that is not elongated longitudinally along the length of the channel, but can be later elongated longitudinally along the length of the channel by beam-stretching optics. These methods can both achieve the same end of an elongated beam impinging upon the channel, but do so through different means. It can be noted that, in certain aspects, when the diameter of the laser beam is the same as the thickness of the glass chip, new interference phenomena can arise. This can be avoided by selecting the width of the beam to be smaller than the thickness of the glass chip (0.8 mm width laser and 1.7 mm thickness glass chip).

In a further aspect, a single light beam is incident upon the substrate.

In a further aspect, the light beam has a substantially uniform intensity profile across at least a portion of the plurality of discrete zones. In a yet further aspect, the light beam has a substantially Gaussian intensity profile in the axis perpendicular to the zones. In a still further aspect, the portion of the light beam impinging the channel has an elongated intensity profile.

In various aspects, the light beam is incident on at least a portion of the channel greater than 4 mm in length along the longitudinal direction. In a further aspect, the light beam is incident on at least a portion of the channel greater than 5 mm of length of the channel in the longitudinal direction. In a still further aspect, the light beam is incident on at least a portion of the channel greater than 6 mm of length of the channel in the longitudinal direction. In yet a further aspect, the light beam is incident on at least a portion of the channel greater than 7 mm of length of the channel in the longitudinal direction. In an even further aspect, the light beam is incident on at least a portion of the channel greater than 8 mm of length of the channel in the longitudinal direction. In a still further aspect, the light beam is incident on at least a portion of the channel greater than 9 mm of length of the channel in the longitudinal direction. In yet a further aspect, the light beam is incident on at least a portion of the channel greater than 10 mm, 12 mm, 14 mm, 16 mm, 18 mm, or 20 mm of length of the channel in the longitudinal direction.

In a further aspect, at least a portion of the light beam incident on the channel covers at least two discrete zones. In a still further aspect, at least a portion of the light beam is incident on the channel such that the intensity of the light on each of at least two zones is the same or substantially the same. In yet a further aspect, at least a portion of the light beam is incident on the channel such that the each of the zones along the channel receive the same or substantially the same intensity of light. For example, a light beam having a Gaussian intensity profile can be incident on a channel such that at least two zones along the channel are within the peak of the intensity profile, receiving the same or substantially the same intensity of light. In an even further aspect, the portion of the light beam incident on the channel can have a non-Gaussian profile, such as, for example, a plateau (e.g., top-hat). The portion of the light beam in the wings of the Gaussian intensity profile can be incident upon other portions of the channel or can be directed elsewhere.

In a further aspect, variations in light intensity across zones of interest can result in measurement errors. In a still further aspect, if portions of a light beam having varying intensity are incident upon multiple zones of a channel, a calibration can be performed wherein the expected intensity of light, resulting interaction, and scattering is determined for correlation of future measurements.

The light source can comprise any suitable equipment and/or means for generating light, provided that the frequency and intensity of the generated light are sufficient to interact with a sample and/or a marker compound and provide elongated fringe patterns as described herein. Light sources, such as HeNe lasers and diode lasers, are commercially available and one of skill in the art could readily select an appropriate light source for use with the systems and methods of the present invention.

In a further aspect, the light beam is directed from a laser formed integrally on the substrate. In a still further aspect, the photodetector is formed integrally on the substrate.

In a further aspect, the characteristic property comprises the index of refraction of the sample. In a still further aspect, the characteristic property comprises the temperature of the sample.

In a further aspect, the characteristic property to be determined is whether first and second biochemical functional species bind with one another, and the step of introducing a sample to be analyzed onto the sensor comprises introducing the first biochemical functional species into the channel and introducing the second biochemical functional species into the channel to facilitate a binding reaction between the first and second biochemical species.

In a further aspect, the first and second biochemical functional species are introduced sequentially. In a still further aspect, the first and second biochemical functional species are introduced simultaneously.

In a further aspect, the first biochemical functional species is allowed to interact with the second biochemical functional species prior to introducing the first and/or second biochemical species onto the sensor. In a still further aspect, the first biochemical functional species is allowed to interact with the second biochemical functional species after introducing the first and/or second biochemical species onto the sensor.

In a further aspect, the first and second biochemical functional species are selected from the group comprising complimentary strands of DNA, complimentary proteins, and antibody antigen pairs.

In a further aspect, the substrate is selected to be formed from PDMS.

In a further aspect, the laser beam is selected to have a diameter of 2 mm or less. In a still further aspect, the channel, when present, is selected to have a width that is no larger than the diameter of the laser beam.

In a further aspect, the refractive index sensor comprises a prism.

F. Methods for Determining a Characteristic Property of a Sample Using Single Channel Sample Reference (SCSR)

In the single channel sample reference (SCSR) configuration, a collimated laser beam is expanded, for example, to approximately 8-10 mm, in the axis along the channel, while maintaining the Gaussian shape in the axis perpendicular to the channel. When this beam is impinged onto the microfluidic channel, at least two samples can be interrogated in the channel simultaneously. By separating the samples with either an air gap, a droplet of immiscible material, or other gap or hole in the channel, the samples may be probed in the same channel simultaneously, with the same laser. Thus, the sample and the reference may be interrogated in the same refractive index sensing device.

In a further aspect, refractive index sensing is via a refractometer. In a still further aspect, refractive index sensing is via interferometry. In yet a further aspect, refractive index sensing is via forward scattering interferometry. In an even further aspect, refractive index sensing is via backscattering interferometry. In a still further aspect, refractive index sensing is via a hand-held refractive index sensing device.

It is contemplated that the method can be used to determine, for example, one or more of an equilibrium constant, a dissociation constant, a dissociation rate, a dissociation rate constant, an association rate, and/or an association rate constant of the interaction. In a further aspect, the method can be used to determine, for example, the concentration of the first and/or second analyte. In a still further aspect, the method can be used to determine, for example, the presence of the first and/or second analyte. In yet a further aspect, the method can be used to determine, for example, the presence of a third analyte.

In various aspects, the sample may be contained in, e.g. flowed through, a capillary dimensioned flow channel such as a capillary tube. The cross-sectional depth of the channel is limited only by the length of the light and its breadth is limited only by the width of the light beam. Preferably, the depth of the channel is from 1 to 10 $\mu$m, but it may be from 1 to 20 $\mu$m or up to 50 $\mu$m or more, e.g. up to 1 mm or more. However, sizes of up to 5 mm or 10 mm or more are possible. Suitably, the breadth of the channel is from 0.5 to 2 times its depth, e.g., equal to its depth.

Typically, at least one the interfaces involving the sample at which light is reflected is curved in a plane containing the light path, the curved interface being convex in the direction facing the incoming light if it is the interface between the first material and the sample and being concave in the direction facing the incoming light if it is the interface between the sample and the further material. The sample is typically a liquid, and can be flowing or stationary. However, the sample can also be a solid or a gas in various aspects of the present invention. The first and/or further materials will normally be solid but in principle can be liquid, e.g., can be formed by a sheathing flow of guidance liquid(s) in a microfluidic device, with the sample being sheathed flow of liquid between such guidance flows. The sample may also be contained in a flow channel of appropriate dimensions in substrate such as a microfluidic chip. The method may therefore be employed to obtain a read out of the result of a reaction conducted on a "lab on a chip" type of device.

In various aspects, the disclosed methods are capable of measuring multiple signals, for example, along a length of a capillary channel, simultaneously or substantially simultaneously. In a further aspect, a plug could be incorporated in the center of the capillary, allowing the sample and the reference to be drawn into the capillary without them coming in contact with each other or mixing. In a still further aspect, two or more capillaries could be used. In yet a further aspect, a tray of capillaries may be used. In an even further aspect, each capillary may be analyzed one at a time. In a still further aspect, more than one capillary may be analyzed at one time.

In a further aspect, and while not wishing to be bound by theory, the refractive index changes that can be measured by the disclosed methods can arise from molecular dipole alterations associated with conformational changes of sample-ligand interaction as well as density fluctuations due to changes in waters of hydration. These RI changes also arise from redistribution of the electron density of an ion, atom, or molecule resulting from changes in, for example, sample pH, solvent composition, or molecular interactions.

The detection system has numerous applications, including, for example, the observation and quantification of molecular interactions, molecular concentrations, bioassays, universal/RI detection for CE (capillary electrophoresis), CEC (capillary electrochromatography) and FIA (flow injection analysis), physiometry, cell sorting/detection by scatter, ultra micro calorimetry, flow rate sensing, PCR quantification, and temperature sensing. One of the advantages of the disclosed methods is that a sample measurement and reference measurement can be acquired simultaneously or substantially simultaneously from the same channel. As both measurements occur in the same capillary and, in one aspect, in immediately adjacent portions of the capillary, the thermal properties attributable to each measurement will be uniform, resulting in higher signal to noise levels.

In various aspects, the detection systems and methods described herein can be useful as a bench-top molecular interaction photometer. In a further aspect, the detection systems and methods described herein can be useful for performing near patient diagnostics. In a still further aspect, the detection system can be useful for performing assays in the field, in the home, in space, or in remote locations.

In various aspects, the detection systems and methods described here can be useful as a hand-held version of a refractive index sensing device. In a further aspect, the detection systems and methods described here can be useful as a hand-held version of a refractometer. In a still further aspect, the detection systems and methods described here can be useful as a hand-held version of an interferometer.

1. Using SCSR

In one aspect, disclosed are methods for determining a characteristic property of a sample, the method comprising the steps of: (a) providing a channel formed in a substrate, wherein the channel has a longitudinal direction and a transverse direction, and wherein the channel is configured for reception of two or more fluid samples by having at least two inlets positioned at opposing locations of the channel, and at least one outlet positioned at a point between the at least two inlets, thereby defining a right side of the channel and a left side of the channel; (b) introducing a first sample comprising a first non-immobilized analyte to be analyzed into the left side of the channel; (c) introducing a second sample comprising a second non-immobilized analyte to be analyzed into the right side of the channel; (d) simultaneously interrogating the samples with light, wherein the light is elongated in the longitudinal direction of the channel, such that the light beam is incident on at least a portion of the left side of the channel and the right side of the channel; (e) detecting the light after interaction with the samples, wherein the detected light is not backscattered; and (f) determining the characteristic property of the sample. In a further aspect, the detected light is not scattered.

It is well known in the art that one of the most challenging aspects of implementing any microfluidic technology, such as interferometry, is to overcome the inherent difficulty of injecting or introducing samples (See, e.g., "Microfluidics Toward a Lab-on-a-Chip," Annu. Rev. Fluid Mech. 2004. 36:381-411, doi: 10.1146/annurev.fluid.36.050802.122124; and "Macro-to-micro interfaces for microfluidic devices," Carl K. Fredrickson and Z. Hugh Fan* Lab Chip, 2004, 4, 526-533). There are many contributing factors here, including the unique properties of the channel such as the small cross section, the unique flow profile of microfluidics, and the physical properties of the sample.

The single channel sample reference (SCSR) configuration utilizes a new sample introduction methodology, whereby a droplet of the sample is placed in a well at one end of the microfluidic chip, and capillary action serves to pull the material into the interrogating region. An inlet well at each end of the channel and a hole drilled through the center allows for three goals to be accomplished. First, the hole allows air to escape as the sample is pulled in by capillary action, keeping the pressure within the microfluidic channel stable. This is particularly important, because dn/dP (refractive index response to pressure) can be a major source of noise in RI measurements, particularly in systems where the sample volume is constrained or held in a channel which is in poor communication with the local atmosphere (e.g., cannot come to equilibrium after introduction). Second, the hole allows the sample to be removed post measurement by simple vacuum. Third, the hole acts as a barrier for the samples so they do not mix during measurements. Fourth, the hole allows a sample and a reference to be placed at each end of the channel, with both able to be pulled into the chip independently by capillary action, but reaching the same temperature and pressure rapidly. Proper design of the hole or gap to keeps the samples from jumping across the gap, from mixing and to come rapidly to equilibrium. After measurement, it can be important that sample removal be swift and complete. Any sample left over in the channel can contaminate the next sample and hinder smooth capillary action. The use of a switch connected to the tube at the outlet allows the channels to be free in contact with the outside air, but also solidly attached to the vacuum to remove sample.

In various aspects, an inlet may be located at each end of the channel and a single outlet in between. It is also envisioned, however, that the channel may comprise more than two inlets, each with a hole in between them.

Samples also cover a wide range of compositions and properties. Some are hydrophobic and some are hydrophilic. They can be aqueous, organic, mixed aqueous-organic and mixed with additives such as salts, surfactants, and acids or bases. Aqueous solutions with surfactant constitute samples that are less hydrophilic than water alone, so dispensing them can be challenging. Samples can contain high concentrations of salt as with buffers, or both buffer salts and surfactant (as required for some protein interaction studies) making them prone to evaporation and changing their capillary action power in glass channels. In this case, the capillary action problem may be overcome by specially coating the injection guide (miscellaneous vendors) to insure wicking into the chip channel. Samples can be sticky, with the matrix and/or samples adhering non-specifically to the introduction guide. Samples such as serum, urine, cells, cell-derived vesicles, tissue-derived vesicles, membrane preps, etc., are particularly challenging. Without wishing to be bound by theory, the approach described herein may enable a minimally trained user to introduce all of these samples with the reproducibility (<2.0 milliradians) required to perform assays and with considerably improved reproducibility.

In a further aspect, the method further comprises the steps of receiving the intensity signals with a signal analyzer and determining therefrom one or more characteristic properties of at least one of the samples.

In a further aspect, the light beam is incident on greater than 4 mm of length of the channel in the longitudinal direction. In a still further aspect, the light beam is incident on greater than 4 mm of length of the left side of the channel in the longitudinal direction. In yet a further aspect, the light beam is incident on greater than 4 mm of length of the right side of the channel in the longitudinal direction.

The disclosed techniques can determine the interaction between one or more analytes by monitoring, measuring, and/or detecting the formation and/or steady state relative abundance of one or more analyte interaction products from the interaction of the one or more analytes. The determination can be performed qualitatively or quantitatively. Interaction rate information can be derived from various measurements of the interaction.

In a further aspect, the first sample is combined with the second sample prior to introduction. That is, the analytes are combined (and potentially interacting) prior to performing the disclosed methods. In this aspect, the step of introducing the first sample and the step of introducing the second sample are performed simultaneously.

In a further aspect, the first sample is combined with the second sample after introduction. That is, the analytes can be combined at a point before the sensor, or at a point on the sensor, when performing the disclosed methods. In this aspect, the step of introducing the first analyte and the step of introducing the second analyte are performed either simultaneously or sequentially. In a further aspect, the detecting step is performed during the interaction of the first analyte with the second analyte.

Thus, in various aspects, the first and second samples are introduced simultaneously. In a further aspect, the first and second samples are introduced sequentially. In a still further aspect, the first analyte is allowed to interact with the second analyte prior to introducing the first and/or second sample onto the sensor. In yet a further aspect, the first analyte is allowed to interact with the second analyte after introducing the first and/or second sample onto the sensor. In an even further aspect, the first analyte is allowed to interact with the second act while introducing the first and/or second sample onto the sensor.

2. Interrogation Region Length

In one aspect, disclosed are methods for determining a characteristic property of a sample comprising the steps of: (a) providing a sample comprising a non-immobilized analyte to be analyzed, wherein the sample is positioned inside a channel formed in a substrate, and wherein the channel has a longitudinal direction and a transverse direction; (b) interrogating the sample with a light beam, wherein the light beam is elongated in the longitudinal direction of the channel, such that the light beam is incident on at least a portion of the channel greater than 4 mm in length along the longitudinal direction; and (c) detecting the light after interaction with the sample, wherein the detected light is not backscattered. In a further aspect, the detected light is not scattered.

In various aspects, the light beam may be elongated to take more measurements, e.g., by spreading the light in the direction of the sample and/or reference, and then averaging the data. This technique serves to increase the S/N ratio. In this way, a single measurement may provide data comparable to taking multiple measurements.

In various aspects, the light beam is incident on greater than 4 mm of length of the channel in the longitudinal direction. In a further aspect, the light beam is incident on greater than 5 mm of length of the channel in the longitudinal direction. In a still further aspect, the light beam is incident on greater than 6 mm of length of the channel in the longitudinal direction. In yet a further aspect, the light beam is incident on greater than 7 mm of length of the channel in the longitudinal direction. In an even further aspect, the light beam is incident on greater than 8 mm of length of the channel in the longitudinal direction. In a still further aspect, the light beam is incident on greater than 9 mm of length of the channel in the longitudinal direction. In yet a further aspect, the light beam is incident on greater than 10 mm, 12 mm, 14 mm, 16 mm, 18 mm, or 20 mm of length of the channel in the longitudinal direction.

In a further aspect, the method further comprises the steps of receiving the intensity signals with a signal analyzer and determining therefrom one or more characteristic properties of the sample.

3. Photodetector Integration Dimensions

In one aspect, the invention relates to methods for determining a characteristic property of a sample comprising the steps of: (a) providing a sample comprising a first non-immobilized analyte to be analyzed, wherein the sample is positioned inside a channel formed in a substrate, and wherein the channel has a longitudinal direction and a transverse direction; (b) interrogating the sample with a light beam, wherein the light beam is elongated in the longitudinal direction of the channel, wherein the photodetector is positioned less than 40 cm from the channel during interrogation; and (c) detecting the light after interaction with the sample, wherein the detected light is not backscattered. In a further aspect, the detected light is not scattered.

Optimum photodetector integration dimensions is dependent on chip configurations (e.g., chip material, substrate and top plate thickness, channel dimensions, shape, etc.) and the distances from the channel (e.g., chip top) surface to the camera sensor. Thus, in various aspects, the photodetector is positioned less than about 40 cm (e.g., less than about 36 cm, less than about 32 cm, less than about 30 cm, less than about 28 cm, less than about 26 cm, less than about 24 cm, less than about 22 cm, less than about 20 cm, less than about 18 cm, less than about 16 cm, less than about 14 cm, less than about 12 cm, less than about 10 cm, less than about 9 cm, less than about 8 cm, less than 7 cm, less than about 6 cm, less than about 5 cm, less than about 4 cm, less than about 3 cm, less than about 2 cm, less than about 1 cm) from the channel during interrogation. For example, the photodetector can be positioned from about 2 cm to about 40 cm, from about 2 cm to about 20 cm, from about 2 cm to about 10 cm, from about 5 cm to about 20 cm, from about 5 cm to about 10 cm, from about 5 cm to about 40 cm, from about 10 cm to about 40 cm, from about 10 cm to about 30 cm, or from about 5 cm to about 30 cm from the channel during interrogation.

The camera resolution, including pixel size, spacing, and photon flux sensitivity, must also conform to a minimum specification. Thus, in various aspects, between about 30 camera pixels and 500 camera pixels may be interrogated. In a further aspect, between about 30 camera pixels and 350 camera pixels may be interrogated. In a still further aspect, between about 30 camera pixels and 300 camera pixels may be interrogated. In yet a further aspect, between about 30 camera pixels and 250 camera pixels may be interrogated. In an even further aspect, between about 30 camera pixels and 200 camera pixels may be interrogated. In a still further aspect, between about 30 camera pixels and 150 camera pixels may be interrogated. In yet a further aspect, between about 50 camera pixels and 100 camera pixels may be interrogated. In an even further aspect, between about 100 camera pixels and 500 camera pixels may be interrogated. In a still further aspect, between about 150 camera pixels and 500 camera pixels may be interrogated. In yet a further aspect, between about 200 camera pixels and 500 camera pixels may be interrogated. In an even further aspect, between about 250 camera pixels and 500 camera pixels may be interrogated. In a still further aspect, between about 300 camera pixels and 500 camera pixels may be interrogated.

This optical configuration may allow for several advantages. For example, the effect of air currents and temperature perturbations may be reduced thereby decreasing environmental noise.

In various aspects, the light beam is incident on at least a portion of the channel greater than 4 mm in length along the longitudinal direction. In a further aspect, the light beam is incident on at least a portion of the channel greater than 5 mm of length of the channel in the longitudinal direction. In a still further aspect, the light beam is incident on at least a portion of the channel greater than 6 mm of length of the channel in the longitudinal direction. In yet a further aspect, the light beam is incident on at least a portion of the channel greater than 7 mm of length of the channel in the longitudinal direction. In an even further aspect, the light beam is incident on at least a portion of the channel greater than 8 mm of length of the channel in the longitudinal direction. In a still further aspect, the light beam is incident on at least a portion of the channel greater than 9 mm of length of the channel in the longitudinal direction. In yet a further aspect, the light beam is incident on at least a portion of the channel greater than 10 mm of length of the channel in the longitudinal direction.

In a further aspect, the method further comprises the steps of receiving the intensity signals with a signal analyzer and determining therefrom one or more characteristic properties of the sample.

4. Using Multiple Elements

In one aspect, the invention relates to a method for determining a characteristic property of a sample comprising the steps of: (a) providing a channel formed in a substrate, wherein the channel has a longitudinal direction and a transverse direction, and wherein the channel is configured for reception of two or more fluid samples by having at least two inlets positioned at opposing locations of the channel, and at least one outlet positioned at a point between the at least two inlets, thereby defining a right side of the channel and a left side of the channel; (b) introducing a first sample comprising a first non-immobilized analyte to be analyzed into the left side of the channel and then closing the inlet of the left side of the channel with a first closure element, thereby reducing evaporation of the first sample; (c) introducing a second sample comprising a second non-immobilized analyte to be analyzed into the right side of the channel and then closing the inlet of the right side of the channel with a second closure element, thereby reducing evaporation of the second sample; (d) simultaneously interrogating the samples with a light beam, wherein the light beam is elongated in the longitudinal direction of the channel, such that the light beam is incident on greater than 4 mm of length of the channel in the longitudinal direction and simultaneously incident on at least a portion of the left side of the channel and at least a portion of the right side of the channel, wherein the photodetector is positioned less than 40 cm from the channel during interrogation; and (e) detecting the light after interaction with the sample, wherein the detected light is not backscattered. In a further aspect, the detected light is not scattered.

In a further aspect, the method further comprises the steps of receiving the intensity signals with a signal analyzer and determining therefrom one or more characteristic properties of at least one of the sample.

In a further aspect, the light beam is incident on greater than 4 mm of length of the channel in the longitudinal direction. In a still further aspect, the light beam is incident on greater than 4 mm of length of the left side of the channel in the longitudinal direction. In yet a further aspect, the light beam is incident on greater than 4 mm of length of the right side of the channel in the longitudinal direction.

G. Detection of Chemical Events

The disclosed methods can be used in connection with the detection and determination of a wide variety of characteristic properties of a sample. For example, the invention can be used to determine absolute or relative refractive index (RI) of a sample, for example a fluid either flowing or static. The disclosed systems and methods can also be used in connection with detection and determination of chemical events, for example label-free analysis of hybridization reactions such as DNA-DNA binding reactions. The disclosed systems and methods can also be used in bioassays, monitoring enzymatic activity, drug screening, and clinical diagnostics.

In one aspect, the disclosed methods can be performed wherein the characteristic to be determined is whether first and second biochemical functional species (i.e., first and second analytes) bind with one another, and the step of introducing a sample to be analyzed into the first channel comprise introducing the first biochemical functional species into the channel and then introducing the second biochemical functional species into the channel to facilitate a binding reaction between the first and second biochemical species. For example, the first and second biochemical functional species can be selected from the group comprising complimentary strands of DNA, complimentary proteins, enzyme-substrate pairs, and antibody antigen pairs. That is, in a further aspect, the characteristic to be determined can be a label-free analysis of a hybridization reaction in the channel. In a yet further aspect, the positional shifts in the light bands can correspond to a chemical event occurring in the sample.

Examples of chemical events that can be detected and bioassays conducted with the disclosed systems and methods include a binding event between one or more of antibody-antigen, protein-protein, small molecule-small molecule, small molecule-protein, drug-receptor, antibody-cell, virus-cell, virus-protein, bacteria-cell, bacteria-protein, virus-DNA, virus-RNA, bacteria-DNA, bacteria-RNA, protein-cell, oligonucleotide-cell, carbohydrate-cell, cell-cell, enzyme-substrate, protein-DNA, protein-aptamer, DNA-DNA, RNA-DNA, DNA-RNA, protein-RNA, small molecule-nucleic acid, biomolecule-molecular imprint, biomolecule-protein mimetic, biomolecule-antibody derivatives, lectin-carbohydrate, biomolecule-carbohydrate, small molecule-cell membrane, ion-protein, and protein-protein.

In one aspect, the disclosed systems and methods can be used in connection with a step of performing a chromatographic separation or an electrophoretic separation on the sample prior to the determining the characteristic property step.

1. Analytical Detection Events

The invention also finds use as a detector for other chip-scale analytical schemes including electrophoresis, µ-HPLC separations, and FIA. It is possible to detect molecules important to cellular function, high throughput analysis, and pharmaceutical screening. The refractive index sensing device can also be used in biochemical assays and to quantify environmental analytes. It is also possible to perform micro-thermometry, the device has the capability of measuring small temperature changes (in the $10^{-3}$° C. range)

allowing for cellular respiration, protein folding, calorimetry, and fundamental chemical binding studies to be performed in picoliter volumes. Furthermore, when using special surface chemistry to selectively bind solutes, such as DNA oligomers, proteins, or antibodies, without sacrificing specificity/sensitivity. Use of the device to perform flow sensing, pressure sensing, time resolved enthalpies and perform detection for products eluted from focusing techniques such as flow cytometry is also viable, as well as the ability to monitor label-free reactions and to quantify the interference brought on by fluorescent markers normally attached to biomolecules.

H. Molecular Interactions and Biosensor Applications

Molecular interaction analysis is an active area of biomedical research as scientists look for understanding of which molecules bind to other molecules. This information can be critical on any number of levels, especially as it pertains to an understanding of the mechanism of action of pharmaceutical small molecules or biological macromolecules. The study of interactions can also elucidate possible mechanisms of toxicity and can help identify how best to modify molecules to become more effective therapeutics. A thorough understanding of which molecules bind which molecules can also lead to a more comprehensive understanding of the molecular pathways involved in gene function which can help identify new points of intervention in disease states such as cancer or diabetes, or new points of intervention in the pathways that contribute to aging. Molecular interactions can also provide a rapid diagnostic tool for the presence or absence of molecules that are correlated with disease or with the presence of pathogens in the environment.

Historically, scientists have used semi-quantitative methods such as genetic, biochemical, and structure-function methods that have produced qualitative or semiquantitative interaction data. Beginning in 1990, Biacore introduced the first commercial machine to use surface plasmon resonance (SPR) to study the real time kinetics of biomolecular interactions. Systems biology approaches will require these types of data to better model the huge number of interactions forming specific molecular networks.

Biosensors have been defined as any type of device that contains a bioreceptor and a transducer. The bioreceptor can be a biological molecular species such as a nucleic acid, a protein, enzyme, antibody or even a living biological system such as cells or whole organisms that would bind the target species. The transducer would then convert this binding event into a measurement that could be recorded or displayed. Several types of transducers have been developed, including optical measurements (including fluorescence, luminescence, absorption, phosphorescence, Raman, SERS, surface Plasmon resonance, and back-scattering interferometry), electrochemical, and mass-sensitive (including surface acoustic wave and microbalance).

1. Antibody Biosensors

In conventional antibody biosensors, the antibody bioreceptors bind the target of interest and then are visualized by binding a secondary antibody labeled with radioisotopes or conjugated to an enzyme such as horseradish peroxidase that catalyzes a chemiluminescence reaction that can be visualized with photographic film or appropriate photometric sensor. In one aspect, the invention relates to an antibody biosensor because refractometry in the absence of a secondary antibody can detect the primary antibody binding the target due to a change in the refractive index caused by the binding event, for example due to a change in polarizability of the target.

Accordingly, in a further aspect, the invention relates to a free-solution analytical method for detecting molecular interactions comprising the steps of: (a) providing a refractive index sensor for reception of a fluid sample to be analyzed; (b) introducing a first sample comprising a first non-immobilized analyte to be analyzed and a second sample comprising a second non-immobilized analyte to be analyzed onto the sensor, wherein the first analyte is allowed to interact with the second analyte; (c) interrogating the fluid sample with light; and (d) detecting the light after interaction with the fluid sample, wherein the detected light is not backscattered, wherein the method is employed to detect a target of interest in the absence of a second antibody. In a further aspect, the detected light is not scattered.

In an even further aspect, the method further comprises the steps of: (a) introducing a reference sample; (b) interrogating the reference sample with light; (c) detecting the light after interaction with the reference sample, wherein the detected light is not backscattered; (d) determining a characteristic of the reference sample; and (e) employing the characteristic of the reference sample to compensate for background interference effects in the determination of the molecular interaction between the first and second analyte in the first channel. The reference sample can be introduced, for example, onto the refractive index sensor. In a further aspect, the reference sample can be introduced into a channel. In a still further aspect, the reference sample can be introduced into the first channel. In yet a further aspect, the reference sample can be introduced into the second channel.

In a further aspect, the invention relates to a free-solution analytical method for detecting molecular interactions comprising the step of detecting a molecular interaction between two non-immobilized analytes, wherein at least one of the analytes is present in the sample during the determination at a concentration of less than about $5.0 \times 10^{-4}$ M, wherein the method is employed to detect a target of interest in the absence of a second antibody.

In a further aspect, the invention relates to a free-solution analytical method for detecting molecular interactions comprising the step of detecting a molecular interaction between two non-immobilized analytes, wherein at least one of the analytes is present during the determination in a solution with a volume in the detection zone of less than about 500 nL, wherein the method is employed to detect a target of interest in the absence of a second antibody.

In a further aspect, the invention relates to a free-solution analytical method for detecting molecular interactions comprising the steps of: (a) providing a refractive index sensor for reception of a fluid sample to be analyzed; (b) introducing a reference sample; (c) establishing a baseline interferometric response by interrogating the reference sample with light; (d) introducing a first sample comprising a mixture of a first non-immobilized analyte and a second non-immobilized analyte to be analyzed, wherein the first analyte is allowed to interact with the second analyte, onto the sensor; (e) interrogating the fluid sample with light; and (f) detecting the light after interaction with the fluid sample, wherein the detected light is not backscattered, wherein the method is employed to detect a target of interest in the absence of a second antibody.

2. Nucleic Acid Biosensors

In conventional nucleic acid biosensors, the specific sequence of bases that define a segment of DNA can be used as a probe to bind other DNA sequences, and these DNA sequences can be labeled with radioactive or other labels. In one aspect, the invention relates to a DNA biosensor because refractometry in the absence of a labeled secondary DNA probe can detect the primary DNA binding the target DNA due to a change in the refractive index caused by the binding event.

Accordingly, in a further aspect, the invention relates to a free-solution analytical method for detecting molecular interactions comprising the steps of: (a) providing a refractive index sensor for reception of a fluid sample to be analyzed; (b) introducing a first sample comprising a first non-immobilized analyte to be analyzed and a second sample comprising a second non-immobilized analyte to be analyzed onto the sensor, wherein the first analyte is allowed to interact with the second analyte; (c) interrogating the fluid sample with light; and (d) detecting the light after interaction with the fluid sample, wherein the detected light is not backscattered, wherein the method is employed to detect a DNA sequence of interest in the absence of a labeled secondary DNA probe.

In an even further aspect, the method further comprises the steps of: (a) introducing a reference sample; (b) interrogating the reference sample with light; (c) detecting the light after interaction with the reference sample, wherein the detected light is not backscattered; (d) determining a characteristic of the reference sample; and (e) employing the characteristic of the reference sample to compensate for background interference effects in the determination of the molecular interaction between the first and second analyte in the first channel. In a further aspect, the detected light is not scattered.

The reference sample can be introduced, for example, onto the refractive index sensor. In a further aspect, the reference sample can be introduced into a channel. In a still further aspect, the reference sample can be introduced into the first channel. In yet a further aspect, the reference sample can be introduced into the second channel.

In a further aspect, the invention relates to a free-solution analytical method for detecting molecular interactions comprising the step of detecting a molecular interaction between two non-immobilized analytes, wherein at least one of the analytes is present during the determination at a concentration of less than about $5.0 \times 10^{-4}$ M, wherein the method is employed to detect a DNA sequence of interest in the absence of a labeled secondary DNA probe.

In a further aspect, the invention relates to a free-solution analytical method for detecting molecular interactions comprising the step of detecting a molecular interaction between two non-immobilized analytes, wherein at least one of the analytes is present during the determination in a solution with a volume in the detection zone of less than about 500 nL, wherein the method is employed to detect a DNA sequence of interest in the absence of a labeled secondary DNA probe.

In a further aspect, the invention relates to a free-solution analytical method for detecting molecular interactions comprising the steps of: (a) providing a refractive index sensor for reception of a fluid sample to be analyzed; (b) introducing a reference sample; (c) establishing a baseline interferometric response by interrogating the reference sample with light; (d) introducing a first sample comprising a mixture of a first non-immobilized analyte and a second non-immobilized analyte to be analyzed, wherein the first analyte is allowed to interact with the second analyte, onto the sensor; (e) interrogating the fluid sample with light; and (f) detecting the light after interaction with the fluid sample, wherein the detected light is not backscattered, wherein the method is employed to detect a DNA sequence of interest in the absence of a labeled secondary DNA probe.

3. Enzyme Biosensors

In conventional enzyme biosensors, the presence or absence of substrate molecules can be determined by measuring the production of the enzymatic reaction end products. In one aspect, the invention relates to an enzyme biosensor because refractometry can be used to measure the amount of the initial substrate or the enzymatic reaction end products as long as they are binding a molecular species where the binding can be detected by a change in the refractive index of the solution.

Accordingly, in a further aspect, the invention relates to a free-solution analytical method for detecting molecular interactions comprising the steps of: (a) providing a refractive index sensor for reception of a fluid sample to be analyzed; (b) introducing a first sample comprising a first non-immobilized analyte to be analyzed and a second sample comprising a second non-immobilized analyte to be analyzed onto the sensor, wherein the first analyte is allowed to interact with the second analyte; (c) interrogating the fluid sample with light; and (d) detecting the light after interaction with the fluid sample, wherein the detected light is not backscattered, wherein the method is employed to measure the production of the enzymatic reaction end products in the absence of specifically modified recombinant GBP including a fluorescent probe. In a further aspect, the detected light is not scattered.

In an even further aspect, the method further comprises the steps of: (a) introducing a reference sample; (b) interrogating the reference sample with light; (c) detecting the light after interaction with the reference sample, wherein the detected light is not backscattered; (d) determining a characteristic of the reference sample; and (e) employing the characteristic of the reference sample to compensate for background interference effects in the determination of the molecular interaction between the first and second analyte in the first channel. The reference sample can be introduced, for example, onto the refractive index sensor. In a further aspect, the reference sample can be introduced into a channel. In a still further aspect, the reference sample can be introduced into the first channel. In yet a further aspect, the reference sample can be introduced into the second channel.

In a further aspect, the invention relates to a free-solution analytical method for detecting molecular interactions comprising the step of detecting a molecular interaction between two non-immobilized analytes, wherein at least one of the analytes is present during the determination at a concentration of less than about $5.0 \times 10^{-4}$ M, wherein the method is employed to measure the production of the enzymatic reaction end products in the absence of specifically modified recombinant GBP including a fluorescent probe.

In a further aspect, the invention relates to a free-solution analytical method for detecting molecular interactions comprising the step of detecting a molecular interaction between two non-immobilized analytes, wherein at least one of the analytes is present during the determination in a solution with a volume in the detection zone of less than about 500 nL, wherein the method is employed to measure the production of the enzymatic reaction end products in the absence of specifically modified recombinant GBP including a fluorescent probe.

In a further aspect, the invention relates to a free-solution analytical method for detecting molecular interactions comprising the steps of: (a) providing a refractive index sensor for reception of a fluid sample to be analyzed; (b) introducing a reference sample; (c) establishing a baseline interferometric response by interrogating the reference sample with light; (d) introducing a first sample comprising a mixture of a first non-immobilized analyte and a second non-immobilized analyte to be analyzed, wherein the first analyte is allowed to interact with the second analyte, onto the sensor; (e) interrogating the fluid sample with light; and (f) detecting the light after interaction with the fluid sample, wherein the detected light is not backscattered, wherein the method is employed to measure the production of the enzymatic reaction end products in the absence of specifically modified recombinant GBP including a fluorescent probe.

4. Cellular Biosensors

In conventional cellular biosensors, the presence or absence of substrate molecules can be measured by measuring cellular metabolism, cell respiration, or bacterial bioluminescence. In one aspect, the invention relates to a cellular biosensor because refractometry can be used to measure the amount of the initial substrate as long as it is binding a molecular species where the binding can be detected by a change in the refractive index of the solution.

Accordingly, in a further aspect, the invention relates to a free-solution analytical method for detecting molecular interactions comprising the steps of: (a) providing a refractive index sensor for reception of a fluid sample to be analyzed; (b) introducing a first sample comprising a first non-immobilized analyte to be analyzed and a second sample comprising a second non-immobilized analyte to be analyzed onto the sensor, wherein the first analyte is allowed to interact with the second analyte; (c) interrogating the fluid sample with light; and (d) detecting the light after interaction with the fluid sample, wherein the detected light is not backscattered, wherein the method is employed to directly assay an analyte of interest in the absence of genetically engineered bacteria. In a further aspect, the detected light is not scattered.

In an even further aspect, the method further comprises the steps of: (a) introducing a reference sample; (b) interrogating the reference sample with light; (c) detecting the light after interaction with the reference sample, wherein the detected light is not backscattered; (d) determining a characteristic of the reference sample; and (e) employing the characteristic of the reference sample to compensate for background interference effects in the determination of the molecular interaction between the first and second analyte in the first channel. The reference sample can be introduced, for example, onto the refractive index sensor. In a further aspect, the reference sample can be introduced into a channel. In a still further aspect, the reference sample can be introduced into the first channel. In yet a further aspect, the reference sample can be introduced into the second channel.

In a further aspect, the invention relates to a free-solution analytical method for detecting molecular interactions comprising the step of detecting a molecular interaction between two non-immobilized analytes, wherein at least one of the analytes is present during the determination at a concentration of less than about $5.0 \times 10^{-4}$ M, wherein the method is employed to directly assay an analyte of interest in the absence of genetically engineered bacteria.

In a further aspect, the invention relates to a free-solution analytical method for detecting molecular interactions comprising the step of detecting a molecular interaction between two non-immobilized analytes, wherein at least one of the analytes is present during the determination in a solution with a volume in the detection zone of less than about 500 nL, wherein the method is employed to directly assay an analyte of interest in the absence of genetically engineered bacteria.

In a further aspect, the invention relates to a free-solution analytical method for detecting molecular interactions comprising the steps of: (a) providing a refractive index sensor for reception of a fluid sample to be analyzed; (b) introducing a reference sample; (c) establishing a baseline interferometric response by interrogating the reference sample with light; (d) introducing a first sample comprising a mixture of a first non-immobilized analyte and a second non-immobilized analyte to be analyzed, wherein the first analyte is allowed to interact with the second analyte, onto the sensor; (e) interrogating the fluid sample with light; and (f) detecting the light after interaction with the fluid sample, wherein the detected light is not backscattered, wherein the method is employed to directly assay an analyte of interest in the absence of genetically engineered bacteria.

5. Measurement of End-Point Values

In one aspect, refractometry can measure end-point values of phase (which is a measure of the change in RI when using an interferometer) for the reaction between molecule A and molecule B as a function of the concentration of molecule B to determine the binding affinity of the complex and/or to quantitatively determine the concentration of the A-B product at reaction equilibrium. End-point concentration bioassays can be used in both research and clinical diagnostic applications.

In one aspect, the disclosed methods and systems can be used to perform semi-quantitative end-point measurements. A calibration curve for a first analyte (e.g., antibody) at a known concentration can be generated by measuring the response to interaction between the first analyte and a second analyte (e.g., antigen) at systematically varied known concentrations. Comparison of a subsequent response measured when an unknown concentration of the second analyte is allowed to interact (e.g., antibody-antigen binding, aptamer binding, etc.) with a known concentration of the first analyte to the calibration curve yields the concentration of the second analyte in the sample analyzed. Amount of the second analyte in the sample can then be determined as a function of sample volume.

Thus, in one aspect, the end point of the interaction between a first non-immobilized analyte and a second non-immobilized analyte can be determined by a free-solution analytical method for detecting molecular interactions comprising the steps of: (a) providing a refractive index sensor for reception of a fluid sample to be analyzed; (b) introducing a first sample comprising a first non-immobilized analyte to be analyzed and a second sample comprising a second non-immobilized analyte to be analyzed onto the sensor, wherein the first analyte is allowed to interact with the second analyte; (c) interrogating the fluid sample with light; and (d) detecting the light after interaction with the fluid sample, wherein the detected light is not backscattered. In a further aspect, the detected light is not scattered.

In an even further aspect, the method further comprises the steps of: (a) introducing a reference sample; (b) interrogating the reference sample with light; (c) detecting the light after interaction with the reference sample, wherein the detected light is not backscattered; (d) determining a characteristic of the reference sample; and (e) employing the characteristic of the reference sample to compensate for background interference effects in the determination of the molecular interaction between the first and second analyte in the first channel. The reference sample can be introduced, for example, onto the refractive index sensor. In a further aspect, the reference sample can be introduced into a channel. In a still further aspect, the reference sample can be introduced into the first channel. In yet a further aspect, the reference sample can be introduced into the second channel.

In one aspect, the end point of the interaction between a first non-immobilized analyte and a second non-immobilized analyte can be determined by a free-solution analytical method for detecting molecular interactions comprising the step of detecting a molecular interaction between two non-immobilized analytes, wherein at least one of the analytes is present during the determination at a concentration of less than about $5.0 \times 10^{-4}$ M.

In one aspect, the end point of the interaction between a first non-immobilized analyte and a second non-immobilized analyte can be determined by a free-solution analytical method for detecting molecular interactions comprising the step of detecting a molecular interaction between two non-immobilized analytes, wherein at least one of the analytes is present during the determination in a solution with a volume in the detection zone of less than about 500 nL.

In a further aspect, the first and second analytes can be combined prior to introduction. That is, the analytes can be combined (and thus can potentially interact) prior to performing the disclosed methods. In this aspect, the step of introducing the first analyte and the step of introducing the second analyte are performed simultaneously.

Alternatively, in a further aspect, the first and second analytes are combined after introduction. That is, the analytes can be combined at a point before the sensor, or at a point on the sensor, when performing the disclosed methods. In this aspect, the step of introducing the first analyte and the step of introducing the second analyte are performed either simultaneously or sequentially. In a further aspect, the detecting step is performed during the interaction of the first analyte with the second analyte.

6. Determination of Kinetic Parameters

In a further aspect, refractometry can determine kinetic parameters. That is, the refractometry techniques described herein can be used to monitor various kinetic parameters, such as, for example, binding affinities, of a chemical and/or biochemical analyte species. The use of refractometry for the determination of a kinetic parameter can provide one or more advantages over traditional techniques, for example, free-solution measurements of label-free species, high throughput, small sample volume, high sensitivity, and broad dynamic range. A refractometry technique can be performed on a free-solution species, a surface immobilized species, or a combination thereof. In one aspect, the species of interest is a free-solution species, wherein at least a portion of the species of interest is not bound or otherwise immobilized. In another aspect, at least a portion of the species of interest is surface immobilized.

In one aspect, a refractometry technique can be used to analyze and/or quantify one or more molecular interactions, such as, for example, a dissociation constant for one or more binding pair species. Such a binding pair species can be, in various aspects, a protein-protein, peptide-protein, small molecule-protein, ion-protein, or an antibody-antigen pair. Other reactions and/or molecular interactions can be likewise analyzed via refractometry and the present invention is not intended to be limited to the specific binding pairs and/or reactions recited herein.

The sensitivity of a refractometry technique can allow analysis and/or determination of at least one kinetic parameter to be performed on a small volume sample. The volume of a sample comprising at least one species of interest can, in various aspects, be less than about 1 nL, for example, about 900, 850, 800, 700, 600, 500, 400, 350, 300, 250, or 200 pL; less than about 600 pL, for example, about 580, 550, 500, 450, 400, 350, 300, 250, or 200 pL; or less than about 400 pL, for example, about 390, 380, 370, 360, 350, 340, 330, 320, 310, 300, 280, 250, 230, or 200 pL. In one aspect, the sample volume is about 500 pL. In another aspect, the sample volume is about 350 pL. The sample volume can also be greater than or less than the volumes described above, depending on the concentration of a species of interest and the design of a particular refractometry apparatus. A species that can be analyzed via refractometry can be present in neat form, in diluted form, such as, for example, in a dilute solution, or any other form suitable for analysis by a refractometry technique. The concentration of a species of interest can likewise vary depending upon, for example, the design of a particular refractometry apparatus, the volume of sample in the optical path, the intensity of a response of a specific species to the radiation used in the experiment. In various aspects, the species can be present at a concentration of from about 1 fM to greater than 100 mM.

Analysis of a kinetic parameter via a refractometry technique can be performed on a static sample, a flowing sample, for example, 75-120 μL/min, or a combination thereof. In one aspect, an analysis can be a stop-flow determination that can allow an estimation of the dissociation constant ($K_D$) of one or more binding pairs of species. The speed at which one or more samples can be analyzed can be dependent upon, inter alia, the data acquisition and/or processing speed of the detector element and/or processing electronics. Methods for adjusting the throughput speed of a refractometry apparatus, such as signal multiplexing, can be utilized and are considered to be included in various aspects of the present invention.

An apparatus for analyzing a kinetic parameter using a refractometry technique can comprise an optical system and a sample comprising the one or more species of interest. The optical system can comprise, a laser, such as, for example, a HeNe laser, and a detector, such as, for example, a CCD array detector, such as a high resolution linear CCD. In one aspect, the detector is a CCD bar code scanner.

In various aspects, the sample can be positioned on a refractive index sensor. Thus, in a further aspect, the sample can be positioned on a prism. In a still further aspect, the sample can be positioned in or on a channel, such as, for example, a microfluidic channel on a poly(dimethylsiloxane) chip. A microfluidic channel, if present, can comprise a pattern, such as, for example, a serpentine flow pattern, and/or a mixing zone, such as, for example, a squeeze. In a specific aspect, the sample can be positioned in a rectangular channel approximately 50 μm by 70 μm. In such a specific aspect, the sample can be irradiated with a 100 μm diameter He—Ne laser beam to yield an optical sample volume of approximately 350 pL. In other various aspects, a microfluidic channel, if present, can be semicircular or cylindrical, such as, for example, a fused silica capillary, and the present invention is not intended to be limited to any particular microfluidic channel geometry.

A microfluidic channel, if present, can comprise one or multiple channels that can hold and/or transport the same or varying samples, and a mixing zone. The design of a mixing zone can allow at least initial mixing of, for example, one or more binding pair species. The at least initially mixed sample can then be subjected to a stop-flow analysis, provided that the reaction and/or interaction between the binding pair species continues or is not complete at the time of analysis. The specific design of a microfluidic channel, mixing zone, and the conditions of mixing can vary, depending on such factors as, for example, the concentration, response, and volume of a sample and/or species.

The concentration of one or more analyte species in a sample can be determined with a refractometry technique by, for example, monitoring the refractive index of a sample solution comprising an analyte species. A property, such as, for example, refractive index, can be measured in real-time and the kinetics of an interaction between analyte species determined therefrom. Other experimental conditions, such as, for example, temperature and pH, can optionally be controlled during analysis. The number of real-time data points acquired for determination of a kinetic parameter can vary based on, for example, the acquisition rate and the desired precision of a resulting kinetic parameter. The length of time of a specific experiment should be sufficient to allow acquisition of at least the minimal number of data points to calculate and/or determine a kinetic parameter. In one aspect, an experiment can be performed in about 60 seconds.

An apparent binding affinity between binding pair species can subsequently be extracted from the acquired data using conventional kinetics models and/or calculations. In one aspect, a model assumes first order kinetics (a single mode binding) and the observed rate ($k_{obs}$) can be plotted versus the concentration of one of the species. A desired kinetic parameter, such as, for example, $K_D$, can be determined by, for example, a least squares analysis of the relationship plotted above. A suitable fitting model can be selected based on the particular experimental condition such that a rate approximation can be determined at the end of the analysis. One of skill in the art can readily select an appropriate model or calculation to determine a particular kinetic parameter from data obtained via refractometry analysis.

7. Immobilized Bait Measurements

In a further aspect, refractometry can measure immobilized bait measurements. The bait can be one of two interacting species, and, in conventional immobilized bait measurements, the bait is immobilized at a surface of the analysis system, wherein the interaction and analysis occur.

In contrast, the disclosed methods can involve free-solution measurements. The disclosed methods, however, can be used to interrogate analytes that are non-immobilized, yet bound. That is, the analyte can be selectively bound to another species, yet neither analyte is immobilized at a surface of the analysis system. More specifically, the bait can be bound upon a substrate that is introduced as a free solution with respect to the detection zone. For example, the bait could be immobilized in a micelle, upon a nanoparticle, or within a cell membrane fragment. As further examples, the disclosed systems and methods can be applied to molecules embedded in micelles, cell membrane segments, intact cells, and/or nanoparticles with derivatized surfaces.

Analogously, one binding partner can be bound upon a nano- or microsupport that can then be analyzed within the disclosed systems under free solution conditions by using the disclosed methods.

As a further example, an analyte can be bound to a magnetic particle and delivered (or held) by magnetic fields at a desired detection zone within a larger system (e.g., a biological system such as an organism).

In a further example, one or more of the interacting analytes can be bound by "tether" to a surface of the system within the detection zone. Another, free-solution analyte can then be allowed to interact with the bound analyte, thereby forming one or more interaction products, which can remain bound via the tether or can be released into free solution. The tether can be, for example, attachment via covalent bond or other strong interaction. The attachment directly to the surface, attachment via a relatively short tether (e.g., functionalized alkyl chain, oligomer, or self-assembled monolayer) or via a long tether (e.g., functionalized alkyl chain or polymer—potentially hundreds or thousands of nanometers in length).

In conventional techniques, a first analyte is attached to a surface (e.g., via tether attachment). The attachment is typically followed by a wash step to remove remaining unattached first analyte from the sample or detection zone; this wash can be necessary to eliminate or minimize any interaction due to non-immobilized first analyte. The wash step is followed by the addition of a second analyte, which interacts with the immobilized first analyte to form one or more immobilized interaction products. In conventional techniques, this step is followed by a second wash step to remove remaining non-interacted second analyte from the sample or detection zone; this wash can be necessary to eliminate or minimize any interaction due to non-interacted second analyte. In contrast, in the disclosed methods the second wash step can be unnecessary, as the signal observed in response to the formation and presence of the one or more interaction products is strong relative to any response due unreacted analytes. Similarly, if the proper control or reference is used for comparison the second wash step may be unnecessary. Thus, the disclosed methods can be performed for the analysis of interaction between an immobilized or tethered analyte and a non-immobilized analyte while omitting the second wash step.

Accordingly, in a further aspect, the invention relates to a free-solution analytical method for detecting molecular interactions comprising the steps of: (a) providing a refractive index sensor for reception of a fluid sample to be analyzed; (b) introducing a first sample comprising a first non-immobilized analyte to be analyzed and a second sample comprising a second non-immobilized analyte to be analyzed onto the sensor, wherein the first analyte is allowed to interact with the second analyte; (c) interrogating the fluid sample with light; and (d) detecting the light after interaction with the fluid sample, wherein the detected light is not backscattered, wherein the method is employed to investigate non-immobilized, yet bound analytes.

In an even further aspect, the method further comprises the steps of: (a) introducing a reference sample; (b) interrogating the reference sample with light; (c) detecting the light after interaction with the reference sample, wherein the detected light is not backscattered; (d) determining a characteristic of the reference sample; and (e) employing the characteristic of the reference sample to compensate for background interference effects in the determination of the molecular interaction between the first and second analyte in the first channel. In a further aspect, the detected light is not scattered.

The reference sample can be introduced, for example, onto the refractive index sensor. In a further aspect, the reference sample can be introduced into a channel. In a still further aspect, the reference sample can be introduced into the first channel. In yet a further aspect, the reference sample can be introduced into the second channel.

Accordingly, in a further aspect, the invention relates to a free-solution analytical method for detecting molecular interactions comprising the step of detecting a molecular interaction between two non-immobilized analytes, wherein at least one of the analytes is present during the determination at a concentration of less than about $5.0 \times 10^{-4}$ M, wherein the method is employed to investigate non-immobilized, yet bound analytes.

Accordingly, in a further aspect, the invention relates to a free-solution analytical method for detecting molecular interactions comprising the step of detecting a molecular interaction between two non-immobilized analytes, wherein at least one of the analytes is present during the determination in a solution with a volume in the detection zone of less than about 500 nL, wherein the method is employed to investigate non-immobilized, yet bound analytes.

In a further aspect, the invention relates to a free-solution analytical method for detecting molecular interactions comprising the steps of: (a) providing a refractive index sensor for reception of a fluid sample to be analyzed; (b) introducing a reference sample; (c) establishing a baseline interferometric response by interrogating the reference sample with light; (d) introducing a first sample comprising a mixture of a first non-immobilized analyte and a second non-immobilized analyte to be analyzed, wherein the first analyte is allowed to interact with the second analyte, onto the sensor; (e) interrogating the fluid sample with light; and (f) detecting the light after interaction with the fluid sample, wherein the detected light is not backscattered, wherein the method is employed to investigate non-immobilized, yet bound analytes.

8. Free Solution Measurements

In a further aspect, refractometry can measure free solution measurements. Conventional methods typically require measuring the amount of bound analyte by for example Western blotting that requires tethering a protein to a solid support, binding the antibody, and then binding a secondary antibody that has a label attached to it for visualization. In contrast, the disclosed refractometry method does not require that the protein being examined be bound to a solid support, as the measurement could be made in free solution.

Other surface-bound biosensor techniques can be supplanted by the disclosed free-solution methods and systems. For example, the objective of surface plasmon resonance (SPR), optical wave-guide techniques, grating coupled optical waveguide techniques, micro-cantilever techniques, atomic force microscopy, acoustic techniques, as well as labeled techniques (including chemiluminescence, ELISA, fluorescence detection, and solid or liquid scintillation) can be achieved with the disclosed systems and methods.

Accordingly, in a further aspect, the invention relates to a free-solution analytical method for detecting molecular interactions comprising the steps of: (a) providing a refractive index sensor for reception of a fluid sample to be analyzed; (b) introducing a first sample comprising a first non-immobilized analyte to be analyzed and a second sample comprising a second non-immobilized analyte to be analyzed onto the sensor, wherein the first analyte is allowed to interact with the second analyte; (c) interrogating the fluid sample with light; and (d) detecting the light after interaction with the fluid sample, wherein the detected light is not backscattered. In a further aspect, the detected light is not scattered.

In an even further aspect, the method further comprises the steps of: (a) introducing a reference sample; (b) interrogating the reference sample with light; (c) detecting the light after interaction with the reference sample, wherein the detected light is not backscattered; (d) determining a characteristic of the reference sample; and (e) employing the characteristic of the reference sample to compensate for background interference effects in the determination of the molecular interaction between the first and second analyte in the first channel. The reference sample can be introduced, for example, onto the refractive index sensor. In a further aspect, the reference sample can be introduced into a channel. In a still further aspect, the reference sample can be introduced into the first channel. In yet a further aspect, the reference sample can be introduced into the second channel.

In a further aspect, the invention relates to a free-solution analytical method for detecting molecular interactions comprising the step of detecting a molecular interaction between two non-immobilized analytes, wherein at least one of the analytes is present during the determination at a concentration of less than about $5.0 \times 10^{-4}$ M.

In a further aspect, the invention relates to a free-solution analytical method for detecting molecular interactions comprising the step of detecting a molecular interaction between two non-immobilized analytes, wherein at least one of the analytes is present during the determination in a solution with a volume in the detection zone of less than about 500 nL.

In a further aspect, the invention relates to a free-solution analytical method for detecting molecular interactions comprising the steps of: (a) providing a refractive index sensor for reception of a fluid sample to be analyzed; (b) introducing a reference sample; (c) establishing a baseline interferometric response by interrogating the reference sample with light; (d) introducing a second sample comprising a mixture of a first non-immobilized analyte and a second non-immobilized analyte to be analyzed, wherein the first analyte is allowed to interact with the second analyte, onto the sensor; (e) interrogating the fluid sample with light; and (f) detecting the light after interaction with the fluid sample, wherein the detected light is not backscattered.

9. Label-Free Molecular Interactions

In a further aspect, refractometry can measure label-free molecular interactions. One example of a label-free measurement in life science applications can be when the RI instrument is used to interrogate the binding of two biological macromolecules, such as a DNA binding protein and the fragment of DNA that contains the sequence that the protein binds by examining a change in the interference pattern produced from the reflection and refraction of the solution upon mixing the two biological macromolecules. In contrast, conventional methods require DNA oligonucleotides to be immobilized prior to measuring the binding of a single-stranded DNA binding protein which was visualized using surface plasmon resonance (1999 JACS Brockman et al., 121:8044-51). In contrast, the disclosed refractometry method does not require that the protein being examined be labeled or be bound to a solid support, since the measurement could be made in free solution In a further aspect, refractometry can measure classes of biomolecular interaction studies as described herein. As used herein, proteins includes glycoproteins, lectins, peptides, antibodies, protein antibody mimetic and any antibody subclasses including SCFV, Fab, Fc, or molecular imprints (MIP). In a further aspect of the invention, the biomolecular interaction is an interaction of a protein with a protein. In a further of the invention, the biomolecular interaction is an interaction of an antibody with an antigen. In a further aspect of the invention, the biomolecular interaction is an interaction of an enzyme and a substrate. In a further aspect of the invention, the biomolecular interaction is an interaction of a protein and a virus. As used herein, virus includes phage. In a further aspect of the invention, the biomolecular interaction is an interaction of a receptor and a ligand. In a further aspect of the invention, the biomolecular interaction is an interaction of a protein and a carbohydrate. In a further aspect of the invention, the biomolecular interaction is an interaction of a protein and a nucleic acid. As used herein, nucleic acid includes DNA, RNA, and aptamers. In a further aspect of the invention, the biomolecular interaction is an interaction of a receptor and a ligand. In a further aspect of the invention, the biomolecular interaction is an interaction of a nucleic acid with a nucleic acid. In a further aspect of the invention, the biomolecular interaction is an interaction of a small molecule with a protein. In a further aspect of the invention, the biomolecular interaction is an interaction of a small molecule with a nucleic acid. In a further aspect of the invention, the biomolecular interaction is an interaction of a small molecule with a receptor. In a further aspect of the invention, the biomolecular interaction is an interaction of a small molecule and a carbohydrate. In a further aspect of the invention, the biomolecular interaction is an interaction of a small molecule and a virus. In a further aspect of the invention, the biomolecular interaction is an interaction of a small molecule with a small molecule. In a further aspect of the invention, the biomolecular interaction is an interaction of a cell with a protein. In a further aspect of the invention, the biomolecular interaction is an interaction of a cell with a carbohydrate. In a further aspect of the invention, the biomolecular interaction is an interaction of a cell with a cell. In a further aspect of the invention, the biomolecular interaction is an interaction of a cell with a small molecule. In a further aspect of the invention, the biomolecular interaction is an interaction of a cell with a nucleic acid. In a further aspect of the invention, the biomolecular interaction is an interaction of a cell with a virus.

Accordingly, in a further aspect, the invention relates to a free-solution analytical method for detecting molecular interactions comprising the steps of: (a) providing a refractive index sensor for reception of a fluid sample to be analyzed; (b) introducing a first sample comprising a first non-immobilized analyte to be analyzed and a second sample comprising a second non-immobilized analyte to be analyzed onto the sensor, wherein the first analyte is allowed to interact with the second analyte; (c) interrogating the fluid sample with light; and (d) detecting the light after interaction with the fluid sample, wherein the detected light is not backscattered, wherein the method is employed to measure one or more characteristic properties and/or chemical events of unlabelled (i.e., substantially label-free) analytes. In a further aspect, the detected light is not scattered.

In an even further aspect, the method further comprises the steps of: (a) introducing a reference sample; (b) interrogating the reference sample with light; (c) detecting the light after interaction with the reference sample, wherein the detected light is not backscattered; (d) determining a characteristic of the reference sample; and (e) employing the characteristic of the reference sample to compensate for background interference effects in the determination of the molecular interaction between the first and second analyte in the first channel. The reference sample can be introduced, for example, onto the refractive index sensor. In a further aspect, the reference sample can be introduced into a channel. In a still further aspect, the reference sample can be introduced into the first channel. In yet a further aspect, the reference sample can be introduced into the second channel.

In a further aspect, the invention relates to a free-solution analytical method for detecting molecular interactions comprising the step of detecting a molecular interaction between two non-immobilized analytes, wherein at least one of the analytes is present during the determination at a concentration of less than about $5.0 \times 10^{-4}$ M, wherein the method is employed to measure one or more characteristic properties and/or chemical events of unlabelled (i.e., substantially label-free) analytes.

In a further aspect, the invention relates to a free-solution analytical method for detecting molecular interactions comprising the step of detecting a molecular interaction between two non-immobilized analytes, wherein at least one of the analytes is present during the determination in a solution with a volume in the detection zone of less than about 500 nL, wherein the method is employed to measure one or more characteristic properties and/or chemical events of unlabelled (i.e., substantially label-free) analytes.

In a further aspect, the invention relates to a free-solution analytical method for detecting molecular interactions comprising the steps of: (a) providing a refractive index sensor for reception of a fluid sample to be analyzed; (b) introducing a reference sample; (c) establishing a baseline interferometric response by interrogating the reference sample with light; (d) introducing a first sample comprising a mixture of a first non-immobilized analyte and a second non-immobilized analyte to be analyzed, wherein the first analyte is allowed to interact with the second analyte, onto the sensor; (e) interrogating the fluid sample with light; and (f) detecting the light after interaction with the fluid sample, wherein the detected light is not backscattered, wherein the method is employed to measure one or more characteristic properties and/or chemical events of unlabelled (i.e., substantially label-free) analytes.

For the detection of biomolecular interactions, the following types of detectors can be replaced or can be able to be used in combination with refractometry, including optical techniques including Surface enhanced Raman spectroscopy, Surface Plasmon Resonance (SPR), and Biolayer Interferometry (BLI). SPR is an optical phenomenon used for measuring molecular interactions but requires that one molecular species be immobilized. The SPR signal arises in thin metal films and the signal depends on the refractive index of solutions in contact with the metal surface. A challenging aspect of using SPR is the dependence on the relative mass of the binding partners. For example, measuring a small molecule in solution binding a large, immobilized protein is quite difficult. Direct immobilization of one of the molecular species without disrupting its binding activity is an additional challenge. In contrast to SPR, refractometry can be used to measure the binding of macromolecules without either macromolecule being fixed to a surface. For example, using SPR, it was recently shown that soluble monomeric beta-amyloid peptides can bind anti-beta-amyloid monoclonal antibodies (J Phys Chem B 2007; 111: 1238-43). In contrast, refractometry can also be used to measure soluble monomeric beta-amyloid peptides binding an anti-beta-amyloid monoclonal antibodies in free solution. An additional challenge of SPR is the dependence on relative mass of the binding partners. For example, measuring a small molecule in solution binding a large, immobilized protein can be extremely difficult.

A further type of detector that can be replaced or used in combination with refractometry is one that utilizes grating based approaches such as optical waveguide lightmode spectroscopy (OWLS). OWLS measures the surface immobilization of biomolecules in an aqueous solution. The technique is based on the incoupling of a laser into a waveguide by an optical grating. The incoupling only occurs at two defined angles that are sensitive to a change in the refractive index above the surface in the evanescent field. The OWLS method uses the change in the refractive index to measure the adsorbed mass. A challenging aspect of using OWLS is direct immobilization of one of the molecular species. In contrast to OWLS, refractometry can be used to measure the binding of macromolecules without either macromolecule being fixed to a surface. For example, using OWLS, the interaction between mycotoxins and anti-mycotoxin monoclonal antibodies was measured (Biosens Bioelectron 2007 22:797-802). In contrast, RI can also be used to measure the binding of soluble mycotoxins binding anti-mycotoxin monoclonal antibodies in free solution.

A further type of detector that can be replaced or used in combination with refractometry is one that utilizes mass-sensitive measurements such as surface acoustic wave (SAW). In SAW, small mass changes can be measured that result from molecules binding the receptor molecules coupled to the active sensor surface. Small mass changes at the sensor surface affects the propagation velocity of acoustic shear waves traveling through a guiding layer at the sensor surface. A challenging aspect of using SAW is direct immobilization of one of the molecular species. In contrast to SAW, refractometry can be used to measure the binding of macromolecules without either macromolecule being fixed to a surface. For example, using SAW, the interaction between bovine immunoglobulin G and Protein A was recently measured (International Conference on Solid State Sensors and Actuators Jun. 16-19 1997 1:187-190). In contrast, refractometry can also be used to measure the binding of bovine immunoglobulin G and Protein A in free solution.

A further type of detector that can be replaced or used in combination with refractometry is one that utilizes mass-sensitive measurements utilizing a piezoelectric crystal. For example, small mass changes can be measured that result from molecules binding the receptor molecules coupled to the active sensor surface due to a change in the oscillation frequency of a piezoelectric crystal. Piezoelectric crystals oscillate as a function of both the electrical frequency applied to the crystal and the crystal's mass. Small mass changes can therefore be measured electrically. In contrast to a microbalance, refractometry can be used to measure the binding of macromolecules without either macromolecule being fixed to a surface. For example, using a piezoelectric crystal, the interaction between Staphylococcal Enterotoxin B (SEB) and anti-SEB polyclonal antibodies was measured (Biosens Bioelectron 1997 12:661-7). In contrast, refractometry can also be used to measure the binding of Staphylococcal Enterotoxin B and anti-SEB polyclonal antibodies in free solution.

10. Electrochemical Measurements

A further type of detector that can be replaced or used in combination with refractometry is one that utilizes electrochemical measurements. For example, one electrochemical biosensor can detect L-phenylalanine via activity of three immobilized enzymes. The three enzymes are immobilized on an electrode wherein first L-phenylalanine dehydrogenase binds and reacts with L-phenylalanine producing NADH. Then salicylate hydroxylase uses oxygen and NADH to convert salicylate to catechol. Then tyrosinase oxidizes catechol to o-quinone which is reduced back to catechol with an electrode potential of −50 mV (Anal Commun 1999 36:281). In contrast to the electrochemical biosensor, refractometry can be used to directly measure the presence of L-phenylalanine by its binding to another macromolecule in free solution.

Accordingly, in a further aspect, the invention relates to a free-solution analytical method for determination of molecular interactions comprising the steps of: (a) providing a refractive index sensor for reception of a fluid sample to be analyzed; (b) introducing a first sample comprising a first non-immobilized analyte to be analyzed and a second sample comprising a second non-immobilized analyte to be analyzed onto the sensor, wherein the first analyte is allowed to interact with the second analyte; (c) interrogating the fluid sample with light; and (d) detecting the light after interaction with the fluid sample, wherein the detected light is not backscattered, wherein the method is employed to directly assay an analyte of interest in the absence of one or more specially modified enzymes, or an enzyme cascade. In a further aspect, the detected light is not scattered.

In an even further aspect, the method further comprises the steps of: (a) introducing a reference sample; (b) interrogating the reference sample with light; (c) detecting the light after interaction with the reference sample, wherein the detected light is not backscattered; (d) determining a characteristic of the reference sample; and (e) employing the characteristic of the reference sample to compensate for background interference effects in the determination of the molecular interaction between the first and second analyte in the first channel. The reference sample can be introduced, for example, onto the refractive index sensor. In a further aspect, the reference sample can be introduced into a channel. In a still further aspect, the reference sample can be introduced into the first channel. In yet a further aspect, the reference sample can be introduced into the second channel.

In a further aspect, the invention relates to a free-solution analytical method for detecting molecular interactions comprising the step of detecting a molecular interaction between two non-immobilized analytes, wherein at least one of the analytes is present during the determination at a concentration of less than about $5.0 \times 10^{-4}$ M, wherein the method is employed to directly assay an analyte of interest in the absence of one or more specially modified enzymes, or an enzyme cascade.

In a further aspect, the invention relates to a free-solution analytical method for detecting molecular interactions comprising the step of detecting a molecular interaction between two non-immobilized analytes, wherein at least one of the analytes is present during the determination in a solution with a volume in the detection zone of less than about 500 nL, wherein the method is employed to directly assay an analyte of interest in the absence of one or more specially modified enzymes, or an enzyme cascade.

In a further aspect, the invention relates to a free-solution analytical method for detecting molecular interactions comprising the steps of: (a) providing a refractive index sensor for reception of a fluid sample to be analyzed; (b) introducing a reference sample; (c) establishing a baseline interferometric response by interrogating the reference sample with light; (d) introducing a first sample comprising a mixture of a first non-immobilized analyte and a second non-immobilized analyte to be analyzed, wherein the first analyte is allowed to interact with the second analyte, onto the sensor; (e) interrogating the fluid sample with light; and (f) detecting the light after interaction with the fluid sample, wherein the detected light is not backscattered, wherein the method is employed to directly assay an analyte of interest in the absence of one or more specially modified enzymes, or an enzyme cascade.

11. Atomic Force Microscopy

A further type of detector that can be replaced or used in combination with refractometry is one that utilizes atomic force microscopy (AFM). AFM utilizes the deflection of a microscale cantilever by forces such as electrostatic or Van Der Waal etc. in order to scan a specimen at the nanometer scale. The technique can be used to image, measure or manipulate matter. For example, AFM has been used to measure the dissociation rate constants of aptamer protein complexes (Chem Asian J 2007 2:284-9). In contrast to AFM, refractometry can be used to measure equilibrium dissociation rate constants of aptamer protein complexes in free solution.

12. End User Applications

Refractometry can be used in any market where measuring macromolecular interactions is desired. In basic life science research, better understanding of how proteins interact with one another in the complex networks that form biochemical and genetic regulatory pathways can lead to a better understanding of new potential intervention points.

For example, improperly functioning networks, due to inherited or somatic genetic mutations, can be probed with the disclosed methods.

Drug discovery and development, as well as translational research, can also greatly benefit from the disclosed invention, because it offers alternatives for analysis wherein therapeutics bind a target molecule, thereby enabling further development of drug candidates. Modifications to drug candidates can also be assessed using refractometry as a tool to determine binding properties to the target of interest. Strong and specific binding can be important for effective therapeutics. Moreover, understandings of which biomarkers are useful for predicting drug efficacy can benefit from tests for their presence in patients, as well as tests that help elucidate their basic biochemical and physiologic properties. It is contemplated that the disclosed invention can facilitate drug discovery, drug development, and translational research.

In the food industry, as well as in biodefense applications, a rapid methodology that can assay for the presence of toxins, xenobiotics, allergens, additives, or biowarfare agents whether chemicals, viruses, or cellular pathogens such as certain bacteria can be useful as evidenced today by a large number of such items for which no easy to use tests are readily available today. It is contemplated that the disclosed invention can find utility in food industry and biodefense applications.

The disclosed invention can also be used in clinical diagnostics for early diagnosis of disease, monitoring disease progression, measurement of drug response to disease, and other applications of personalized medicine diagnostics, such as determining optimum drug dosage or drug for each individual based on diagnostic testing.

I. Experimental

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

1. Modeling and Background

In 1991 a group from Pharmacia (Stenberg et al. (1991) Quantitative-Determination of Surface Concentration of Protein with Surface-Plasmon Resonance Using Radiolabeled Proteins. *J Colloid Interf Sci* 143(2):513-526) showed SPR response was linear with surface concentration of protein (ng/mm$^2$) for adsorbed species, and introduced the refractive index increment (RII), which was defined as dη/dC in mL/g. They further illustrated that the RI of the surface layer was:

$$\eta_{layer} = \eta_{liquid} + (d\eta/dC)_{dextran} C_{dextran} + (d\eta/dC)_{protein} C_{protein} \quad (1)$$

In addition, the thickness of the protein at the surface, represented by a closely packed protein crystal was calculated. In the absence of values for solvent content and specific volume, they used Matthews report (Matthews, B. W. (1977) *The Proteins III*, (Academic Press, New York), pp 403-590) that indicated the fractional solvent content for globular protein crystals ranged from 30-78% to show the extreme values gave a surface thickness range of 60 and 200 nm.

Others have expanded on these observations. In 1998 Sinclair Yee and co-workers (Jung L S, Campbell C T, Chinowsky T M, Mar M N, & Yee S S (1998) Quantitative Interpretation of the Response of Surface Plasmon Resonance Sensors to Adsorbed Films. *Langmuir* 14(19):5636-5648) showed that the Lorenz-Lorenz equation can be reduced to:

$$\eta_{soln} = f_j \eta_j + f_k \eta_k = f_j(\eta_j - \eta_k) + \eta_k \quad (2)$$

where f is the volume fraction of the species. Using a literature derived value for protein specific volume (Darnell et al. (1990) *Molecular Cell Biology* (Scientific American Books, New York; Leslie and Lilley (1985) Aqueous-Solutions Containing Amino-Acids and Peptides 0.20. Volumetric Behavior of Some Terminally Substituted Amino-Acids and Peptides at 298.15 K. *Biopolymers* 24(4):695-710) (0.77 mL/g) in Eq 2, Yee showed that $\eta_{protein} - \eta_{buffer} = 0.234$ RIU. They noted: "since in those solutions $\eta_{buffer} = 1.336$ RIU, [we obtain] $\eta_{protein} = 1.57$ RIU for the water-free (unreacted) protein. This value is very close to the index of refraction measured for crystalline proteins of 1.60 RIU, a finding confirmed by Schuck (Zhao et al. (2011) On the Distribution of Protein Refractive Index Increments. *Biophys J* 100(9): 2309-2317). Importantly these values are greater than those estimated for "adsorbed protein films" using ellipsometric approaches assuming a single optical thickness, since the film volume includes a great deal of water (Jung et al. (1998) Quantitative Interpretation of the Response of Surface Plasmon Resonance Sensors to Adsorbed Films. *Langmuir* 14(19):5636-5648). Yee et. al. referred to that part of the film that "are made of protein material itself, not water." They also noted that it is believed that "this approach, which neglects the intermixed solvent in the adlayer, is more direct and general for quantitative analysis of adsorbate coverages for proteins and adsorbates in general" (Jung et al. (1998) Quantitative Interpretation of the Response of Surface Plasmon Resonance Sensors to Adsorbed Films. *Langmuir* 14(19):5636-5648). It was also reported that the volume of a functional group can be estimated from its geometry (bond lengths, angles) and van der Waals radii of its atoms, or can it can be treated as a parameter and determined by fitting the equation to known RIs. One can also measure $\eta_a$ in cases where very thick adlayers can be grown. By simply measuring the maximum response for an infinitely thick ($\gg l_d$) adlayer, one gets $R_{max} = m(\eta_a - \eta_s)$. Since the slope of the calibration plot, m, and the RI of the solvent are known, one can solve for $\eta_a$.

As noted in the paper, in 2000 Davis and Wilson reported on an approach to determine the RII of small molecules to correct SPR data (Davis and Wilson (2000) Determination of the refractive index increments of small molecules for correction of surface plasmon resonance data. *Anal Biochem* 284(2):348-353). They too employed the formalism:

$$RU_{obs} = \eta^* X = X[(\delta\eta/\delta C)_{ligand} C] \quad (3)$$

where $RU_{obs}$ is the observed instrument response in resonance units after blank subtraction, η is the refractive index at the surface which increases as ligand binds to immobilized macromolecule, X is a factor to convert η to $RU_{obs}$, $(\delta\eta/\delta C)_{ligand}$ is the refractive index increment (RII) of the bound ligand, and C is the concentration of ligand bound at the biospecific surface in mass/volume. In a plot of Δη versus concentration they showed that the RII range for small molecules can be quite large (0.15-0.34), and that the value measured for the protein BSA corresponded well with literature values of 0.17-0.18. They predicted the maximum SPR instrument (BIACORE) response for binding of a single ligand to be:

$$(RU_{pred})_{max} = RU_{M^*}(MW_L/MW_M)^*(\delta\eta/\delta C)_L/(\delta\eta/\delta C)_M \qquad (4)$$

$(RU_{pred})_{max}$ is the predicted maximum instrument response in resonance units for binding at a single site, $RU_M$ is the experimental amount of macromolecule immobilized on the chip in resonance units, $MW_L$ is the molecular weight of the ligand, $MW_M$ is the molecular weight of the immobilized macromolecule, $(\delta\eta/\delta C)_L/(\delta\eta/\delta C)_M$ is the RII of the macromolecule. Note that the predicted signal is directly proportional to the relative mass of the binding pair.

Shortly after this report, a group in Brazil (Tumolo et al. (2004) Determination of the refractive index increment (dn/dc) of molecule and macromolecule solutions by surface plasmon resonance. *Anal Biochem* 333(2):273-279) showed that flow injection gradient SPR systems exhibit the same response as previously reported and that the expression:

$$C_{ligand} = \Delta\theta/X(\delta\eta/\delta C)_{ligand} \qquad (5)$$

could be used to determine the RII of the ligand/molecule and macromolecule solutions, where C is concentration of molecules adsorbing over surfaces, ΔΘ shift detected and X is the instrument calibration constant.

The existing paradigm described above is based on a model that defines the response for RI sensing methods as being proportional to the mass or concentration weighted change in RI. Critically, this supposition does not take into account the possibility that signal change may be impacted by significant conformation and hydration changes upon chemical or biochemical transformation (e.g., folding, binding, changes in waters of hydration, electrostatic or electronic redistribution, etc.).

a. The Free-Solution Signal in the Absence of a Mass Change

Figures 4A, 4B:
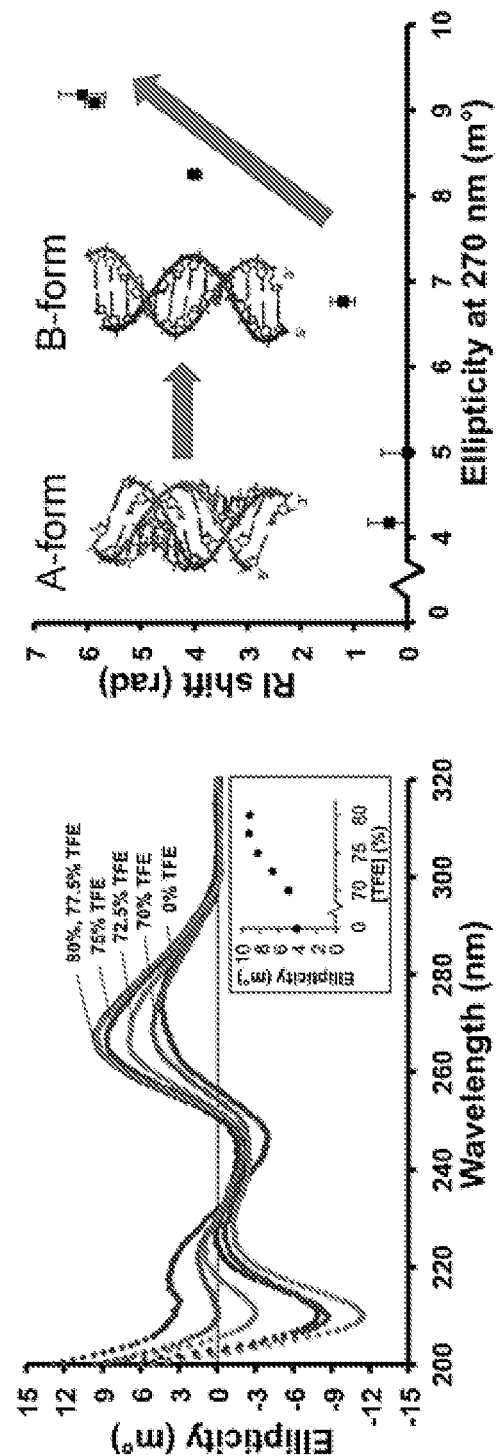
FIG. 4A and FIG. 4B show representative data illustrating the A-form to B-form transition of the DNA duplex. Specifically.

Using the titration and incubation DNA:DNA duplexes with trifluroethanol (TFE), an established method for converting the duplex structure (Ivanov et al. (1974) Bbar to Abar Transition of DNA in Solution. *J Mol Biol* 87(4):817-833; Kypr J, Kejnovska I, Renciuk D, & Vorlickova M (2009) Circular dichroism and conformational polymorphism of DNA. *Nucleic Acids Res* 37(6):1713-1725), the transition from the B-form to A-form was induced (FIG. 1A and FIG. 1B). Next, these structural transformations were monitored with circular dichroism (CD), ellipticity at 270 nm, and BSI (Adams et al. (2013) The effect of hybridization-induced secondary structure alterations on RNA detection using backscattering interferometry. *Nucleic Acids Res* 41(9):e103). As illustrated in FIG. 4A, the CD analysis confirmed the predicted structural transition in the DNA:DNA duplex. Correcting for the bulk RI change in the solvent, it was also found that, as the DNA:DNA duplex adopted a more A-form, both the ellipticity signal and the free-solution change in RI increased significantly (FIG. 4B). This correlation is of particular importance, because the ellipticity signal reports film thickness and is a widely accepted method to determine conformation changes (Fasman et al. (1970) Conformational Changes Associated with F-1 Histone-Deoxyribonucleic Acid Complexes—Circular Dichroism Studies. *Biochemistry-Us* 9(14):2814). Collectively, the results confirm that the free-solution readout reports a structural transformation in the DNA duplex.

b. Heuristic Model for the Free-Solution Response Function

Figures 5A, 5B:
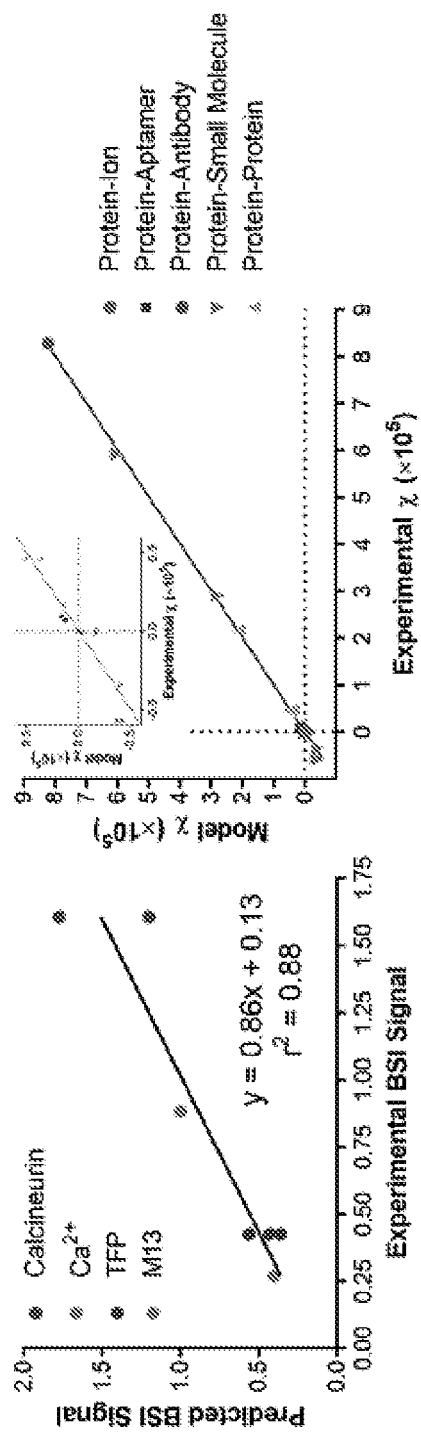
FIG. 5A and FIG. 5B show representative data illustrating the predicted versus BSI experimental values for the CaM binding system (5A) and the correlation of $\chi_{exp}$ and $\chi_{model}$ of the unsegregated learning set (5B).

The first attempt at modeling the free-solution assays was heuristic and based on the assumption that binding-induced change in hydrodynamic radius dominated the signal for CaM interactions. The preliminary calculations utilized the PDB structural information to estimate the radius of gyration ($R_{gyr}$) and solvent accessible surface area (SASA) of the bound and unbound species ($\Delta R_{gyr}$ and ΔSASA). A simple multivariable linear equation was obtained that relates the interferometry signal in phase, to change in $R_{gyr}$ and SASA for the CaM system ($\Delta BSI = 1.0 + 2.6 \times 10^{-4}$ ΔSASA+0.054 $\Delta R_{gyr}$). FIG. 5A shows the correlation between the predicted and experimental values for free-solution interaction studies of CaM binding $Ca^{2+}$, $Ca^{2+}$—CaM-TFP, $Ca^{2+}$—CaM-calcineurin, $Ca^{2+}$—CaM-M13 peptide. Calcineurin-CaM data spread is rather large due to a wide range of values for SASA for structures with close $R_{gyr}$ values. The surprisingly good correlation ($R^2 = 0.88$) between the actual and predicted signal magnitude for these binding events encouraged further investigation.

FIG. 5B presents the results from an unsegregated model, which uses a wide range of χ values (all of those evaluated), but with a modest Spearman correlation coefficient ($\rho_s = 0.853$), a nonparametric measure of statistical dependence between variables indicating that the relationship is not random.

c. Mass Balance Equation Calculations

A binding system's dissociation constant ($K_D$) is related to the concentration of free protein [P], free ligand [A] and bound complex [PA] by the mass-balance equation:

$$K_D = \frac{[P][A]}{[PA]} \qquad (7)$$

Since the total amount of protein and ligand can be defined as:

$$[P]_{total} = [P]_{free} + [PA] \qquad (8)$$

$$[A]_{total} = [A]_{free} + [PA] \qquad (9)$$

these equations can be solved for amount of free protein and free ligand as:

$$[P]_{free} = [P]_{tot} - [PA]$$

$$[A]_{free} = [A]_{tot} - [PA]$$

The equation for $K_D$ can then be rewritten as:

$$K_D = \frac{([P]_{tot} - [PA])([A]_{tot} - [PA])}{[PA]} \qquad (10)$$

This can be rearranged to a quadratic in the following manner:

$$K_D[PA] = ([P]_{tot} - [PA])([A]_{tot} - [PA])$$

$$K_D[PA] = [P]_{tot}[A]_{tot} - [A]_{tot}[PA] - [P]_{tot}[PA] + [PA]^2$$

$$0 = [PA]^2 - [A]_{tot}[PA] - [P]_{tot}[PA] - K_D[PA] + [P]_{tot}[A]_{tot}$$

$$0 = [PA]^2 ([P]_{tot} + [A]_{tot} + K_D)[PA] + [P]_{tot}[A]_{tot} \qquad (11)$$

The concentration [PA] can then be solved for by using the quadratic equation:

$$[PA] = \frac{([P]_{tot} + [A]_{tot} + K_D) \pm \sqrt{([P]_{tot} + [A]_{tot} + K_D)^2 - 4[P]_{tot}[A]_{tot}}}{2} \quad (12)$$

This result will yield two outcomes, only one of which will be physically relevant, which is used to calculate the amount of complex present in a binding assay based upon known concentrations of the protein, ligand, and the $K_D$.

d. Calculation of DN/DC Signal

Here a quantitative comparison of the theoretical convention for predicting/measuring refractive index change for a binding event was performed, as well as for FreeSRF. According to Qain et. al., the mass weighted refractive index increment (RII) for a protein complex is:

$$\frac{d\eta}{dc_{complex}} = (1 - W_r)\frac{d\eta}{dc_{ligand}} + W_r \frac{d\eta}{dc_{receptor}} \quad (13)$$

where $W_r$ is the mass percentage of the receptor in the complex (Qian et al. (1997) Characterization of antigen-antibody complexes by size-exclusion chromatography coupled with low-angle light-scattering photometry and viscometry. *J Chromatogr A* 787(1-2):101-109). For the example calculation the mannose binding to Concanavalin A (ConA) system was used. The refractive index increment (RII) values used were 0.146 mL/g (Tumolo et al. (2004) Determination of the refractive index increment (dn/dc) of molecule and macromolecule solutions by surface plasmon resonance. *Anal Biochem* 333(2):273-279) for mannose and 0.190 mL/g for ConA (Zhao et al. (2011) On the Distribution of Protein Refractive Index Increments. *Biophys J* 100(9):2309-2317). Using a molecular weight for mannose of 180 Daltons and 26.5 kDa for ConA and equation 13, the calculated mass weighted RII for the binding system ($d\eta/dc_{complex}$) is 0.1897 mL/g.

The RII values were then used to predict the refractive index change in both the reference and test sample solutions. The references are samples that do not contain the receptor (ligand alone), so ΔRIU calculated by multiplying the RII by the concentration of ligand (Eq 14).

$$\Delta RIU_{reference} = RII_{ligand} \times [ligand] \quad (14)$$

To calculate the ΔRIU of the test samples, the concentration of product must first be calculated using the mass balance equation as described above (Eqs 7-12). From there the amount of receptor and ligand left in solution can be calculated as:

$$[receptor] = [receptor]_{initial} - [product] \quad (15)$$

$$[ligand] = [ligand]_{initial} - [product] \quad (16)$$

Using these concentration values and the RII's, the maximum ΔRIU of the binding samples can be calculated as:

$$\Delta RIU_{test} = RII_{product} \times [product] + RII_{receptor} \times [receptor] + RII_{ligand} \times [ligand] \quad (17)$$

These values were plotted versus ligand concentration (FIG. 6A-F) and illustrate that, while three of the reference and test samples are predicted to give measurable RI signals using BSI, the ΔRIU for these samples will be very similar.

Figure 6A:
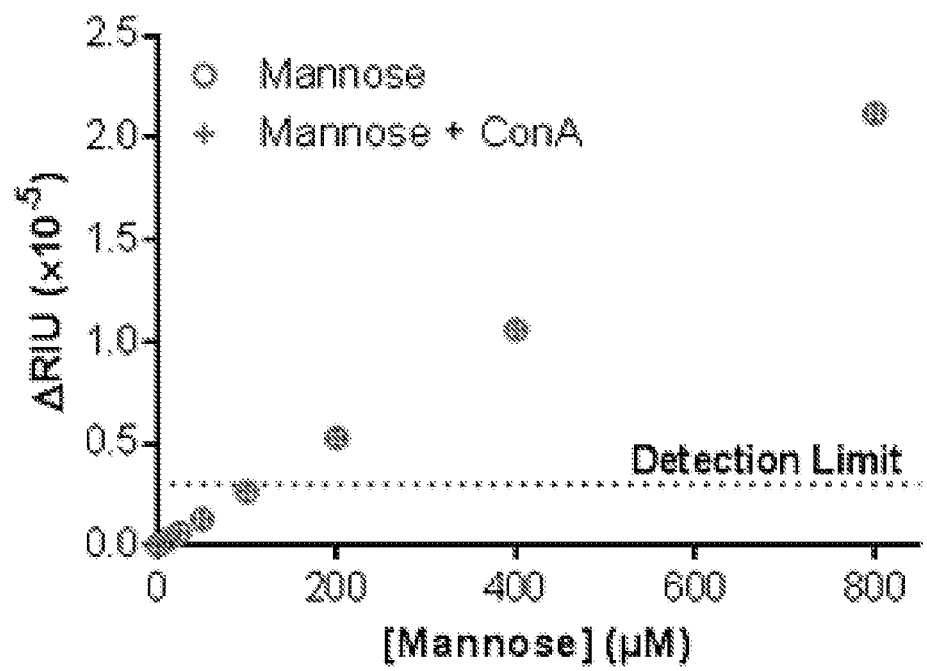
FIG. 6A-F show representative data related to the predicted $d\eta/dc$ ΔRIU. Plots show the calculated $d\eta/dc$ for the reference (o) and test (+) samples for the Concanavalin A-Mannose system (6A) the Calmodulin-Calcineurin system (6D), the predicted $d\eta/dc_{complex}$ signal compared with the experimentally observed signal for ConA-mannose (6B) and c=Calmodulin-calcineurin (6E), and the predicted $d\eta/dc_{complex}$ signal compared with the experimentally observed signal versus product concentration for ConA-mannose (5C) and Calmodulin-calcineurin (6F).
Figure 6B:
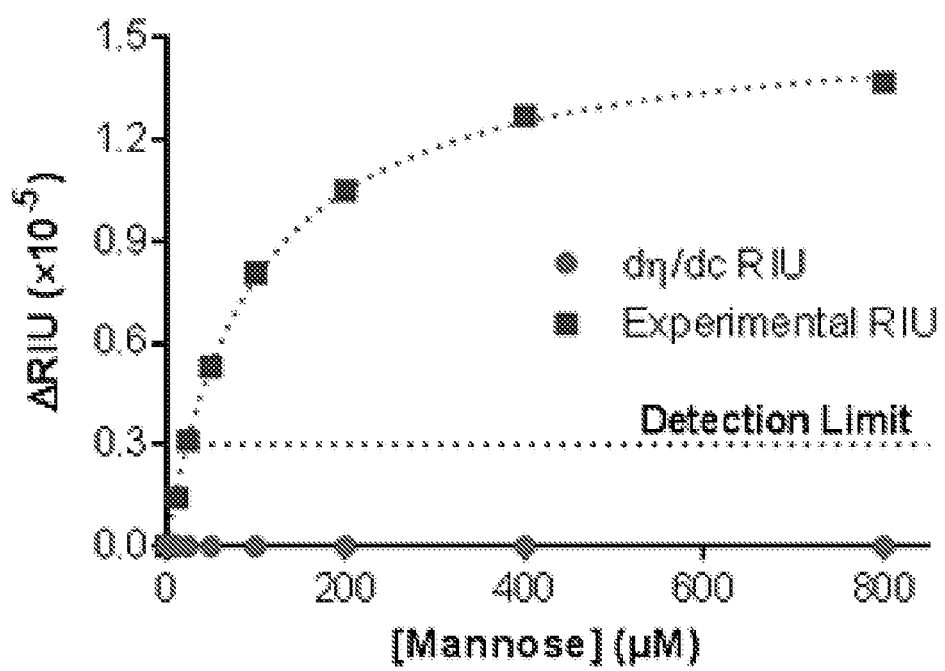
Figure 6C:
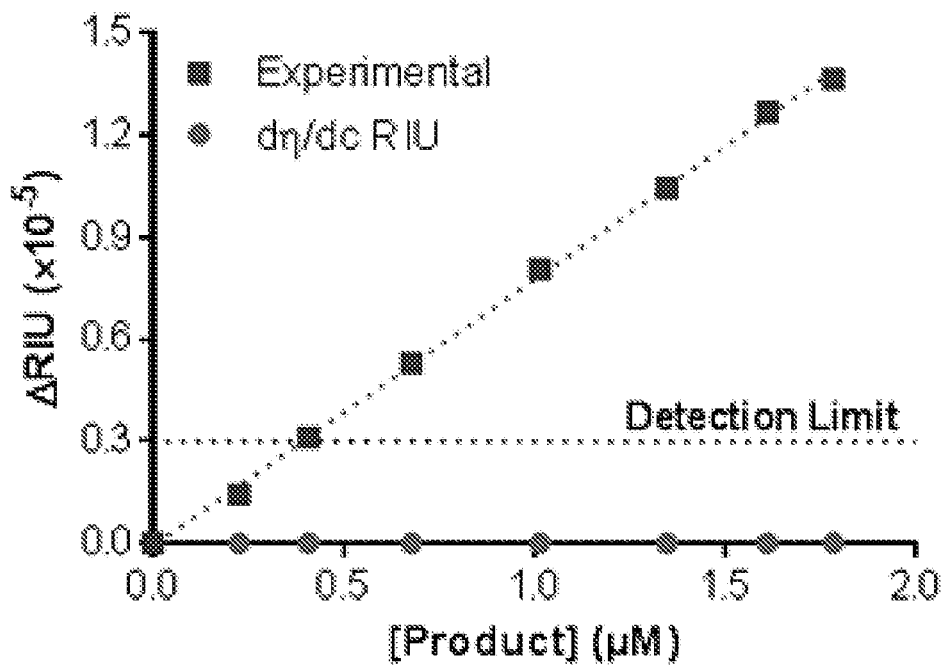

In order to further illustrate this point, the ΔRIU predicted for the $d\eta/dc_{complex}$, which is the difference between the reference and test samples at the same ligand concentration, was plotted versus ligand concentration in FIG. 6B. The plot also presents the experimentally measured binding signal produced by BSI (FIG. 6B), clearly showing the difference in measured signal and that predicted by the currently accepted theory and FreeSRF. This example is in agreement with the statement (Jepsen et al. (2015) Evaluation of back scatter interferometry, a method for detecting protein binding in solution. *Analyst* 140(3):895-901): "that it would be in conflict with the conventional theory to expect a protein binding event would produce a measurable RI change expected by pure do/dc considerations."

Additional calculations are illuminating. For the Mannose-ConA system, the concentration of complex at maximum binding was found to be 1.79 µM (4.76×10$^{-5}$ g/mL) or a maximum ΔRIU of 1.4×10$^{-8}$. This value is considerably below the detection limit of most RI detectors (ca. 10$^{-6}$). In another calculation, the experimental ΔRIU was set equal to the difference between the ΔRIU of the test sample (17) and the ΔRIU of the reference sample (14) at the highest concentration. It was found that the RII of the ConA-mannose complex would need to be 3164.1 mL/g to generate the experimental signal. The RII calculated using the Qain equation predicts a value of 0.1897 mL/g.

Plotting the calculated ΔRIU versus product concentration, along with the actual ΔRIU measured by BSI for this binding event (FIG. 6C), further illustrates the dramatic disconnect between the signal predicted from dη/dc considerations and that measured by this interferometer. In this case, the conventional model predicts a signal that it is 3 orders of magnitude below the experimentally measured ΔRIU.

Figure 6D:
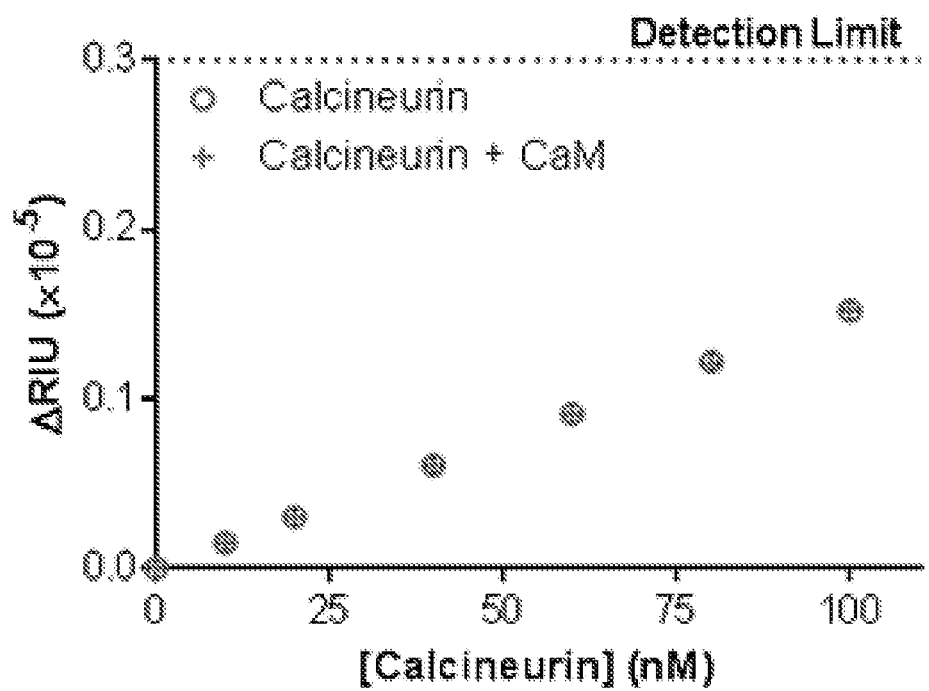
Figure 6E:
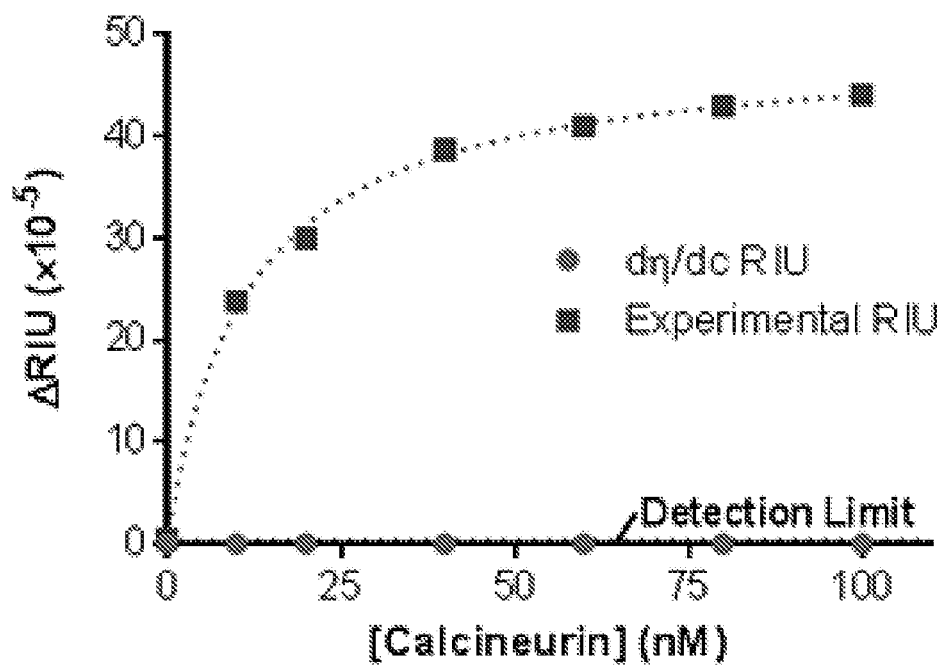
Figure 6F:
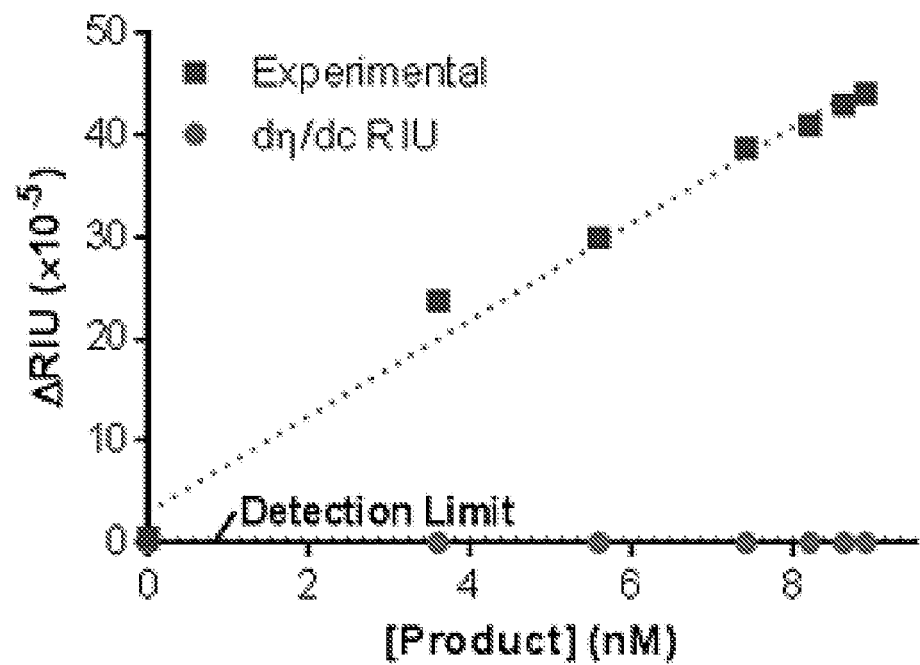

These calculations were repeated for the calmodulin—calcineurin assay. FIG. 6D-F illustrate similar results are obtained for the protein-protein binding pair. Here, even though the ligand is much larger in mass (and absolute RI), the ΔRIU of the reference (calcineurin) and the test samples, (Eqs 14-17), are below the detection limits of the instrument. This result is attributed to the use of considerably lower concentrations of the ligand. As before, the FreeSRF (binding) signal quantified by the interferometer was large and reproducible at ΔRIU (4.41×10$^{-4}$).

Figures 7A, 7B:
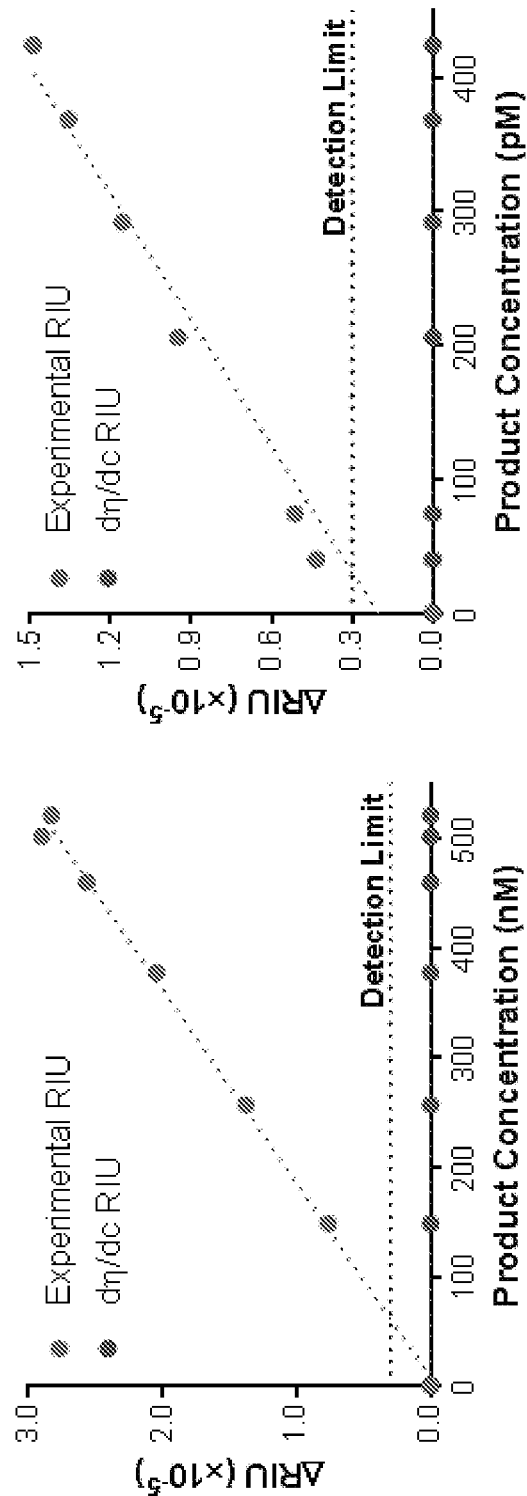
FIG. 7A and FIG. 7B show representative comparisons of experimental and modeled $d\eta/dc$ signal. Specifically, plots showing the experimental BSI signal in RIU with the calculated $d\eta/dc$ signal for recoverin binding $Ca^{2+}$ (7A) and carbonic anhydrase II binding dansylamide (7B).

FIG. 7A and FIG. 7B present the results for performing the calculations shown in Eqs 14-17 for two other binding systems (7A) Recoverin binding Ca$^{2+}$; and (7B) Carbonic Anhydrase II binding dansylamide). According to Zhao et al., large proteins (<10 kDa) exhibit a RII of 0.190 with a Gaussian standard deviation of 0.003 mL/g (Zhao et al. (2011) On the Distribution of Protein Refractive Index Increments. *Biophys J* 100(9):2309-2317), so this value was used for all species that met that criteria. In all cases, a 0.003 mL/g deviation produced minimal change in the final mass weighted refractive index change calculation. This result is principally due to the large differences between the masses of the species. For the small molecule dansylamide, no RII information was available, so the RII of 0.2 mL/g was used, which is a common RII for small molecules. Regardless, no RII value in the range of 0.1 mL/g to 0.5 mL/g produced an RI change large enough to be detected by current RI techniques.

2. Experimental Parameters for Effective Free-Solution Measurements

Figure 8:
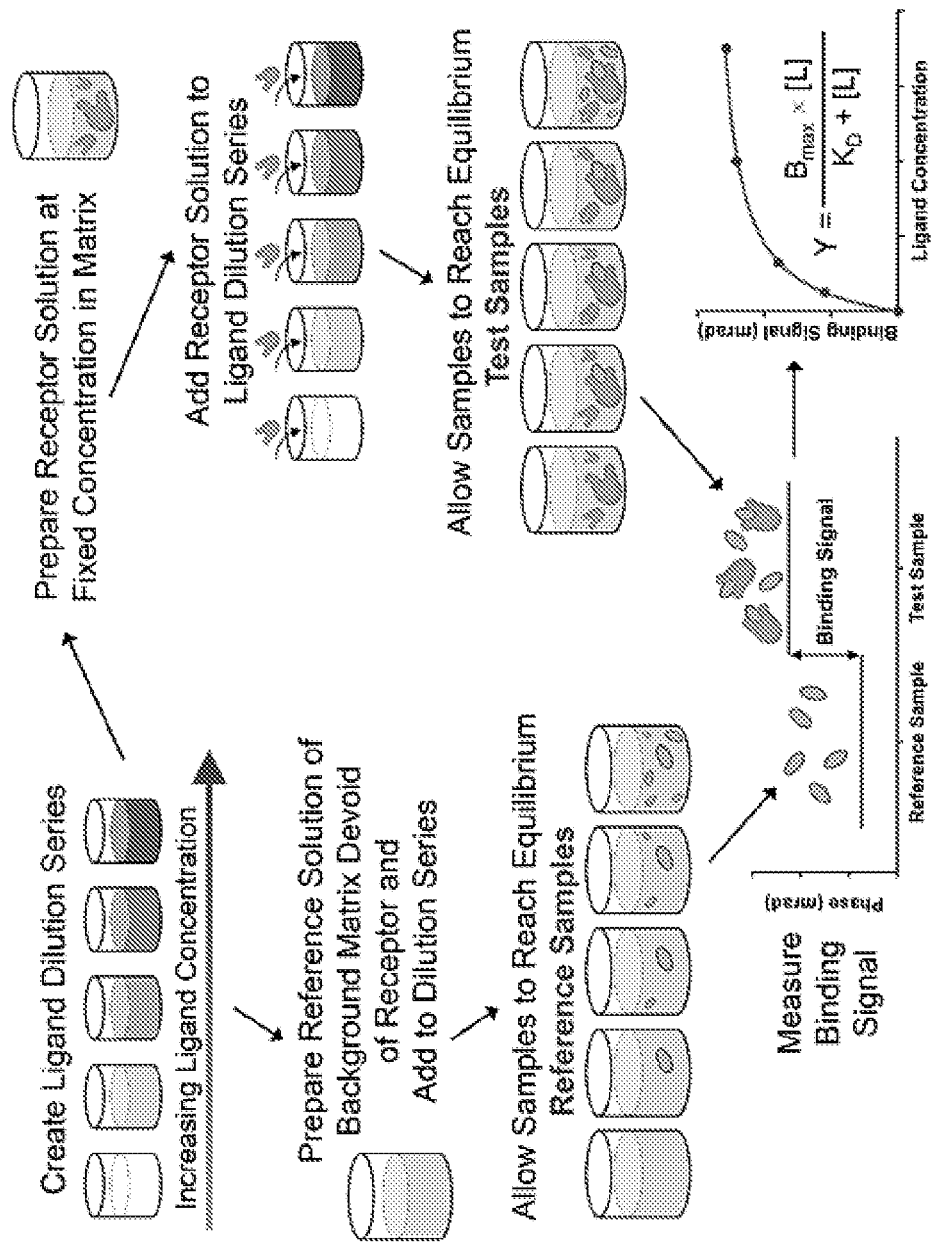
FIG. 8 shows a representative illustration of the procedure for using BSI to measure a binding affinity.

Free-solution assays must be prepared to purposely minimize the difference in RI between the sample and the reference (and/or control). The procedure is illustrated in FIG. 8 and, in short, the sample and reference are prepared from the same matrix (buffer, serum, urine, RBCs, etc.). A fixed concentration solution of the receptor is prepared in the matrix and then combined with the ligand dilution series, which is typically prepared in buffer. Reference solutions are matrix solutions, devoid of the receptor/target that have been combined with the dilution series. For cells, cell- or tissue-derived samples (e.g., vesicles, membrane fractions, lipoparticles, etc.), the reference sample consists of a preparation with the receptor either absent from the matrix or inactivated (expression knocked out, chemically blocked, etc.). Test samples are prepared by combining the dilution series with the receptor-in-matrix solutions. Reference and test samples are then allowed to reach equilibrium, often on ice when proteins are evaluated, and then introduced sequentially into the interferometer. The difference in fringe position (shift) between the reference and test sample reports the binding/interaction in a concentration dependent manner.

In an attempt to enable others to successfully perform free-solution assays with an interferometer and avert reports stating; " . . . we are not able to reproduce the protein A-IgG binding results by Bornhop et al. performed with a reported detection limit of $10^{-6}$ RIU . . . " (Jepsen et al. (2015) Evaluation of back scatter interferometry, a method for detecting protein binding in solution. Analyst 140(3):895-901), it is noted that three conditions are critical to the success of a free solution assay: 1) Care must be taken when preparing the solutions. It is essential that the RI of the sample and reference composition are matched. While it has not been found necessary to dialyze as recommended in ITC (Velazquez-Campoy and Freire (2006) Isothermal titration calorimetry to determine association constants for high-affinity ligands. Nat Protoc 1(1):186-191), the test and reference and/or control samples must be reasonably well index matched. If 2% DMSO is to be used, both the reference and the test solutions must have the same amount (2%) of DMSO. 2) Protein DNA and other types of samples denature over time or can be altered as a consequence of environmental conditions. None have an indefinite shelf life. Free-solution assay reports functional transformations, and the absence of tethering or a surrounding structure like a dextran to orientate the protein, makes it critical they are operational. Even one freeze-thaw cycle or the length and/or environment used during equilibration can impact the performance of the assay. Experience has taught us that the presence of the correct band on a Western is not necessarily an indicator the protein is unadulterated. 3) To insure the signal is not from surface interactions, a baseline is established for the matrix with replicate injections. Then after each consecutive injection, that baseline is reestablished by rinsing the channel prior to collecting the next datum. This procedure helps to ensure that the binding signal is emanating from the change in composition of the solution and not adoption to the walls. Any sample-to-sample baseline excursion would be reporting a change in the optical path length for the interferometer such as the RI of the solution or the effective channel diameter. Channel rinses, and to a lesser extent coatings, serves to improve replicate assay reproducibility by minimizing the contribution of non-specific binding. A wide variety of rinse solutions have been found to be successful, ranging from simply buffer to light acid/base to Piranha, to methanol and chloroform. Since the chip is the optics, the baseline shift from sample to sample can be used to determine if something has been adsorbed to the surface and when it has been removed.

The importance of #3 cannot be over emphasized, since others have questioned the validity of BSI protein binding studies (Jepsen et al. (2015) Evaluation of back scatter interferometry, a method for detecting protein binding in solution. Analyst 140(3):895-901), suggesting that using "channels etched in glass chips . . . could affect protein interactions." It was also stated that, "It is well known that protein adsorbs to . . . surfaces" and since "BSI is sensitive towards RI change of both bulk and surface layers . . . we believe that unspecific binding of proteins could produce erroneous signals." It is true that BSI can detect RI changes in either the bulk or the surface (Latham et al. (2006) Photobiotin surface chemistry improves label-free interferometric sensing of biochemical interactions. Angew Chem Int Edit 45(6):955-958; Markov et al. (2004) Label-free molecular interaction determinations with nanoscale interferometry. J Am Chem Soc 126(50):16659-16664; Sorensen et al. (2006) Highly sensitive biosensing based on interference from light scattering in capillary tubes. Appl Phys Lett 89(15); Kussrow et al. (2009) Measurement of Monovalent and Polyvalent Carbohydrate-Lectin Binding by Back-Scattering Interferometry. Anal Chem 81(12):4889-4897); in fact, this unique property has been employed to compare affinities derived from free-solution and surface-immobilized formats for the same species (Olmsted et al. (2012) Comparison of Free-Solution and Surface-Immobilized Molecular Interactions Using a Single Platform. Anal Chem 84(24):10817-10822; Pesciotta et al. (2011) Back-Scattering Interferometry: A Versatile Platform for the Study of Free-Solution versus Surface-Immobilized Hybridization. Chemistry-an Asian Journal 6(1):70-73). Yet, after >7 years of operation, more than 30 users running numerous blinded samples on multiple different instruments, provide significant evidence that these procedures are enabling free solution measurements.

Concentrations of nM-pM are typically used, a regime where neither the ligand nor the probe exhibits a quantifiable response. In this case, there is no $d\eta/dC$ response expected, yet procedures always include the $d\eta/dC$ determination for a dilution series of the ligand. This procedure allows for compensation of species with higher RI values that would potentially skew the saturation isotherm (Bornhop et al. (2007) Free-solution, label-free molecular interactions studied by back-scattering interferometry. Science 317(5845): 1732-1736; Kussrow A, Enders C S, & Bornhop D J (2012) Interferometric Methods for Label-Free Molecular Interaction Studies. Anal Chem 84(2):779-792).

Free-solution measurements do quantify solution-phase RI changes; thus effective, long-term environmental control is needed to succeed. Since $d\eta/dT$ is large for fluids, temperature control of the sample/chip is required at the level of a couple millidegrees C. Accomplishing this level of thermal stability consists of isolating the optical train, using a high-performance Peltier controller and thermoelectric device (TE), and a chip mount with a large thermal mass and designed to have intimate contact with TE and the chip (Bornhop et al. (2007) Free-solution, label-free molecular interactions studied by back-scattering interferometry. Science 317(5845):1732-1736; Kussrow A, Enders C S, & Bornhop D J (2012) Interferometric Methods for Label-Free Molecular Interaction Studies. Anal Chem 84(2):779-792).

Though sensitivity of RI to pressure ($d\eta/dP$) is about 10-fold less than $d\eta/dT$, pressure perturbations will impact the measurement performance if not constrained. Since end-point assays involve sequentially introducing the samples into a microfluidic channel, often followed by rinses, a somewhat unique injection methodology aimed toward minimizing sample-to-sample pressure ($d\eta/dP$-induced) differences was developed. While effective, simplifying the macro-to-micro interface, while constraining the required volume, has been one of the most challenging aspects of deploying this method into other laboratories. The current manual approach, optimized empirically, works by having a drop dispensed onto the channel inlet and applying a controlled vacuum to the channel outlet for a fixed time period. This semi-automated approach is effective, but still requires the operator to develop injection skills. The level of difficulty is modest, but as with GC injections to this day, manual sample introduction require practice. Repetition and multiple repeats of the assay aid to mitigate the contribution of injection to error in the assay. Improved sample introduction methods are currently under intense investigation.

a. Alignment and Fringe Selection

Figure 9A:
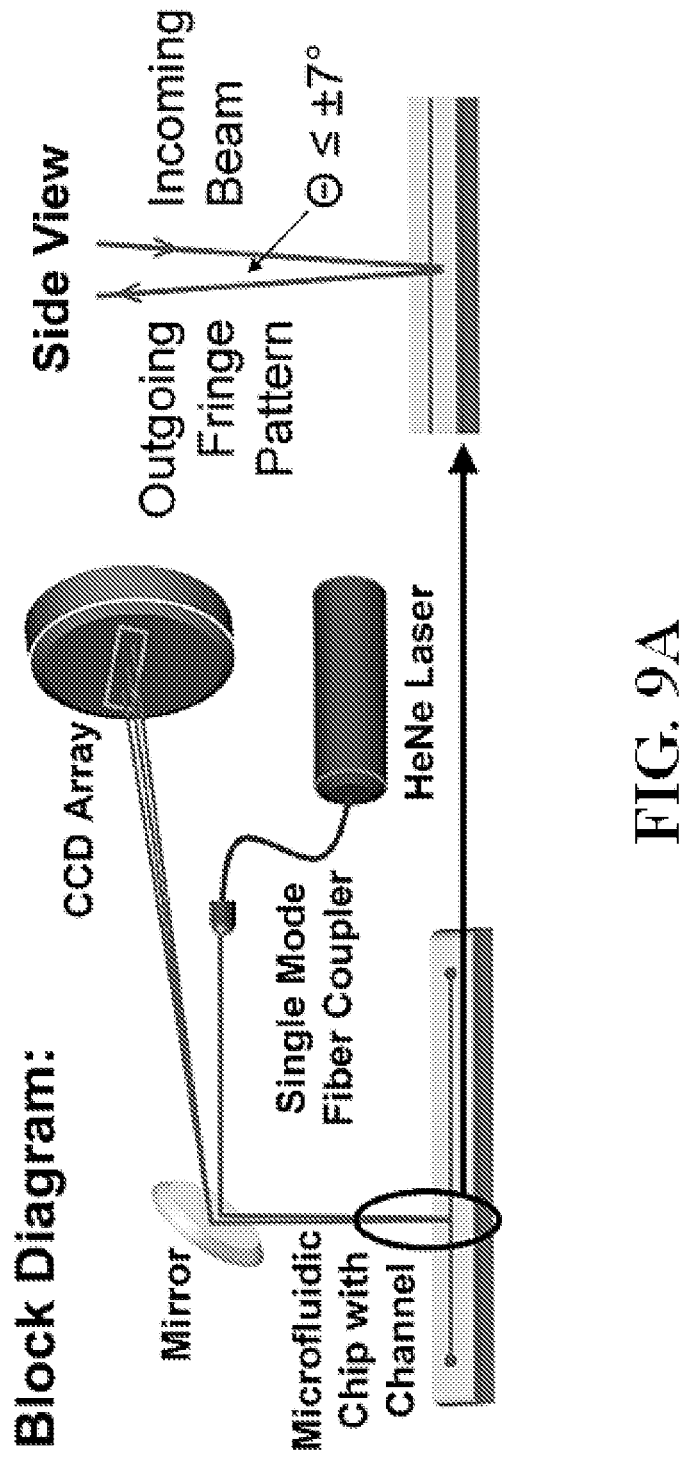
FIG. 9A-F show representative BSI block diagrams showing the orientation of the beam relative to the chip (7A-C), a representative image of the fringe pattern (7D), a representative line profile of the region of interest for a good fringe pattern (7E), and a representative FFT spectrum for that region of interest (ROI) (7F).
Figures 9B, 9C:
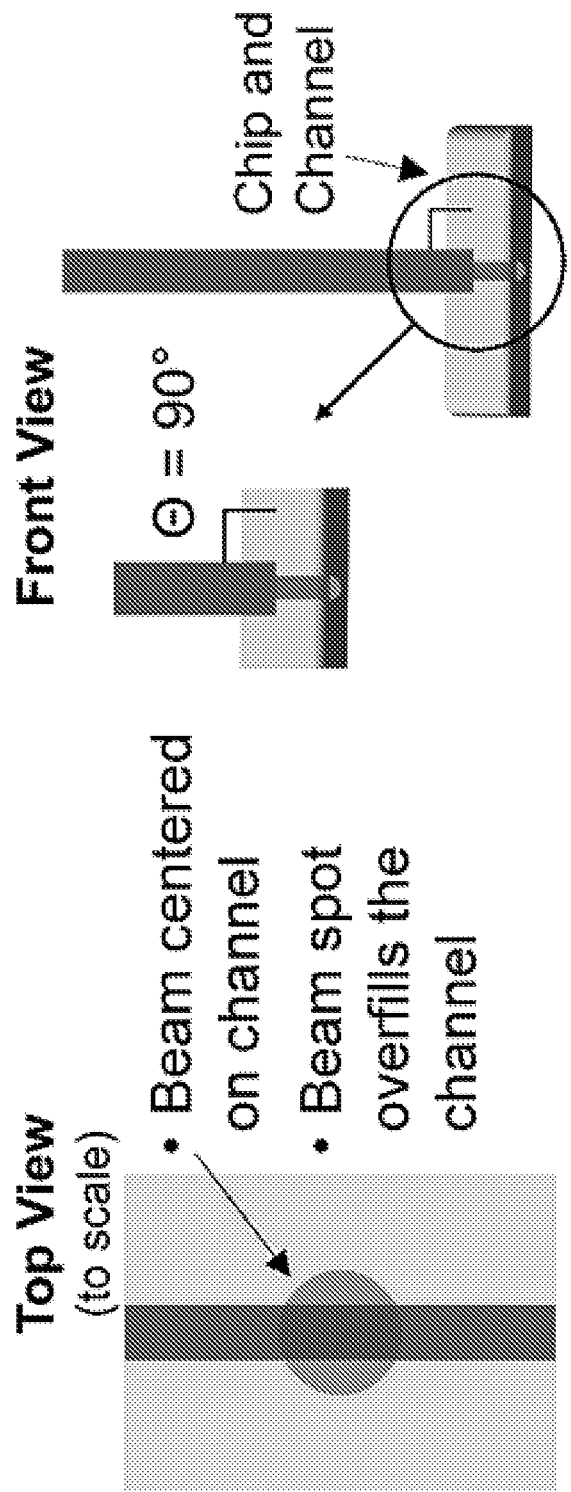

Physics of fringe production and selection are intertwined, because 'poor' alignment is really miss-alignment and leads to a different fringe profile (beam energy distribution). Free-solution assay success with this interferometer is dependent on a general understanding of the optical train that reports the signal. In this interferometer, "the chip is the optics," so in addition to obtaining high-quality chips (Micronit, NL), proper optical alignment is essential. There are several criteria for success and significant deviation from this configuration changes the optical train resulting in fringe patterns different from those characterized. A) The Gaussian laser beam should consist of nearly parallel rays that evenly overfill the channel and impinge on the chip at an angle near to 90° (FIG. 9A-F). The best angle is 90° direct backscatter configuration, but to prevent light reentering the laser cavity and to direct the fringes onto the camera, it has been found that ±7° angle is acceptable. If the chip/capillary is not in maxima of the Gaussian profile the intensity profile will change significantly with different fringes reporting optical path length changes other than those desired. Optimization here is easily accomplished by translating the beam or chip so as to obtain equal intensity on both sides of the centroid. B) Tilt of the incoming beam should be avoided as it leads to a different "object" being interrogated or serving as the interferometer. The result of this type of miss-alignment leads to a different fringe profile with fringes becoming distorted or slanted. C) As reported elsewhere (Bornhop, D. J. (1995) Microvolume Index of Refraction Determinations by Interferometric Backscatter. *Appl Optics* 34(18):3234-3239), placing the object (chip/capillary) in a region of beam divergence or convergence will distort the fringes in a manner similar to adding a modest power lens. This configuration appears to degrade performance using the regions of interest (ROI) previously characterized. D) Fringe quality is also of paramount importance to obtaining high ΔRI performance. Well shaped fringes (FIG. 9D, 9E, and FIG. 10A) having contrast ratios approaching ca. 98% should be obtained for the fringes of interest. Poor contrast indicates reduced interferometer finesse and will result in diminished sensitivity (FIG. 10A and FIG. 10B).

Figure 10A:
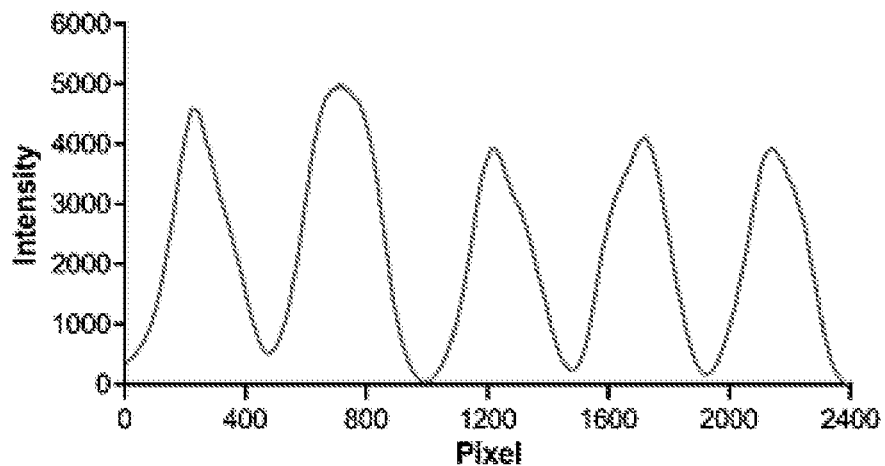
FIG. 10A and FIG. 10B show representative fringe patterns with good (7A) and bad (7B) alignment.
Figure 10B:
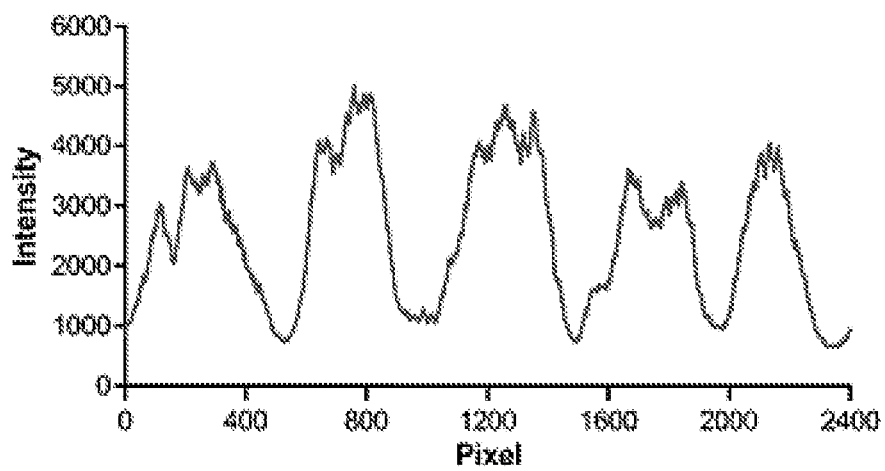
Figure 11A:
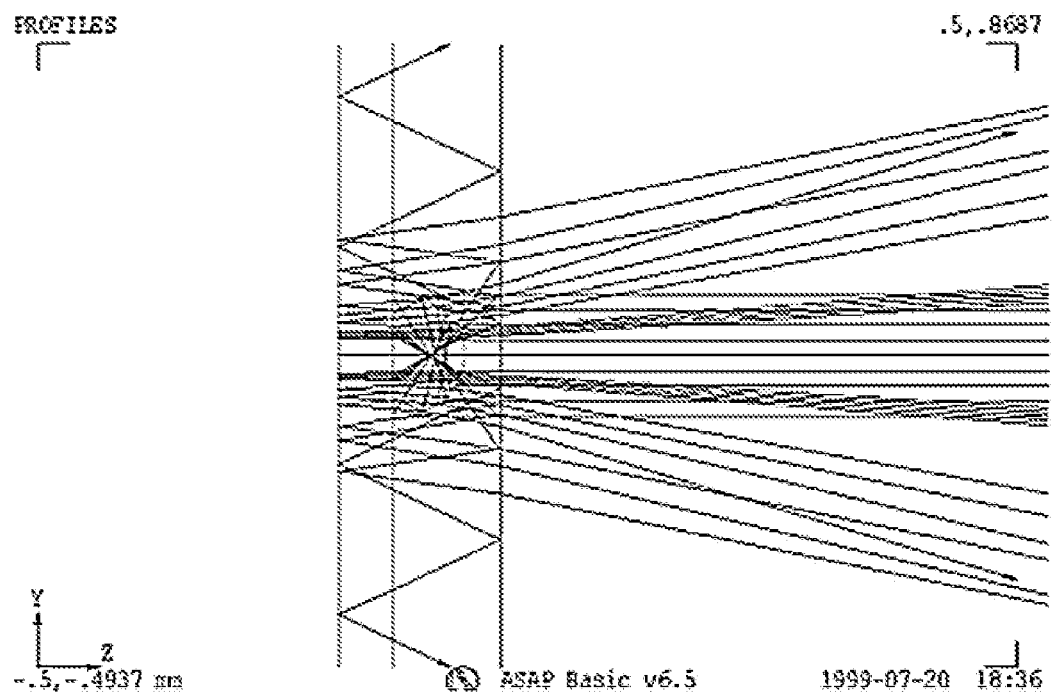
FIG. 11A and FIG. 11B show representative images illustrating the optical modeling of the beam path for BSI. Specifically.
Figure 11B:
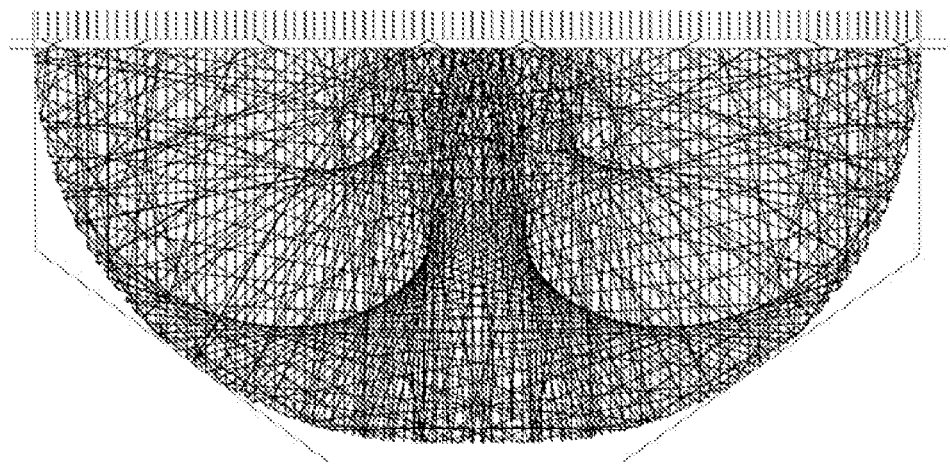
Figure 12A:
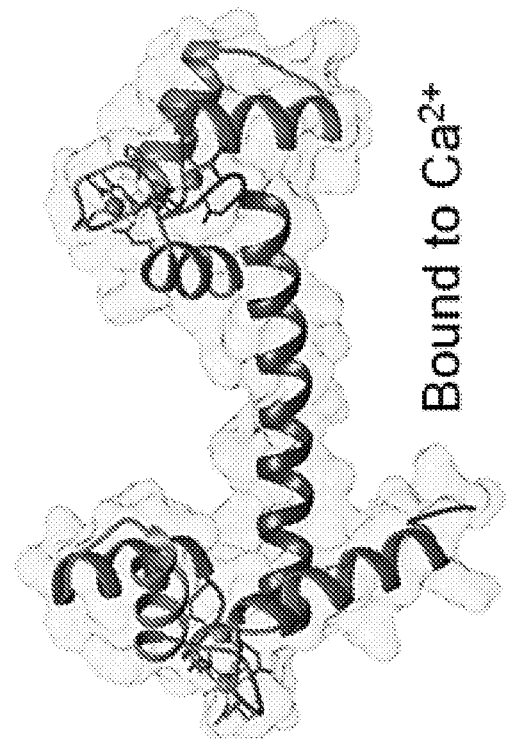
FIG. 12A-D show representative ribbon drawings for Calmodulin unbound (PDB: 1CFD) (12A), bound to Calcium (PDB: 1OSA) (12B), bound to M13 (PDB: 1CDL) (12C), and bound to TFP (PDB: 1CTR) (12D).
Figure 12B:
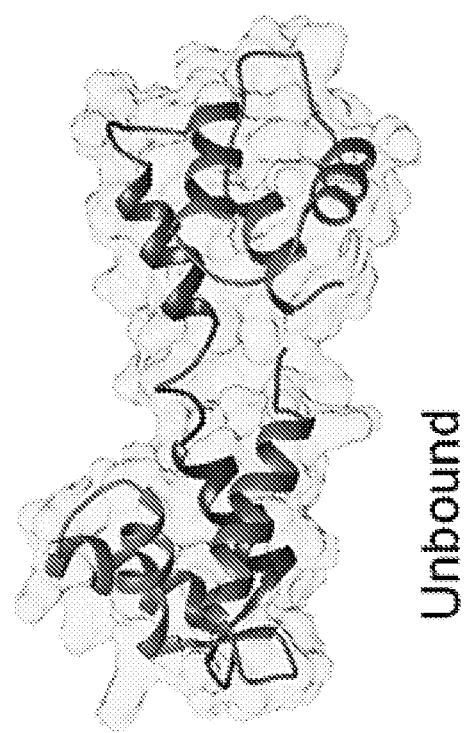
Figure 12C:
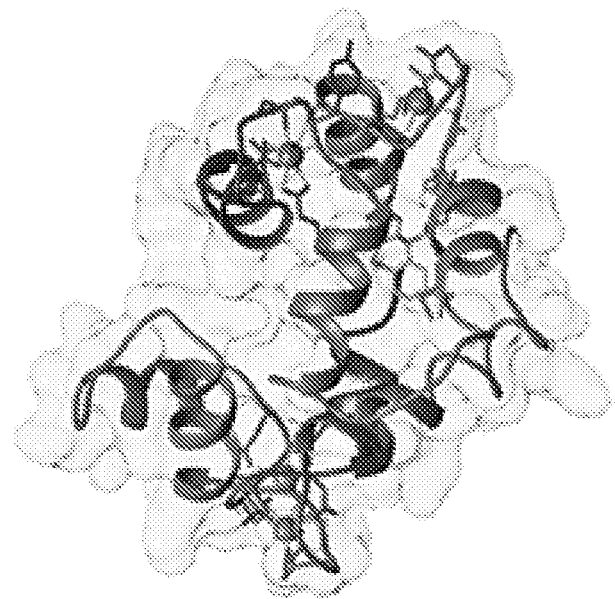
Figure 12D:
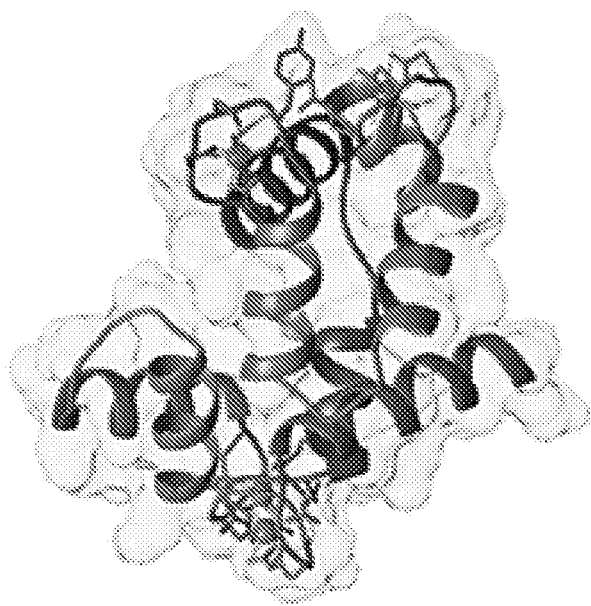

A fully physical description of BSI and quantitative analysis of fringe production is found in the literature (Sorensen, H. S. (2006) Self Calibrating Interferometric Sensing. PhD (Technical University of Denmark, Roskilde; Swinney et al. (2000) Chip-scale universal detection based on backscatter interferometry. *Anal Chem* 72(13):2690-2695; Tarigan et al. (1996) Capillary-scale refractive index detection by interferometric backscatter. *Anal Chem* 68(10): 1762-1770), yet a summary is provided here. Since fringe position (shift) reports the RI, proper selection is imperative. With reference to FIG. 9D-F, FIG. 10A, and FIG. 10B it can be easily recognized that the fringes are not equivalent in their physical origin and thus their response. BSI is a multimodal interferometer with several dominate frequencies, all mixing as a result of reflection and refraction from the surfaces of the chip. There is low frequency component emanating from the top and bottom surface reflections, a middle frequency (the one employed) principally from a combination of the rays combining after reflecting from all surfaces and traversing the channel. The other frequencies are potentially of interest, but have not been as well characterized. To illustrate the complexity of BSI, FIG. 11A and FIG. 11B presents optical ray traces of the optical train using ASAP® modeling software. FIG. 11B presents a higher resolution modeling outcome, showing, as empirical evidence suggests (Swinney et al. (2000) Chip-scale universal detection based on backscatter interferometry. *Anal Chem* 72(13):2690-2695; Tarigan et al. (1996) Capillary-scale refractive index detection by interferometric backscatter. *Anal Chem* 68(10):1762-1770), that this multimodal interferometer has an optical path-length, greater than the dimensions of the channel. Note that FIG. 11B more clearly shows that there is significant optical energy (numbers of rays) concentrated in the central part channel, predominantly interrogating the bulk solution. Others take a grazing angle path, principally reporting RI changes at the channel surface. Simply put, not all fringes emanate from the same region of the object (chip, capillary, capillary in an enclosure, etc.), and as a consequence they don't all exhibit a strong free-solution signal. There is added complexity to the system since quite a bit of signal mixing occurs, resulting in fringes that respond to both the surface and the bulk RI changes. Therefore, selection of the appropriate fringes is necessary to obtain robust free-solution signals. Since a pure frequency has yet to be identified, a desirable outcome results only from combining assay procedures (see above), with prudent alignment guided by empirical evidence.

Figure 9D:
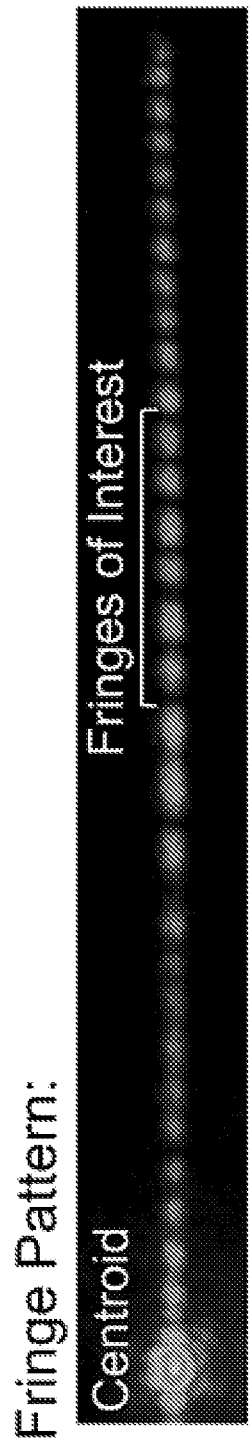
Figures 9E, 9F:
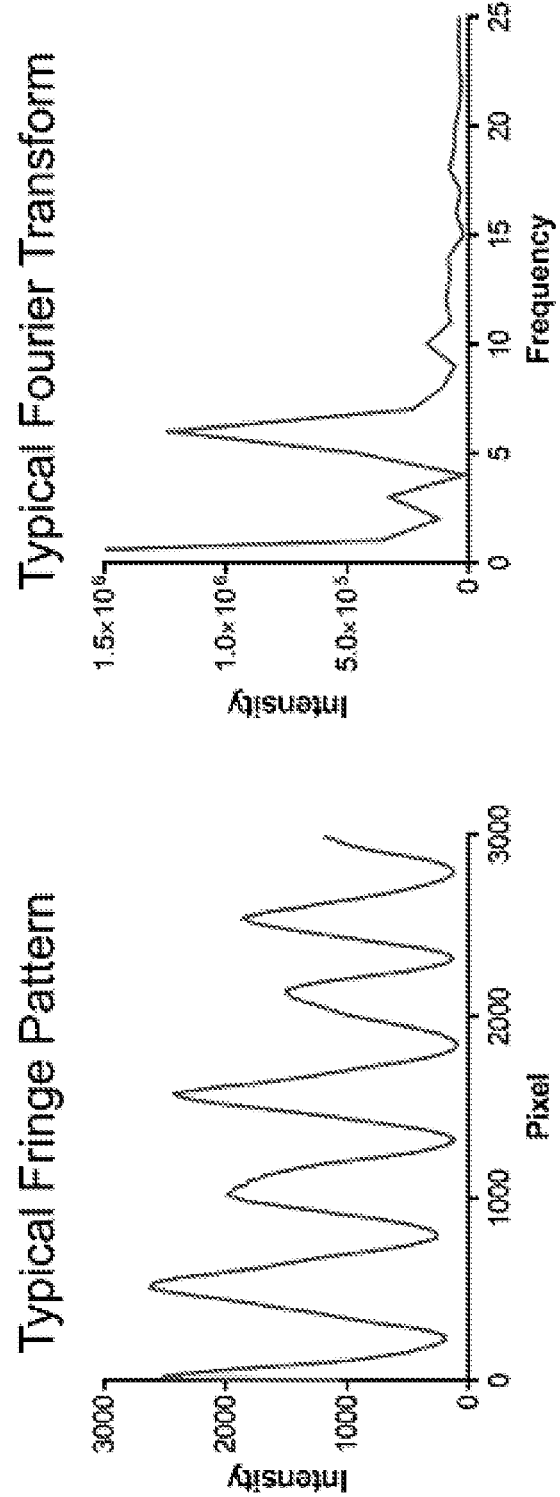

Using a chip with a 210 µm×100 µm semicircular channel isotropically etched in a 0.7 mm substrate and covered with a 1.1 mm thick top-plate produces fringes that are ca. #6-14 from the centroid that exhibit a nearly single spatial frequency (FIG. 9D-F). As described in detail previously (Markov et al. (2002) Breaking the 10(−7) barrier for RI measurements in nanoliter volumes. *Anal Chem* 74(20): 5438-5441), a Fast Fourier Transform (FFT) was performed, within a LabView program, facilitating the time dependent collection of the position of fringes in radians.

Using this same chip the probe volume was determined by calculating the volume of fluid within the intersection of the beam and the channel. The cross sectional area of channel is two quarter circles connected by a 10 µm wide rectangle (width of the etch mask) and can be calculated by:

$$A = \frac{\pi r^2}{2} + 10\,r \tag{18}$$

where r is the etch radius of the channel in µm. Here, the channels have an etch radius of 100 µm, yielding a cross sectional area of 16708 µm².

This area is then multiplied by the beam diameter (d) to determine the probe volume. Here, the beam diameter is 450 µm and results in a probe volume of 7.5 nL.

3. The BSI Signal is not Calorimetric

Under conservative conditions the reaction between IgG and $P_A$ (Bornhop et al. (2007) Free-solution, label-free molecular interactions studied by back-scattering interferometry. *Science* 317(5845):1732-1736), the Gibbs free energy, and heat energy equation were used to predict a temperature change of ~$1.09 \times 10^{-5}$ K. For 100% energy transfer to an RI change, 1 µM of the IgG-P$_A$ pair, normally analyzed at nM concentrations, would induce a $1.09 \times 10^{-9}$ RIU signal in water. This value is two orders of magnitude smaller than the BSI detection limit of $1 \times 10^{-7}$ RIU and a decade below the system noise floor of $\Delta RI = 10^{-8}$ (Bornhop et al. (2007) Materials and Methods are available as supporting material on *Science* online. *Science*). Having applied this calculation to the entirety of binding pairs within the model, the largest RI change that could be induced upon binding is no greater than the system noise, with a majority of the $\Delta RI$ values predicted being several orders of magnitude lower than the instrument LOD. Therefore, it is reasonable to infer that the heat of reaction cannot be a significant contributor to the RI signal reported in free-solution assays.

Stop-flow kinetic binding studies offered further validation that the heat of reaction is not the source of the free-solution signal (Bornhop et al. (2007) Free-solution, label-free molecular interactions studied by back-scattering interferometry. *Science* 317(5845):1732-1736), showing an absence of signal decay due to conduction to a heat sink. Environmental temperature drift can and does produce spurious signals, but this annoyance can be corrected for with careful instrument design and system temperature control. Virtually all assays performed since 2008 have been run as end-point determinations, with samples prepared, mixed, allowed to equilibrate (up to 10 hours), and then read by the interferometer. The end-point scenario excludes calorimetric contributions to the signal.

4. Conformation and Hydration Changes are the Origin of Free-Solution Signals

To quantify interactions in free-solution the experiment must be designed in a manner that places the chemical and optical focus on changes in conformation, hydrodynamic volume, hydration state, and to a lesser extent, the electronic state. Proper handling of index-matched sample and reference enable chemical focusing, while correct instrument alignment and operation maximize signal transduction by the interferometer. This methodology should also apply to systems where there is no mass change, as in protein folding, or where the difference in mass for the binding pair is large. Without wishing to be bound by theory, the relative mass of the binding partners appears to play a minor role in determining the Free-Solution Response Function (FreeSRF).

Protein folding on very small sample quantities was previously demonstrated with an early generation capillary interferometer, showing that a readout for ubiquitin folding could be obtained (Houlne et al. (1996) Refractive Index-Based calorimetric Studies of RNase T1 Unfolding in Small Volumes using Interferometric Backscatter. *Proceedings of the Society of Photo-Optical Instrumentation Engineers* 2982:159-167). In retrospect, the importance of this observation, which illustrated that in the absence of any mass change an RI sensor could be employed to follow conformation changes in free-solution, is now realized. Recent efforts to construct an assay for respiratory syncytial virus (RSV) provides additional evidence for the hypothesis that free-solution assays are reporting changes in conformation and hydration (Adams et al. (2013) The effect of hybridization-induced secondary structure alterations on RNA detection using backscattering interferometry. *Nucleic Acids Res* 41(9):e103). It was found that the BSI sensitivity was not only related to the number of unpaired nucleotides, but also to the structure of the targeted regions of the RNA sequence. For example, locked nucleic acid (LNA) probes showed a 4-fold sensitivity improvement compared to DNA probes of the same sequence. To explain this non-$d\eta/dC$ behavior, how the free-solution signal was impacted by changes in the duplex structure was investigated. Using titration and incubation of DNA:DNA duplexes with trifluroethanol (TFE), an established method for converting the duplex structure (Ivanov et al. (1974) Bbar to Abar Transition of DNA in Solution. *J Mol Biol* 87(4):817-833; Kypr et al. (2009) Circular dichroism and conformational polymorphism of DNA. *Nucleic Acids Res* 37(6):1713-1725), the transition from the B-form to A-form was induced. Next, these structural transformations were monitored with circular dichroism (CD) and ellipticity at 270 nm, showing that the BSI free-solution readout reports structural transformations in the DNA duplex (FIG. 4A and FIG. 4B). Other experiments (Pesciotta et al. (2011) Back-Scattering Interferometry: A Versatile Platform for the Study of Free-Solution versus Surface-Immobilized Hybridization. *Chemistry-an Asian Journal* 6(1):70-73) involving positional DNA mismatch binding experiments further validate this hypothesis, showing free-solution signal enhancement emanates from induced alterations to the helical geometry of the nucleic acid hybrid and not a $d\eta/dC$ change.

5. The Interferometer

The technology used to perform free-solution studies represents a unique interferometry configuration (Bornhop et al. (2007) Free-solution, label-free molecular interactions studied by back-scattering interferometry. *Science* 317 (5845):1732-1736). The optical train depicted in FIG. 9A-C is quite simple for a highly sensitive, small volume interferometer, consisting of a coherent source, an object (channel in a chip or capillary) and a transducer. Probing the object with an unfocused He—Ne beam at nearly 90° (±7° to allow fringes to be viewed), results in a high-contrast interference fringe pattern (FIG. 9D-F) in the back-scattered direction. Depending on configuration, tracking the position of the fringes enables RI changes to be quantified in the range from $10^{-4}$-$10^{-9}$ (Markov et al. (2002) Breaking the 10(−7) barrier for RI measurements in nanoliter volumes. *Anal Chem* 74(20):5438-5441; Wang and Bornhop (2005) Dual-capillary backscatter interferometry for high-sensitivity nanoliter-volume refractive index detection with density gradient compensation. *Anal Chem* 77(24):7872-7877), within picoliter-nanoliter probe volumes. A long effective path length results from multiple reflections at the fluid-channel interface and leads to the unprecedented sensitivity in constrained volumes (Swinney et al. (2000) Chip-scale universal detection based on backscatter interferometry. *Anal Chem* 72(13):2690-2695). Although many still use capillaries, the most common interferometer configuration is based on a microfluidic chip containing a nearly semicircular isotropically etched channel that is 100 µm deep and 210 µm wide. Based on empirical observations, it has been found that fringe selection is best accomplished by filling the channel with the analysis solution (buffer, serum, etc.) and counting approximately 5 fringes from the centroid, then windowing or selecting 5-7 fringes in this region that exhibit a nearly single spatial frequency (see also: Alignment and Fringe Selection). While the fringes closest to the centroid appear to exhibit a greater shift (Swinney (2000) Ultrasmall volume refractive index detection using microinterferometry. *Rev Sci Instrum* 71(7):2684-2692), a binding signal has thus far always been found in the region described above. With proper alignment, the fringe contrast ratio approaches 99% and this metric, combined with response to a change in RI (detection limits with glycerol solutions) serves to consistently produce the desired outcome. Good thermal stabilization and environmental isolation is also necessary and allows the device to produce a detection limit of $\Delta RI < 5 \times 10^{-7}$. Typically the sample/chip is probed with both planes of polarization as a result of coupling a linearly polarized laser into a non-polarization maintaining single mode fiber coupler. Misalignment will lead to slanted fringes and/or fringes with poor contrast. All of the configurations of BSI investigated exhibit a classical $d\eta/dC$ and $d\eta/dT$ response expected of an RI detector.

Without wishing to be bound by theory, a combination of factors appear to enable these free-solution measurements. instrument detection limit and 2) as recently suggested (Jepsen et al. (2015) Evaluation of back scatter interferometry, a method for detecting protein binding in solution. *Analyst* 140(3):895-901) the predicted $\Delta RI$ using $d\eta/dC$ considerations (Equation 13-17) would be undetectable.

TABLE 1

|  | Receptor | Ligand | $K_D$ (M) | BSI $\Delta RIU$ | Predicted $\Delta RIU$ Large Model | Small Model |
|---|---|---|---|---|---|---|
| Large | IL-2 Antibody | Interleukin-2 | 2.59E−11 | 8.17E−05 | 2.13E−06 | 2.23E−09 |
|  | β2AR | Alprenolol | 5.50E−10 | 1.51E−05 | 3.33E−05 | 3.54E−08 |
|  | β2AR | Isoproterenol | 1.52E−09 | 7.45E−06 | 4.25E−05 | 4.95E−08 |
|  | Basigin | Rh5 | 1.08E−06 | 2.33E−05 | 2.30E−02 | 3.46E−05 |
|  | Carbonic Anhydrase II | Acetazolamide | 1.06E−08 | 2.87E−05 | 4.50E−05 | 2.56E−08 |
|  | Carbonic Anhydrase II | Acetazolamide | 1.06E−08 | 2.87E−05 | 3.96E−05 | 3.04E−08 |
|  | Calmodulin | Calcineurin | 1.14E−08 | 4.90E−04 | 4.26E−05 | 9.66E−08 |
|  | Calmodulin | Calcineurin | 1.14E−08 | 4.90E−04 | 5.88E−05 | 1.11E−07 |
|  | Calmodulin | M13 | 9.87E−09 | 8.76E−05 | 1.52E−05 | 6.95E−08 |
|  | Thrombin | Bock | 5.96E−09 | 1.90E−05 | 9.70E−06 | 4.84E−08 |
|  | Thrombin | Tasset | 3.84E−09 | 1.45E−05 | 4.78E−06 | 3.00E−08 |
|  | Carbonic Anhydrase II | Benzene Sulfonamide | 5.68E−07 | 1.38E−05 | 9.53E−04 | 2.65E−06 |
|  | Carbonic Anhydrase II | Benzene Sulfonamide | 5.68E−07 | 1.38E−05 | 2.62E−04 | 3.24E−06 |
|  | Carbonic Anhydrase II | Sulfanilamide | 1.76E−06 | 3.92E−05 | 2.99E−03 | 8.15E−06 |
|  | Carbonic Anhydrase II | Dansylamide | 4.45E−07 | 1.72E−05 | 1.81E−03 | 1.15E−06 |
| Small | Calmodulin | TFP | 7.82E−06 | 1.56E−04 | 1.42E−02 | 5.75E−05 |
|  | Calmodulin | TFP | 7.82E−06 | 1.56E−04 | 1.85E−02 | 6.15E−05 |
|  | Calmodulin | TFP | 7.82E−06 | 1.56E−04 | 1.37E−02 | 5.72E−05 |
|  | Carbonic Anhydrase II | Sulpiride | 5.90E−06 | 3.11E−05 | 6.00E−04 | 3.55E−05 |
|  | Calmodulin | Calmodulin-Ca2+ | 1.82E−05 | 2.89E−04 | 1.10E−02 | 1.03E−04 |
|  | HIV PR | Pepstatin 1F1N | 5.30E−06 | 3.04E−05 | 2.24E−02 | 7.28E−06 |
|  | HIV PR | Pepstatin 1F1 | 1.45E−05 | 4.52E−05 | 7.18E−02 | 1.04E−05 |
|  | Concanavalin A | Mannose* | 9.63E−05 | 1.55E−05 | 4.46E−01 | 1.39E−04 |
|  | Concanavalin A | Mannose* | 9.63E−05 | 1.55E−05 | 5.21E−01 | 7.38E−05 |
|  | Concanavalin A | Glucose* | 3.44E−04 | 1.46E−05 | 2.21E+00 | 4.41E−05 |
|  | Concanavalin A | Glucose* | 3.44E−04 | 1.46E−05 | 1.97E+00 | 1.60E−04 |
|  | Recoverin | Ca$^{2+}$ | 7.35E−07 | 4.42E−05 | 2.06E−03 | 5.74E−06 |

These include: 1) the use of the proper assay methodology involving informed choice of reference and control and RI matching, 2) careful sample handling, 3) prudent instrument design with respect to temperature and pressure control, and 4) informed fringe selection as described vide infra.

If the conformation/hydration hypothesis described here has a physical basis, free-solution assays should be detectable by a device with comparable $\Delta RI$ sensitivity to those used in the SPR reports noted above. Detection limits vary for SPR, but consistently reach $\Delta RI=10^{-6}$. Here, the BSI detection limit is $\Delta RI=10^{-6}$ or 10-fold below this level (Kussrow et al. (2012) Interferometric Methods for Label-Free Molecular Interaction Studies. *Anal Chem* 84(2):779-792; Olmsted I R, et al. (2014) Toward Rapid, High-Sensitivity, Volume-Constrained Biomarker Quantification and Validation using Backscattering Interferometry. *Anal Chem* 86(15):7566-7574; Swinney et al. (2000) Chip-scale universal detection based on backscatter interferometry. *Anal Chem* 72(13):2690-2695). Therefore, using proper methodology the signal to noise ratio (S/N) of the interferometer should enable molecular interactions to be measured. As shown in FIG. 7A, 7B, and FIG. 6A-F, 1) the actual $\Delta RI$ measured by BSI for a binding event is well within the 6. The Free-Solution RI Signal for Interactions/Reactions Consider the reaction between the two species A and B. As a chemist, it is tempting to write the equation for this reaction as: A+B→A–B, but this disregards the complexity of the interaction. When A and B react they undergo electronic transitions, lose or gain hydration, and experience significant changes in the atomic geometry. So the product is just that, an entirely new species allowing the reaction to written as: A+B→C. If this is the case, then the product formed from the interaction of A and B must have a unique and different dielectric constant or molecular dipole moment. The new species therefore responds differently to the probing electromagnetic radiation, in a manner analogous to the pH-change induced 'structural' transformations in a dye molecule that lead to a significant change in absorption (color). For example, even the subtle change produced by ionizing phenol to phenolate results in quantifiably different absorbance spectra.

To aid in visualizing the free-solution transduction phenomena, the structural diversity found in calmodulin (CaM) was used (FIG. 12A-D). Binding of Ca$^{2+}$ to CaM (FIG. 12A) leads to a significant conformation and hydration change (Project et al. (2006) A molecular dynamics study of the effect of Ca2+ removal on calmodulin structure. *Biophys J* 90(11): 3842-3850), resulting in a new complex, $Ca^{2+}$-CaM (FIG. 12B) which has a considerable and quantifiably different electromagnetic cross-section (dielectric constant). Then, if the $Ca^{2+}$-CaM complex reacts with the M13 protein kinase (FIG. 12C) the subsequent complex is unique and has a quantifiably different RI due to induced structural and hydration changes (Torok K (2002) Calmodulin conformational changes in the activation of protein kinases. *Biochem Soc T* 30:55-61). Binding the small-molecule inhibitor, TFP, induces changes in atomic arrangement and hydration that leads to yet another unique chemical entity (FIG. 12D) (Vandonselaar et al. (1994) Trifluoperazine-induced conformational change in Ca(2+)-calmodulin. *Nat Struct Biol* 1(11):795-801). These graphical representations, generated from X-ray structure found in the Protein Data Bank (RSCD/PDB), for bound and unbound species pictorially illustrates that the potential magnitude of free-solution signal can be large (ca. $>10^{-4}$ RIU) under the proper conditions. Calculations of $\Delta$RI (Table 1, FIG. 7A, FIG. 7B, and FIG. 6A-F) further illustrate this point.

While FreeSRF is not proportional to the sum of the mass-weighted change in RI for the reactants (Eq 13-17 and FIG. 7A, FIG. 7B, and FIG. 6A-F), this property does not preclude non-reacting or non-interacting analytes from exhibiting an RI response. Only the proper preparation of the sample and reference, typically from the same matrix, enables the extraction of the free-solution signal by canceling out (often) very large bulk RI background signals. In other words, the determination is not made by comparing samples with huge RI differences, but nearly identical $\Delta$RI values. For example, $\eta_1=1.33131$ is not compared to $\eta_2=1.39131$, but samples with RI values of 1.391312 and 1.391318 ($\Delta RI=6\times10^{-6}$). The use of relative measurements ensures that the interaction is the predominant signal. Further, to minimize the influence of non-specific binding at the surface a base-line is established with the receptor present in the buffer or matrix under investigation and then using rinse solutions, reestablish this level before introduction of every new concentration for the assay.

a. The Free-Solution Response Function and an Expression Predicting Performance

The first attempt to formulate a model for label-free, free-solution assays was heuristic and based on the assumption that binding-induced change in hydrodynamic radius dominated the signal for CaM interactions. Preliminary calculations utilized the Protein Data Bank (RCSD/PDB) structural information to estimate the radius of gyration ($R_{gyr}$) and solvent accessible surface area (SASA) of the bound and unbound species ($\Delta R_{gyr}$ and $\Delta$SASA). A simple multivariable linear equation was obtained that relates the interferometry signal in phase, to change in $R_{gyr}$ and SASA for the CaM system ($\Delta BSI=1.0+2.6\times10^{-4}$ $\Delta SASA+0.054$ $\Delta R_{gyr}$). FIG. 5A shows the correlation between the predicted and experimental values for free-solution interaction studies of CaM binding $Ca^{2+}$, $Ca^{2+}$—CaM-TFP, $Ca^{2+}$—CaM-calcineurin, $Ca^{2+}$—CaM-M13 peptide. The surprisingly good correlation ($R^2=0.88$) between the actual and predicted signal magnitude for these binding events encouraged further investigation.

Next, the formalism was expanded and applied to a training set of binding pairs. The expression mirrors Beer's Law in its simplest form, which equates the absorbance of a species to the experimental parameters of the determination (path length and concentration) and the intrinsic property of the species (molar absorptivity). Here, the response for free-solution sensing is proposed to be expressed as:

$$\rho=\chi\beta C \quad (19)$$

where: $\rho$ is the FreeSRF measured in radians, $\chi$ is the Molar Refractometry in RIU/moles/L, $\beta$ is the instrument response function in radians/RIU, and C is the concentration in moles/L. Without wishing to be bound by theory, this simple equation demonstrates that the fringe shift (in radians) can be quantified by an interferometer or RI sensor when measuring a folding, binding, or hybridization event in free-solution (no labels) is directly proportional to: a) the magnitude of structural change (predominantly conformation and hydration) of the sample; b) the d$\theta$/dn sensitivity of the interferometer (which incorporates the optical path length); and c) the concentration of the analyte. Below, it is demonstrated that $\rho$ is not a function of the RII or the relative mass of the interacting species and that it can be estimated for a binding pair with reasonable confidence.

It should be noted that free-solution assays are predicated on the assumption that the solution is interrogated and not the surface (see below). The equation for FreeSRF states that the signal magnitude, $\rho$, is proportional to the number and type of transformations (See for example (Adams et al. (2013) The effect of hybridization-induced secondary structure alterations on RNA detection using backscattering interferometry. *Nucleic Acids Res* 41(9):e103), not just the number of bonds formed or broken. Measurement of $\rho$ is obtained as a change in RI reported by a fringe shift or estimated from $\chi$, the species concentration and instrument performance. As such, the most significant contributors to error in $\rho$ are instrument drift, run-to-run reproducibility, and the uncertainty in $\chi$.

In defining $\chi$ as the molar refractometry, it is recognized that the structural changes observed are a consequence of processes (folding, interactions, chemical reactions, biochemical transformations, etc.) that lead to changes in the analyte intrinsic properties, such as the dielectric constant, the molecular dipole moment, or other third order parameters. This premise is supported by evidence from complementary techniques including CD, ellipsometry (FIG. 4A and FIG. 4B), ITC, DLS (Sulmann et al. (2014) Conformational Changes in Calcium-Sensor Proteins under Molecular Crowding Conditions. *Chem-Eur J* 20(22):6756-6762) and NMR. Accuracy in $\chi$ is dominated by the quality of the initial training set data and the correctness of the structure prediction method and data derived from it. Several combined resources can provide quality structural data: the PDB; 2) PYMOL/MOLMOL (molecular analysis and display programs) and 3) M-FOLD for structure prediction and 4) Chimera for structural analysis.

Note that $\beta$ appears in the equation to account for path length variations, interferometer sensitivity (S/N) differences from device-to-device, lab-to-lab or even operator-to-operator. Currently d$\theta$/d$\eta$ is expressed as milliradians/RIU, but other sensible units that accurately express the instrument figures of merit can be used for $\beta$. In consideration of $\beta$, is should be recognized that signal extraction from an interferometric fringe shift is enabled by proper optical alignment, as well as careful selection and handling of references and controls. As a cautionary note, it is observed that BSI fringes do not exhibit uniform behavior with respect to free-solution sensitivity. Rather optimized optical alignment for fringes 6-13 (counted from the centroid), yields a single spatial frequency when using fast Fourier Transform (FFT) (Markov et al. (2002) Breaking the 10(−7) barrier for RI measurements in nanoliter volumes. *Anal Chem* 74(20):5438-5441) (FIG. 9D-F) that has always reported the free-solution signal.

The magnitude of FreeSRF scales with concentration, therefore the addition of more protein always increases $\rho$, but it must be recognized that C is the product concentration, the quantity of the new shape or complex. So circumstances can be imagined where increasing the amount of receptor doesn't produce a directly proportional change in ρ. For $K_D$ determinations, this can be dealt with by avoiding a scenario where a high product concentration is reached in the assay. At this juncture for $K_D$ determinations, FreeSRF is performed most often with target concentrations near the assumed affinity or at $K_D/10$. Additionally, it is noted that error in C impacts FreeSRF, contributing uncertainty to the training set employed to define χ and then used to predict ρ for a new system.

As with Beer's Law, which exhibits non-linearity for three major reasons (Skoog et al. (2014) *Fundamentals of Analytical Chemistry* (Brooks/Cole, Belmont, Calif.) 9th Ed.), refined versions of this theory are expected to take on higher order terms that could effect ρ similarly. While nonlinearities may be identified, these preliminary observations conform well to the simple expression proposed.

b. Testing the Validity of FreeSRF

As with other models (Marsh and Teichmann (2011) Relative Solvent Accessible Surface Area Predicts Protein Conformational Changes upon Binding. *Structure* 19(6): 859-867; Dickinson et al. (1996) A chemical-detecting system based on a cross-reactive optical sensor array. *Nature* 382(6593):697-700; Gharagheizi et al. (2014) Group Contribution Model for the Prediction of Refractive Indices of Organic Compounds. *J Chem Eng Data* 59(6):1930-1943; Katritzky et al. (1998) Correlation and prediction of the refractive indices of polymers by QSPR. *J Chem Inf Comp Sci* 38(6):1171-1176; Koradi et al. (1996) MOLMOL: A program for display and analysis of macromolecular structures. *J Mol Graphics* 14(1):51-55), it was necessary to use a learning set to establish the appropriate relationships and weighting parameters for FreeSRF. In this case, χ was determined from $\rho_{exp}$ for a training set of well-characterized binding systems (Table 2A and Table 2B). Multiple users performed the assays on several different interferometers (of similar configuration) to insure confidence in the result and minimize operator or device biases.

TABLE 2A.

Large Model

| Receptor | Ligand | Experimental Chi (RIU/M) | Model Chi (RIU/M) | Percent Error (%) |
| --- | --- | --- | --- | --- |
| IL-2 Antibody | Interleukin-2 | 827964 | 823965 | 0.5 |
| β2AR | Alprenolol | 591423 | 604924 | 2.3 |
| β2AR | Isoproterenol | 290953 | 278649 | 4.2 |
| Basigin | Rh5 | 215777 | 212174 | 1.7 |
| Carbonic Anhydrase II | Acetazolamide | −57291 | −42419 | 26.0 |
| Carbonic Anhydrase II | Acetazolamide | −57291 | −37288 | 34.9 |
| Calmodulin | Calcineurin | 46087 | 37389 | 18.9% |
| Calmodulin | Calcineurin | 46087 | 51594 | 11.9% |
| Calmodulin | M13 | 16458 | 15393 | 6.5% |
| Thrombin | Bock | 9409 | 16261 | 72.8 |
| Thrombin | Tasset | 7109 | 12462 | 75.3 |
| Carbonic Anhydrase II | Benzene Sulfonamide | −1379 | −16771 | 1116.4 |
| Carbonic Anhydrase II | Benzene Sulfonamide | −1379 | −4607 | 234.2 |
| Carbonic Anhydrase II | Sulfanilamide | 782 | −17018 | 2276.2 |
| Carbonic Anhydrase II | Dansylamide | −34377 | −40557 | 18.0 |

TABLE 2B

Small Model

| Receptor | Ligand | Experimental Chi (RIU/M) | Model Chi (RIU/M) | Percent Error (%) |
| --- | --- | --- | --- | --- |
| Calmodulin | TFP | 75.2 | 73.6 | 2.2 |
| Calmodulin | TFP | 75.2 | 78.7 | 4.6 |
| Calmodulin | TFP | 75.2 | 73.2 | 2.7 |
| Carbonic Anhydrase II | Sulpiride | 62.0 | 60.2 | 2.9 |
| Calmodulin | Calmodulin-$Ca^{2+}$ | 56.1 | 56.5 | 0.6 |
| HIV PR | Pepstatin 1F1N | 13.7 | 13.7 | 0.5 |
| HIV PR | Pepstatin 1F1 | 10.2 | 7.2 | 29.9 |
| Concanavalin A | Mannose | 7.8 | 14.4 | 85.4 |
| Concanavalin A | Mannose | 7.8 | 7.7 | 1.2 |
| Concanavalin A | Glucose | 2.6 | −1.3 | 149.2 |
| Concanavalin A | Glucose | 2.6 | 4.6 | 78.1 |
| Recoverin | $Ca^{2+}$ | 78.0 | 78.1 | 0.1 |

For each of the training systems the reference-corrected phase shift ($\rho_{exp}$ in milliradians) was experimentally quantified at known concentrations of ligand. These values were used to determine the FreeSRF values for the experimental conditions: $\rho_{expBmax}$, $\beta_{exp}$, and $C_{Bmax}$, which in turn facilitates the calculation of values for $\chi_{exp}$ for the training set at the final concentration of product:

$$\frac{\rho_{exp} B_{max}}{\beta * C_{Bmax}} = \chi_{exp} \quad (20)$$

Running a dη/dC calibration experiment allows β to be determined in radians/RIU for the specific instrument used in the binding assay. This experiment consists of measuring the phase shift as a function of glycerol concentration in mM (or another suitable analyte). From this linear relationship, the slope was obtained, expressed in radians/mM. For example, the response of $BSI_4$ (instrument #4 of 9) for a glycerol calibration curve was found to be 0.011 radians/mM, a typical value for this chip-based device. Then β was expressed in RIU per mM glycerol using a conversion factor from the CRC for dη/dC; in the case of glycerol this parameter is $1.04863 \times 10^{-5}$ RIU/mM (Anonymous (1996-1997) *CRC Handbook of Chemistry and Physics* (Chemical Rubber Publishing Company, Boca Raton) 77th Ed.). Thus for $BSI_4$:

$$\beta = \frac{0.015 \frac{radians}{mM}}{1.04863 \times 10^{-5} \frac{RIU}{mM}} = 1442.308 \frac{radians}{RIU} \quad (21)$$

To obtain the desired values for $\chi_{Bmax}$ the concentration of the product, [Complex], detected upon physical transformation must be known. Several approaches can be used to find this value. Here an equilibrium solver written in Excel was used to determine the [Complex] at each concentration of ligand. The solver uses the mass balance equation, the receptor concentration, ligand concentration, and $K_D$ to calculate product concentration. Then the maximal concentration of product is determined by plotting the product versus ligand concentrations and fitting the curve using a single-site binding isotherm. $B_{max}$ is equal to the maximal concentration of product that is formed under the experimental conditions with high accuracy and has less bias than results produced at lower concentrations with a reduced S/N. To check the validity of using $B_{max}$ for the [Complex] and the solver, the quadratic equation was used to solve the equilibrium mass balance equation for the concentration of the complex at each point on the saturation isotherm produced from the end-point binding assay. Results shown in Table 3 illustrate that using the solver for $B_{max}$ produces comparable values to the more computational intensive approach based on the quadratic expression.

TABLE 3

| | | $\rho_{exp}$ Experimental BSI signal (mrad) | C (M)* | $\rho_{model}$ Predicted BSI signal (mrad) | Percent Error |
|---|---|---|---|---|---|
| | Ligand Concentration (M) | | | | |
| Carbonic Anhydrase | 0.00 | 0.00 | 0.00 | 0.00 | 0.0% |
| | $3.90 \times 10^{-8}$ | −3.81 | $4.07 \times 10^{-11}$ | −2.37 | 37.8% |
| | $7.80 \times 10^{-8}$ | −4.57 | $7.52 \times 10^{-11}$ | −4.38 | 4.1% |
| | $1.56 \times 10^{-7}$ | −5.91 | $1.31 \times 10^{-10}$ | −7.62 | 29.0% |
| | $3.12 \times 10^{-7}$ | −9.68 | $2.07 \times 10^{-10}$ | −12.09 | 24.9% |
| | $6.25 \times 10^{-7}$ | −14.32 | $2.93 \times 10^{-10}$ | −17.10 | 19.4% |
| | $1.25 \times 10^{-6}$ | −17.89 | $3.70 \times 10^{-10}$ | −21.55 | 20.5% |
| | $2.50 \times 10^{-6}$ | −21.36 | $4.25 \times 10^{-10}$ | −24.78 | 16.0% |
| Recoverin | 0.00 | 0.00 | 0.00 | 0.00 | 0.00% |
| | $2.50 \times 10^{-7}$ | 9.73 | $1.90 \times 10^{-7}$ | 12.20 | 25.43% |
| | $5.00 \times 10^{-7}$ | 17.71 | $3.29 \times 10^{-7}$ | 21.12 | 19.25% |
| | $1.00 \times 10^{-6}$ | 29.39 | $4.50 \times 10^{-7}$ | 31.06 | 5.69% |
| | $2.00 \times 10^{-6}$ | 36.17 | $5.03 \times 10^{-7}$ | 37.88 | 4.75% |
| | $4.00 \times 10^{-6}$ | 40.93 | $5.23 \times 10^{-7}$ | 41.33 | 0.97% |
| | $8.00 \times 10^{-6}$ | 40.11 | $5.32 \times 10^{-7}$ | 42.97 | 7.13% |

*Solution to the mass balance equation

With $\rho_{exp}/C_{Bmax}$ and $\beta$ in hand, the experimentally determined value $\chi_{exp}$ for each of the training set species can be obtained and $\chi$ must now be determined. From experience with CaM and observations by others (see above), the hypothesis that the free-solution signal has its origin in the physical transformations upon binding or folding emerges. Therefore $\chi$ should be principally proportional to reaction/binding-induced conformation and hydration changes. Thus allowing us to propose the expression for $\chi$ to be:

$$\chi_{model} = A(\Delta SASA) + B(aveSASA) + C(\Delta R_{Gyr}) + D(aveR_{Gyr}) + E \quad (22)$$

where $\Delta SASA$ is the difference in solvent addressable surface area for bound complex and the unbound species in Å$^2$, the aveSASA is the sum of SASA values divided by the number of values (PDB structures), $\Delta R_{Gyr}$ is difference for the radius of gyration for the unbound species and that of the complex (bound species) in Å, $aveR_{Gyr}$ is sum of radius of gyration values divided by the number of values (PDB structures), and A, B, C, D, and E are fitting coefficients. The inclusion of the average quantities for Rgyr and SASA was motivated by a report by Marsh and Tiechmann (Marsh and Teichmann (2011) Relative Solvent Accessible Surface Area Predicts Protein Conformational Changes upon Binding. *Structure* 19(6):859-867) where it is demonstrated that that the absolute SASA value of a protein taken from a complex is an indicator for the amount of conformational change expected upon binding and is thus expected to affect $X_{model}$. The absolute Rgyr value is required to normalize the effects of the absolute SASA value with protein size as described by Marsh in equation 2 (Marsh and Teichmann (2011) Relative Solvent Accessible Surface Area Predicts Protein Conformational Changes upon Binding. *Structure* 19(6):859-867).

It is noteworthy that the quality and accuracy of the data-base structures used to determine the hydrodynamic properties directly impacts the predicted outcome. Here the RSCB/PDB (Table 4) was used to calculate of $R_{gyr}$ and SASA with methods described below. In some cases, the PDB files were only available for corresponding ligand/receptor pairs in varying multiples of subunits (for example, unbound calmodulin was found as a monomer, but calmodulin bound to calcineurin was found as a homodimer). In cases where appropriate, these multimers were split into monomers using Chimera (Pettersen et al. (2004) UCSF chimera—A visualization system for exploratory research and analysis. *J Comput Chem* 25(13):1605-1612).

TABLE 4

| | Receptor | Ligand | Bound PDB ID | Unbound PDB ID |
|---|---|---|---|---|
| Large | IL-2 Antibody | Interleukin-2 | 4YUE | 1M4C and 1F8T |
| | β2AR | Alprenolol | 3NYA | 2RH1 |
| | β2AR | Isoproterenol | 2Y03 | 2RH1 |
| | Basigin | Rh5 | 4U0Q | 3184 and 4WAT |
| | Carbonic Anhydrase II | Acetazolamide | 1ZSB | 1CA2 |
| | Carbonic Anhydrase II | Acetazolamide | 1YDA | 1CA2 |
| | Calmodulin | Calcineurin | 2R28 | 1OSA |
| | Calmodulin | Calcineurin | 2F2O | 1OSA |
| | Calmodulin | M13 | 1CDL | 1OSA |
| | Thrombin | Bock | 1HUT | 3U69 |
| | Thrombin | Tasset | 4I7Y | 3U69 |
| | Carbonic Anhydrase II | Benzene Sulfonamide | 4JSA | 1CA2 |
| | Carbonic Anhydrase II | Benzene Sulfonamide | 2WEJ | 1CA2 |
| | Carbonic Anhydrase II | Sulfanilamide | 2NNG | 1CA2 |
| | Carbonic Anhydrase II | Dansylamide | 1OKL | 1CA2 |
| Small | Calmodulin | TFP | 1CTR | 1OSA |
| | Calmodulin | TFP | 1LIN | 1OSA |
| | Calmodulin | TFP | 1A29 | 1OSA |
| | Carbonic Anhydrase II | Sulpiride | 1G4O | 1CA2 |
| | Calmodulin | Calmodulin-Ca2+ | 1OSA | 1CFD |
| | HIV PR | Pepstatin 1F1N | 4EJK | 5HVP |
| | HIV PR | Pepstatin 1F1 | 4EJD | 5HVP |
| | Concanavalin A | Mannose* | 5CNA | 1JBC |
| | Concanavalin A | Mannose* | 1I3H | 1JBC |
| | Concanavalin A | Glucose* | 1CJP | 1JBC |
| | Concanavalin A | Glucose* | 1GIC | 1JBC |
| | Recoverin | Ca$^{2+}$ | 1OMV | 1REC |

Numerous approaches exist to quantify $R_{gyr}$ (Grosberg and Khokhlov (1994) *Statistical Physics of Macromolecules* (American Institute of Physics, New York); Fixman, M. (1962) Radius of Gyration of Polymer Chains. II. Segment Density and Excluded Volume Effects. *The Journal of Chemical Physics* 36(12):3123-3129; Sun et al. (1980) The Coil-Globule Transition—Radius of Gyration of Polystyrene in Cyclohexane. *J Chem Phys* 73(12):5971-5975). Here, a Chimera script obtained from (http://plato.cgl.ucsf.edu/trac/chimera/wiki/Scripts) was employed, enabling the calculation of $R_{gyr}$ using the expression:

$$R_{gyr} = \sqrt{\frac{\sum_{k=1}^{N} m_k (r_k - r_{mean})^2}{\sum_k^N m_k}} \quad (23)$$

where r is the position and m is the mass of each atom in the molecule. Hydrogens were removed for this calculation for consistency across species, because the Chimera program automatically adds these when displaying a new PDB file. Non-interacting species, such as ions, solvents and accessory ligands were also removed prior to determining the $R_{gyr}$. The results for these calculations are compiled in Table 5. The values obtained from Chimera correlated well with a self-written MatLab© script using the same coordinates obtained from the PDB files.

Having obtained $\Delta R_{gy}$, $\Delta SASA$ and their average values (from PDB structure), the theoretical value for $\chi_{model}$ for each interaction can be determined. Using the experimen-

TABLE 5

|  | Receptor | Ligand | Bound Radius of Gyration (Å) | Unbound Radius of Gyration (Å) | Bound Surface Area (Å$^2$) | Unbound Surface Area (Å$^2$) |
|---|---|---|---|---|---|---|
| Large | IL-2 Antibody | Interleukin-2 | 28.11 | 38.98 | 24399.8 | 26849.7 |
|  | β2AR | Alprenolol | 28.84 | 29.21 | 22944.5 | 22633.3 |
|  | β2AR | Isoproterenol | 22.00 | 21.43 | 17028.6 | 15726.8 |
|  | Basigin | Rh5 | 29.56 | 19.19 | 25215.0 | 27363.2 |
|  | Carbonic Anhydrase II | Acetazolamide | 17.40 | 17.40 | 11420.8 | 11549.7 |
|  | Carbonic Anhydrase II | Acetazolamide | 17.35 | 17.40 | 11490.0 | 11549.7 |
|  | Calmodulin | Calcineurin | 21.68 | 22.45 | 9457.7 | 10129.7 |
|  | Calmodulin | Calcineurin | 21.43 | 22.45 | 9645.2 | 10129.7 |
|  | Calmodulin | M13 | 16.5 | 22.45 | 8965.9 | 10129.7 |
|  | Thrombin | Bock | 17.82 | 17.76 | 12849.4 | 12684.2 |
|  | Thrombin | Tasset | 17.67 | 17.76 | 12791.4 | 12684.2 |
|  | Carbonic Anhydrase II | Benzene Sulfonamide | 17.39 | 17.40 | 11775.4 | 11549.7 |
|  | Carbonic Anhydrase II | Benzene Sulfonamide | 17.53 | 17.40 | 11948.8 | 11549.7 |
|  | Carbonic Anhydrase II | Sulfanilamide | 17.41 | 17.40 | 11772.7 | 11549.7 |
|  | Carbonic Anhydrase II | Dansylamide | 17.41 | 17.40 | 11448.1 | 11549.7 |
| Small | Calmodulin | TFP | 15.78 | 22.45 | 8977.8 | 10129.7 |
|  | Calmodulin | TFP | 15.54 | 22.45 | 9046.4 | 10129.7 |
|  | Calmodulin | TFP | 15.54 | 22.45 | 8960.0 | 10129.7 |
|  | Carbonic Anhydrase II | Sulpiride | 17.61 | 17.40 | 12001.4 | 11549.7 |
|  | Calmodulin | Calmodulin-Ca2+ | 22.45 | 20.29 | 10129.7 | 10290.8 |
|  | HIV PR | Pepstatin 1F1N | 17.34 | 17.22 | 10160.4 | 9556.4 |
|  | HIV PR | Pepstatin 1F1 | 17.60 | 17.22 | 10069.7 | 9556.4 |
|  | Concanavalin A | Mannose* | 17.19 | 17.32 | 10559.5 | 10303.9 |
|  | Concanavalin A | Mannose* | 17.08 | 17.32 | 10447.5 | 10303.9 |
|  | Concanavalin A | Glucose* | 17.17 | 17.32 | 10310.7 | 10303.9 |
|  | Concanavalin A | Glucose* | 17.19 | 17.32 | 10405.4 | 10303.9 |
|  | Recoverin | Ca$^{2+}$ | 18.30 | 16.50 | 12014.0 | 10333.0 |

Chimera was also used to aid in calculation of the SASA values. As recommended, solvent excluded molecular surfaces were created with the help of the MSMS package: http://mgltools.scripps.edu/packages/MSMS/. Typically the SASA of only the main protein chain is used, with the surface area obtained using the "Surface" command in the MSMS program, which uses four different algorithms to determine surface area. Non-protein molecules were discarded (including solvents, ions, and ligand) prior to calculations, except when the ligand was also a protein undergoing its own 'significant' structural change. To calculate the solvent accessible surface area of the molecule, a "probe" (sphere of radius 1.4 Å) is "rolled" across the surface of the molecule. To begin, the first atom is selected, and the probe is placed at a distance of the radius of the atom, and then moved around the atom in the tangential direction until the probe comes into contact with the nearest neighbor atom. Then, the probe is moved along a path of equal radial distance between the two atoms until it encounters a third atom. This process is repeated to find the junctions between all atoms and their neighbors until the probe has been moved across the entire structure and the whole surface of the structure has been constructed. Table 5 presents the values for SASA for each of the learning set structures.

tally determined value for $\chi_{exp}$, obtained from $\rho_{exp}/C\beta$ and theoretical $\chi$ values for the entire training set, the coefficients A, B, C, D, and E for Eq 5 (Table 6) were determined by performing a linear regression in Matlab©. Using a wide range of $\chi$ values this simple model produced a "good" fit with a high correlation coefficient (FIG. 5B), but with a modest Spearman correlation coefficient of $\rho_s=0.853$ (a nonparametric measure of statistical dependence between variables that indicates the relationship is not random and that the correlation between the variables can be described using a monotonic function). Yet, a relatively large residual error (20249) (Table 6) and percent difference between $\chi_{exp}$ and $\chi_{model}$ enhances the possibility of poor prediction accuracy, particularly for systems with a relatively small FreeSRF (ρ).

TABLE 6

| ρ | All | Small | Large |
|---|---|---|---|
| Number of Systems | 25 | 11 | 14 |
| R$^2$ | 0.986 | 0.991 | 0.998 |
| Spearman's $\rho_S$ | 0.853 | 0.936 | 0.979 |
| Average Residuals | 20248.88 | 2.28 | 9441.28 |

TABLE 6-continued

| ρ | All | Small | Large |
|---|---|---|---|
| A $\left(\frac{RIU}{MA^2}\right)$ | 8.04 | 0.05 | 60.42 |
| B $\left(\frac{RIU}{MA^2}\right)$ | 23.63 | 0.026 | 23.66 |
| C $\left(\frac{RIU}{MA}\right)$ | −16617.55 | −16.05 | −17529.18 |
| D $\left(\frac{RIU}{MA}\right)$ | 29031.93 | 25.62 | 29830.00 |
| E $\left(\frac{RIU}{M}\right)$ | −796478.05 | −713.38 | −825460.48 |

A better fit was found by separating the binding systems into two sets, 'large' and 'small' responders, based on the size of FreeSRF ($\rho_{exp}$). Since the interferometer or refractive index sensor reports the magnitude of structural changes (not the binding species MW), some proteins will populate both sets upon interaction with different ligands. For example, CaM can be found in both training sets. Using the signal-size segregation approach produces the plots shown in FIG. 13A and FIG. 13B. These plots clearly illustrate that the relation between the $\chi_{exp}$ versus $\chi_{model}$ predicted a priori produces two excellent results, with linear correlation coefficients of $R^2=0.991$ and 0.998 and p values of $2.76\times10^{-6}$ and $3.13\times10^{-12}$ for the small and large FreeSRF models, respectively. Further evaluation of the relationship yields Spearman Rank correlation coefficients of $\rho_s=0.936$ and 0.979, respectively (Table 6). It is important to note that these results don't necessarily split into two best fit models and that there are likely some scaling factors not yet identified which could impact the quality of the fit. The model can really be split in any number of ways (2 subsets or 3, 4, 5 subsets) and provide similar results, yet a division into just large and small sets results in a relatively simple and easy-to-use model that produces a reasonably high quality result. It is also possible that as the training set expands a group of intermediate species will emerge. To the best of knowledge, there's not really a way to ascribe a physical property to E, which is the error term, disturbance term, or noise. This variable captures all other factors which influence the dependent variable $y_i$ other than the regressors $x_i$ and is dissimilar for the large/small sets because of the significant difference in error between the two models.

It is noteworthy that the training set used has a significant level of diversity, including ion-protein, protein-protein, small molecule-protein, protein-aptamer, membrane-protein targets analyzed as cell-derived vesicles, an antibody-antigen pair, and unaltered human erythrocytes (Saetear et al. (2015) Quantification of Plasmodium-host protein interactions on intact, unmodified erythrocytes by back-scattering interferometry. *Malaria J* 14). Further, the highly correlated results were obtained over a period spanning more than three years, by numerous BSI operators and on six different BSI instruments. Overall, the model provides values for the Molar Refractometry, χ, which correlate well with those derived from the binding experiment (Table 2A and Table 2B), suggesting it can be used to estimate the FreeSRF for systems where binding-induced conformation and hydration changes can be obtained with reasonable accuracy.

c. Predicting/Estimating FreeSRF

Figures 14A, 14B:
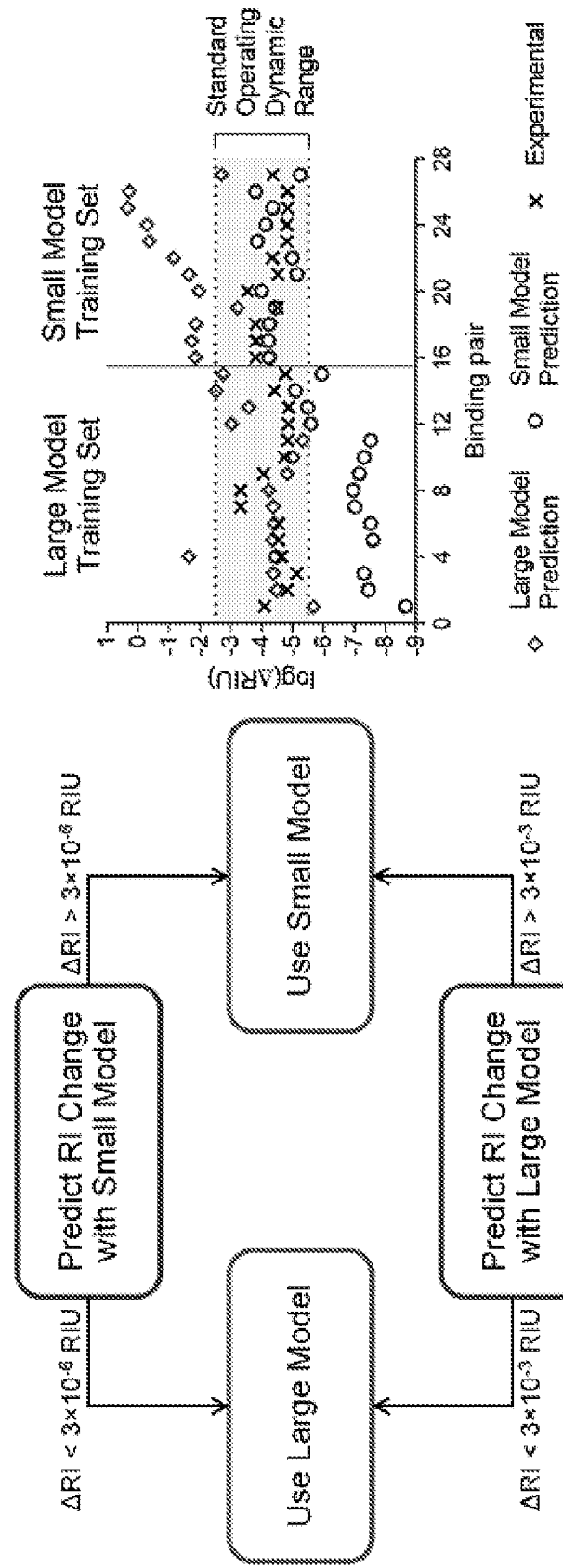
FIG. 14A and FIG. 14B show representative flow diagrams for predicting the suitable model (small or large) for a binding pair (14A) and for predicting the model for the entire learning set (14B).

There are two levels of prediction applicable to FreeSRF: one is to determine whether the small or large model should be used and the other is to estimate the free-solution signal for a molecular interaction not currently part of the training set. FIG. 14A illustrates the work flow used to estimate the applicability of using the small vs. large model. First, the structural information (PDB) and the large and small model-fitting parameters (A, B, C, D, and E) are used to calculate $\chi_{model}$. Then, since most assays are run under these conditions, the final complex concentration is estimated by setting it equal to $K_D/10$ (Table 1). Upon performing these two calculations and using the FreeSRF relationship, either a non-sense or sensible answer for the predicted change in ΔRI (e.g. detectable or not by BSI) emerges. Following the flow chart in FIG. 14A and using a conservative estimate for the operating range for the interferometer (ca. ΔRI $3\times10^{-3}$ to $3\times10^{-6}$) allows successful ranking of the binding pair with respect to large or small model. FIG. 14B illustrates that in most cases (23 of 27) or 85% of the time the prediction properly classifies the binding pair. An additional calculation using the instrument response function β enables the determination of the actual ΔRI produced for a binding pair (Table 1). Two important observations can be gleaned from this table. The first is that the experimentally measured value ρ correlates well with the predicted signal. Second, the table and FIG. 7A, FIG. 7B, and FIG. 6A-F illustrate that the magnitude of ΔRI for a binding event is relatively large.

Armed with the small vs. large selection method, the capability of the model to estimate the free-solution signal for two molecular interaction pairs not used in the training set was tested. These are $Ca^{2+}$—recoverin protein-ion interaction and the dansylamide—carbonic anhydrase (CAII) enzyme-inhibitor system. Using the PDB and Eq 22 $\chi_{model}$ was calculated for each of the two test systems. Based on ΔSASA, aveSASA, $\Delta R_{gyr}$, $aveR_{gyr}$, $\chi_{model}$ of 78.1 RIU/M and −40557 RIU/M for $Ca^{2+}$—recoverin and dansylamide—CAII, respectively, were obtained (Table 2A and Table 2B).

Figures 15A, 15B:
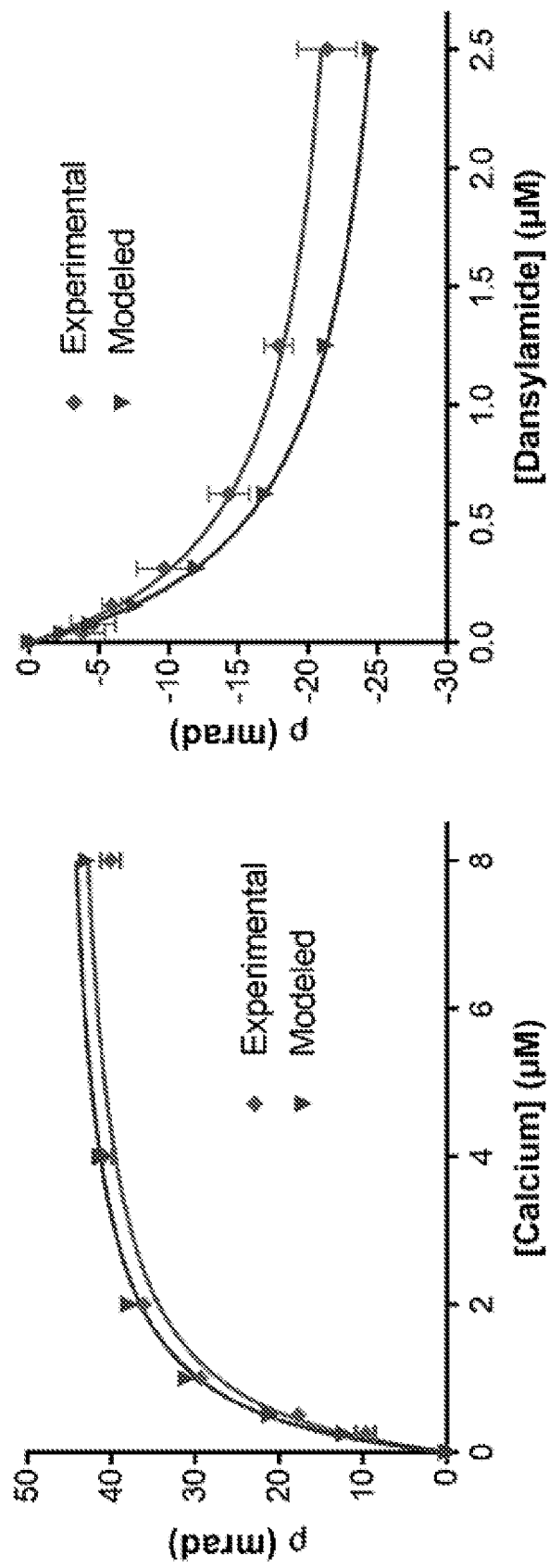
FIG. 15A and FIG. 15B show representative experimental and modeled FreeSRF binding curves for Recoverin-$Ca^{2+}$ (15A) and carbonic anhydrase II-Dansylamide (15B).

To estimate FreeSRF ($\rho_{pred}$) $\chi_{model}$ was combined with β for the instrument to be employed and the values of C determined from the $K_D$ using this solver and the concentrations to be used to generate a binding isotherm. A receptor concentration of $\sim K_D/10$ and a ligand concentration of 4-10-fold larger than $K_D$ is commonly used to reach saturation ($B_{max}$). For example, for $Ca^{2+}$—recoverin, use of the mass balance equation, a receptor concentration of $5.40\times10^{-7}$ M, and a $K_D=0.27\times10^{-6}$ M (Permyakov et al. (2000) Effects of mutations in the calcium-binding sites of recoverin on its calcium affinity: evidence for successive filling of the calcium binding sites. *Protein Eng* 13(11):783-790), allows the BSI equilibrium concentrations to be predicted (Table 3). Substitution into the FreeSRF relationship, $\rho_{pred}=\chi_{model}\beta_{exp}C$, yields Eq 24:

$$\rho_c = 78.1 \frac{RIU}{nM} \times 1055663 \frac{\text{milliradians}}{RIU} \times C(M) \qquad (24)$$

which allows the $\rho_c$ at each ligand concentration to be calculated. Plotting $\rho_{c\text{-}model}$ versus the ligand concentration gives the predicted free-solution binding assay (FIG. 15A). The same procedure was performed for the dansylamide—CAII binding pair, producing values for C and the modeled FreeSRF ($\rho_{c,model}$) (Table 3). Plotting these results gives the binding curve (triangle) displayed in FIG. 15B.

Figure 13B:
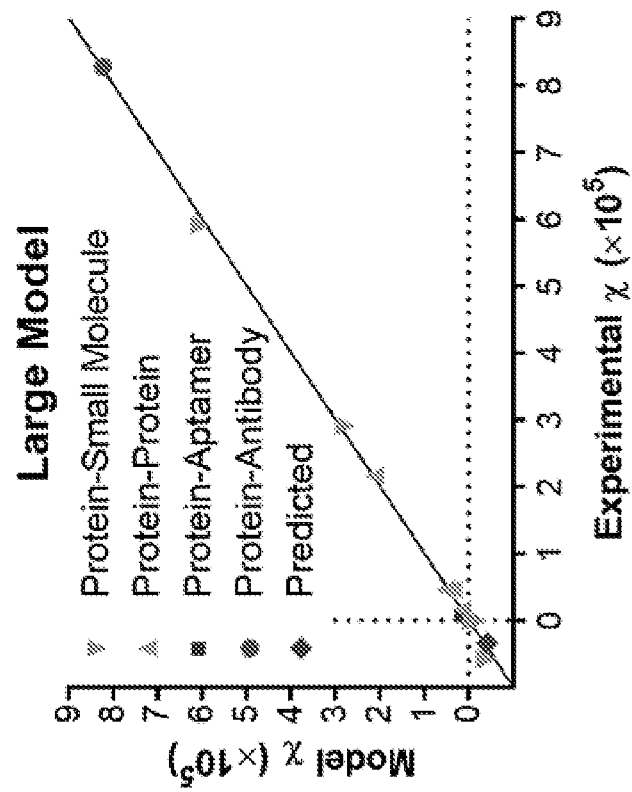
FIG. 13A and FIG. 13B show representative plots showing the correlation of $\chi_{exp}$ and $\chi_{model}$ when the learning sets are split into small (13A) and large (13B) χ values.
Figure 13A:
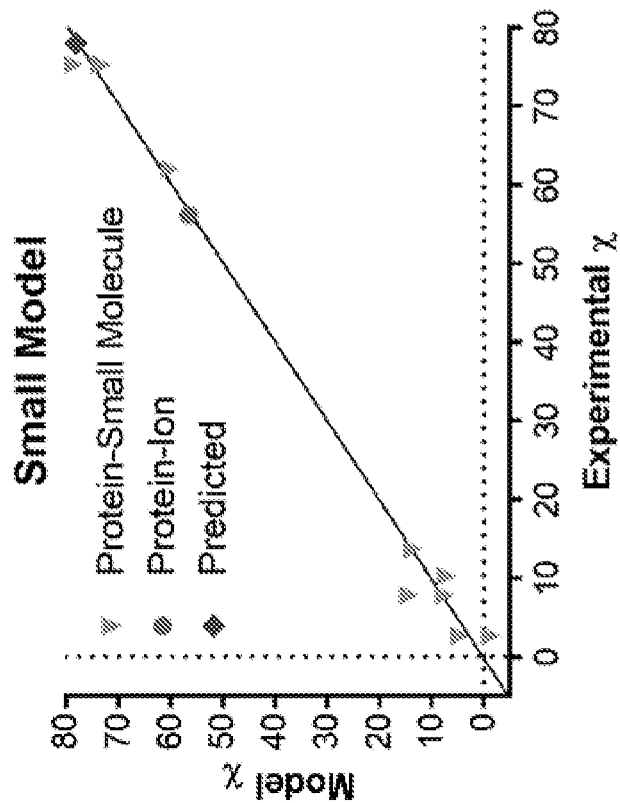

Independent of this prediction, free-solution measurements were performed with BSI to determine the $K_D$ for both the recoverin and CAII systems. The saturation isotherm binding curves for these experiments are presented as blue lines in FIG. 15A and FIG. 15B. To further illustrate the correlation between measured and estimated FreeSRF, $\chi_{exp}$ values were plotted on FIG. 13A and FIG. 13B showing where they lie on the training-set line. The percent difference from $\chi_{model}$ was 0.13% for $Ca^{2+}$—Recoverin and 18.0% for dansylamide-CAII.

Overall there is a very good correlation between the empirical and theoretical results. The relative difference between the $\rho_{exp}$ and $\rho_{model}$ was found to be less than ~29%, except for one value for one dansylamide—CAII concentration reaching 37.8% (Table 3). It is not surprising that the largest difference in $\rho$ values occurs at the lowest concentrations on the binding curve, a region of lowest instrumental S/N, which typically reports the smallest phase change. As expected for the cluster of systems that have relatively small experimental FreeSRF signals (FIG. 13A and FIG. 13B) and a larger difference in $\chi_{model}$, will lead to a comparable error in the prediction. Yet, the ability to confidently estimate the signal for a binding event within a factor of 2, given only a $K_D$ value and the structure, should enable rapid assay optimization, advancing the study of intermolecular interactions.

Even though the molecular shape and hydration changes predict the free-solution signal, it may be necessary to use additional parameters to more accurately describe the molecular dipole, dielectric constant, or electronic structure. For example, systems that undergo oxidation/reduction may produce an electronic structure redistribution that would require use of a third-order term in the equation for $\chi$. A linear model was chosen for simplicity and because it produces an excellent correlation. Yet, it is recognized that the dependence of RI from changes in structural and dynamical parameters could be more complex than the linear model fit to, in part because the fitting was done with a somewhat limited number of experimental data points. Interestingly, Marsh et al (Marsh and Teichmann (2011) Relative Solvent Accessible Surface Area Predicts Protein Conformational Changes upon Binding. *Structure* 19(6): 859-867) make a compelling argument that the absolute value of SASA correlates with the amplitude of conformational change, so ascribing the dependence of RI changes upon binding to alterations in SASA and Rgyr is quite reasonable. It is acknowledged that with additional experimental data and a better understanding of the physical basis of these transformations, a more complex model could emerge that more accurately predicts changes in RI.

Figure 16A:
FIG. 16A-D show representative data illustrating Cyfra 21-1 binding CK19 as measured via a hand-held refractometer. Specifically.

7. Molecular Interaction Determinations Using a Reichert AR200 (Hand-Held) Refractometer In this assay, molecular interactions were measured between two analytes, Cyfra21-1 and a detection antibody CK19 (also used in the ELISA kit for this target), using an inexpensive, low-sensitivity (detection limits=$10^4$ RIU), handheld refractive index detector (Reichert AR200 Model 1.8, see FIG. 16A). This experiment was designed to demonstrate that any refractive index (RI) sensor can detect molecular interactions by measuring the changes in bulk solution RI. FreeSRF model predicts that binding events produce a change in molecular dipole moment due to conformation and hydration changes when two species interact to form a new entity. The calculations and observations with backscattering interferometry (BSI) indicated that the magnitude of the binding signal was not equal to the sum of the mass-weighted RI for the interacting molecules (ions, cells, etc.) as predicted by the existing theory. The data presented clearly indicates that molecular interaction signals (manifested as changes to the bulk refractive index) can be transduced by a standard RI sensor, just as they are by BSI.

The RI detect was calibrated before the first data-recording session of each day using the procedure defined by the manufacturer. To do so, 70 µL of filtered water was injected into the sample well on the device, followed by a one minute waiting period for temperature equilibration. Then calibration function on the device was activated.

The device is set to the correct units, which in this case was Refractive Index Units in "Temperature Corrected 20° C. Mode". In this mode the device calculates (corrects for) what the RI of the solution would be when the solution is at 20° C. This setting was chosen based on the knowledge that minute changes in temperature can strongly affect RI.

Two RI sensing experiments were performed. The first was designed to evaluate the performance of the detector and to insure it was operating to the manufactures specification. The second experiment was performed to show that a simple, inexpensive, and moderate sensitivity RI detector can be used to quantify a molecular interaction/binding signal. Here BSI was used to determine the absolute RI signal expected for an interaction that had been previously characterized.

a. Device Characterization Using Glycerol as a RI Standard

Glycerol (Sigma) and DDI water was used to make a series of standards. Dilutions resulted in solutions with the final concentrations of 0, 10, 20, 30, and 40 mM.

The glycerol solutions were dispensed onto the RI detector sequentially from lowest to highest concentration, following the manufacturer's procedures, which included temperature equilibration and rinsing of the prism where the sample resides. Analysis was performed for the entire calibration set in triplicate.

Figure 16B:
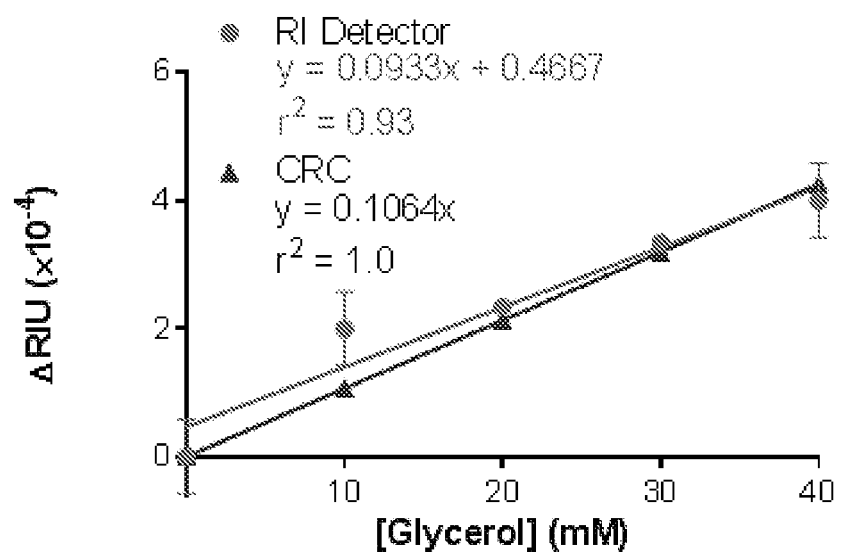

FIG. 16B illustrates the results from these experiments, showing that the Reichert detector operates at a $\Delta$RI sensitivity level of about $1 \times 10^{-4}$ RIU. As expected, the response is linear over the concentration range covered. For reference the $\Delta$RI response predicted for these concentrations of glycerol by the CRC Handbook of Chemistry and Physics was plotted. There is an excellent correlation, thus it can be confirmed that the Reichert instrument is correctly measuring $\Delta$RI values.

b. Detection of Cyfra-21-1 Spiked Buffer Solutions Using CK19 Antibody and a Hand-Held RI Sensor As with glycerol a stock solution of Cyfra was prepared. Here a stock solution concentration was made 50 ng/mL in using phosphate-buffered saline (PBS). This solution was then used to perform serial dilutions with PBS. The final Cyfra concentrations were 0, 6.25, 12.5, and 25 ng/mL. The 0 ng/mL concentration was simply a tube of PBS.

The stock solution of the (probe) antibody that binds to Cyfra, CK19, was 10 µg/mL. To prepare binding samples 12.6 µL of CK19 was combined with 240 µL of each Cyfra solution to insure that there was an excess of probe with respect to the target concentration. This dilution step led to the final Cyfra-21-1 concentrations being equal to 0, 5.94, 11.88, and 23.75 ng/mL and a final CK19 concentration of 0.5 µg/mL.

Non-binding reference samples were also prepared by combining 240 µL of each Cyfra-spiked sample with 12.6 µL of PBS.

Once all samples were combined, they were placed in a shaker for one hour to mix and reach chemical equilibrium. At this point data collection commenced by dispensing 70 µL of the first sample onto the RI sensor. This volume represented just enough solution to fully cover the prism on the device. After one minute to allow for temperature equilibration, the measurement was taken and recorded. The sample was them vacuumed out of the well. The prism was rinsed with a diluted soap solution, then rinsed with filtered water, and then dried carefully with a Kim-wipe.

The procedure involved measuring the binding sample first, followed by the reference sample, with rinsing in between each trial. This entire procedure was performed on each sample (spiked concentration), starting with the lowest concentration and ending with the highest concentration. The entire set of measurements was then repeated for three trials.

Figure 16C:
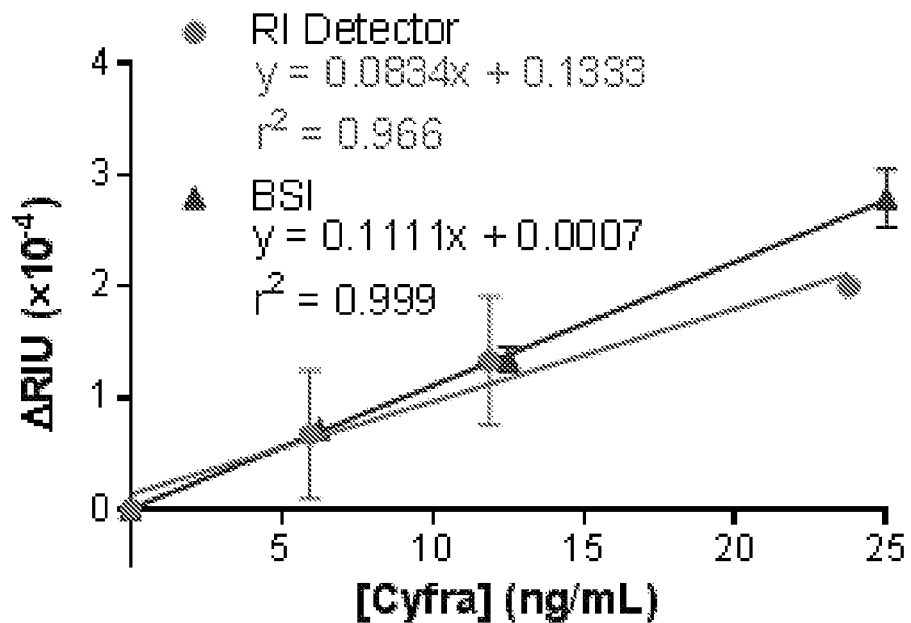

FIG. 16C displays the result for the detection of Cyfra-21-1 by RI sensing by using the label-free and free-solution binding of the antibody CK19 to the Cyfra target in buffer. It is noteworthy that the response slope of both the BSI and the Reichert RI compare favorably, as does the absolute magnitude of the ΔRI response.

Figure 16D:
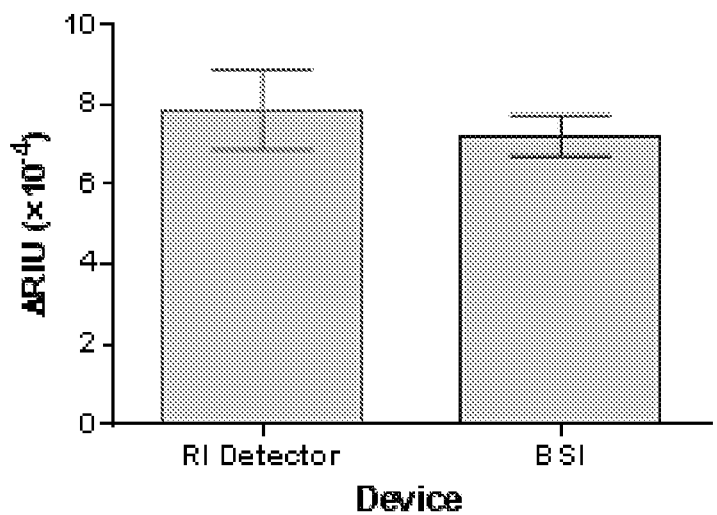
Figure 17B:
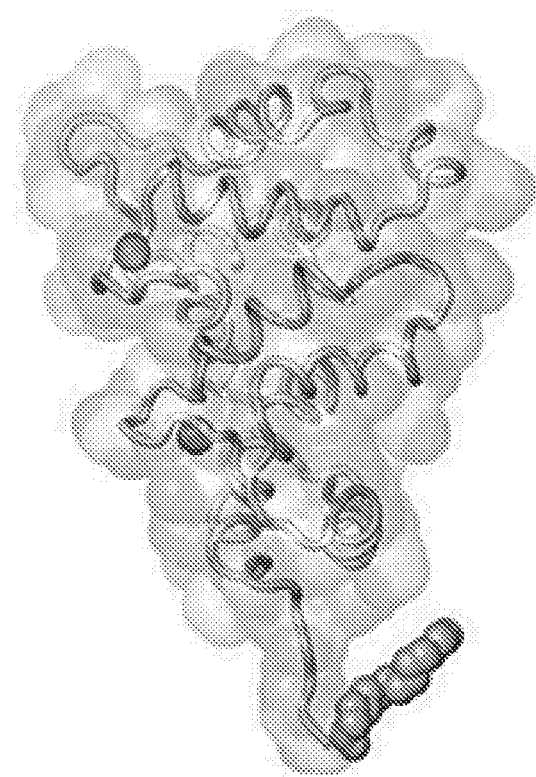
FIG. 17A and FIG. 17B show representative images of recoverin before (17A) and after (17B) $Ca^{2+}$ binding.
Figure 17A:
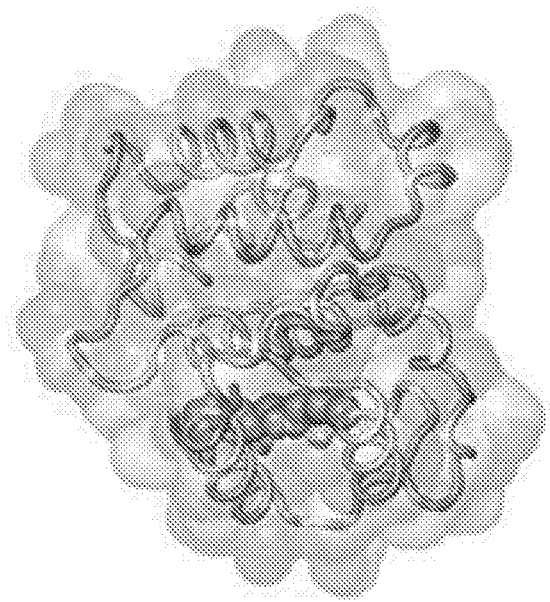

As a simple check, a second, but somewhat abbreviated experiment, was performed. In this case the signal was measured for a single sample (in triplicate) at a bit higher Cyfra-21-1 concentration (47.5 ng/mL). As shown in FIG. 16D the response for the two detection methods, interferometric RI sensing (by BSI) and standard deflection (by Reichert), is the same within experimental error. At this higher concentration of Cyfra there is an excellent correlation for the binding induced RI signal magnitude for two different sensors.

Collectively, these data clearly illustrate that the FreeSRF binding can be quantified by a standard RI sensor (even a low sensitivity hand-held device) as long as the predicted ΔRI response falls within the sensitivity limits for the instrument.

8. Molecular Interaction Determinations Using a Waters 2410 RI Detector

Figure 18A:
FIG. 18A and FIG. 18B show representative images of a RI detector (18A) and the flow path within a RI detector (18B).

In this assay, molecular interactions were measured between (1) Concanavalin A (Con A) and mannose, (2) carbonic anhydrase enzyme II (CAII) and benzene sulfonamide, and (3) CAII and acetazolamide, using a refractive index detector (Waters 2410 RI Detector, see FIG. 18A). The data presented further indicate that molecular interaction signals (manifested as changes to the bulk refractive index) can be transduced by a standard RI sensor, just as they are by BSI.

Figure 18B:
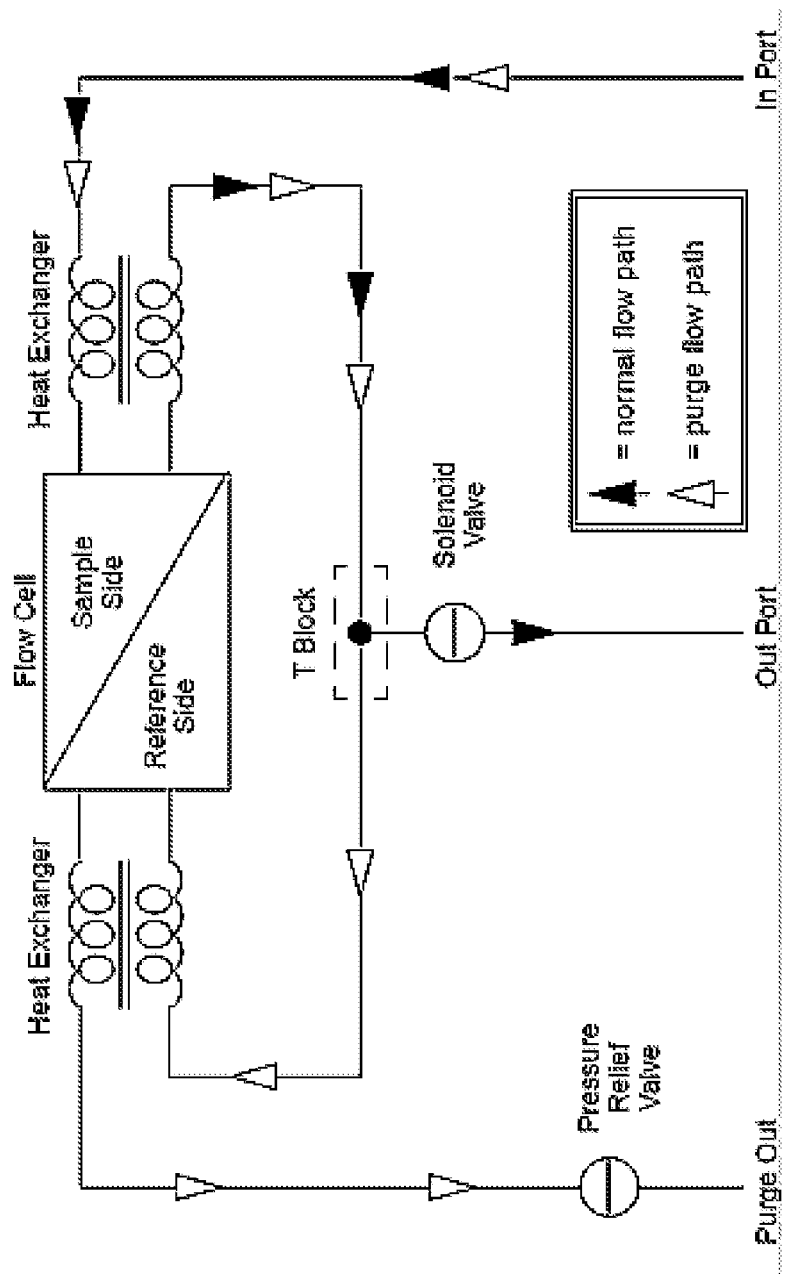

Briefly, the reference side was filled with buffer by pressing "$2^{nd}$" and the "Purge" button and then injecting the buffer (see purge flow path in FIG. 18B). Next, purging was stopped by pressing "$2^{nd}$," "Purge," and then "Enter." In order to ensure the buffer was in both reference and sample cells, "$2^{nd}$" and then the "Auto zero" button were pressed.

1 mL of reference solution was injected and the resulting signal read (the solution flows in via the inlet, through the sample side and then through the outlet tubing; see normal flow path in FIG. 18B). The flow cell was then rinsed with 3 mL buffer. The syringe was rinsed out with buffer, as well. Then, 1 mL of sample solution was injected and the resulting signal read.

1 mL of the next concentration of the reference solution was then injected and the subsequent signal read. As detailed above, the flow cell was then rinsed with 3 mL of buffer and the syringe rinsed with buffer before injecting 1 mL of the next concentration of sample solution and reading the signal. This was repeated for each concentration of reference and sample solution.

Similarly, for each trial, 1 mL of the reference solution was injected and the signal read. Both the flow cell and syringe were rinsed with buffer. Then 1 mL of the sample solution was injected and the signal read. Again, this was repeated for each concentration of reference and sample solution.

a. Device Characterization Using Glycerol as a RI Standard

Glycerol (Sigma) and DDI water was used to make a series of standards. Dilutions resulted in solutions with the final concentrations of 0, 0.5, 1.0, 3.0, and 5.0 mM.

The glycerol solutions were inject directly through the flow cell at a volume of 1 mL/injection sequentially from lowest to highest concentration, following the manufacturer's procedures, which included temperature equilibration to 35° C. Analysis was performed for the entire calibration set in triplicate.

Figure 19:
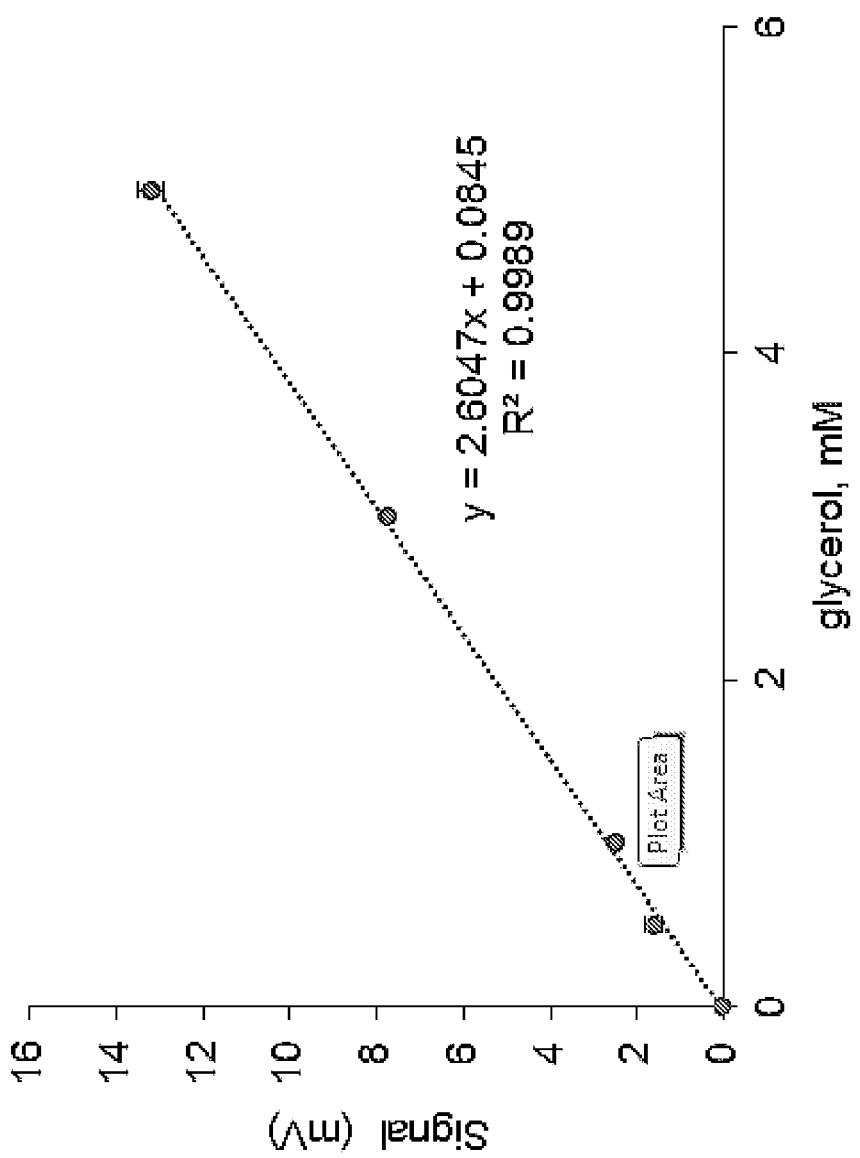
FIG. 19 shows representative data illustrating the response of a RI detector for glycerol calibration standards.

Table 9 below and FIG. 19 illustrate the results from these experiments. As expected, the response is linear over the concentration range covered.

TABLE 9

| LOQ | 0.180 | mM |
|---|---|---|
|  | $1.89 \times 10^{-6}$ | RIU |
| LOD | 0.01 | mM |
|  | $1.3 \times 10^{-7}$ | RIU | b. Detection of Mannose Spiked Buffer Solutions Using Con A and a RI Detector

A stock solution of mannose was prepared at a concentration of 1.6 mM in buffer (50 mM sodium acetate+1 mM $Ca^{2+}$+1 mM $Mn^{2+}$). This solution was then used to perform dilutions with buffer. The final mannose concentrations were 0, 100, 200, 800, and 1600 µM. The 0 µM concentration was simply a tube of buffer.

The stock solution of Con A was 8 µM. To prepare binding samples 2.5 mL of Con A were combined with 2.5 mL of each mannose solution to insure that there was an excess of probe with respect to the target concentration. This dilution step led to the final mannose concentrations being equal to 0, 50, 100, 400, and 800 µM and a final Con A concentration of 4 µM.

Non-binding reference samples were also prepared by combining 2.5 mL of each mannose-spiked sample with 2.5 mL of buffer.

Once all samples were combined, they were incubated at room temperature for 3 hr. At this point data collection commenced by directly injecting 1 mL of the sample through the flow cell. After temperature equilibration to 35° C., the measurement was taken and recorded.

The procedure involved measuring the reference sample first, followed by the binding sample, with rinsing in between each trial as detailed above. This entire procedure was performed on each sample (spiked concentration), starting with the lowest concentration and ending with the highest concentration. The entire set of measurements was then repeated for three trials.

Figure 20:
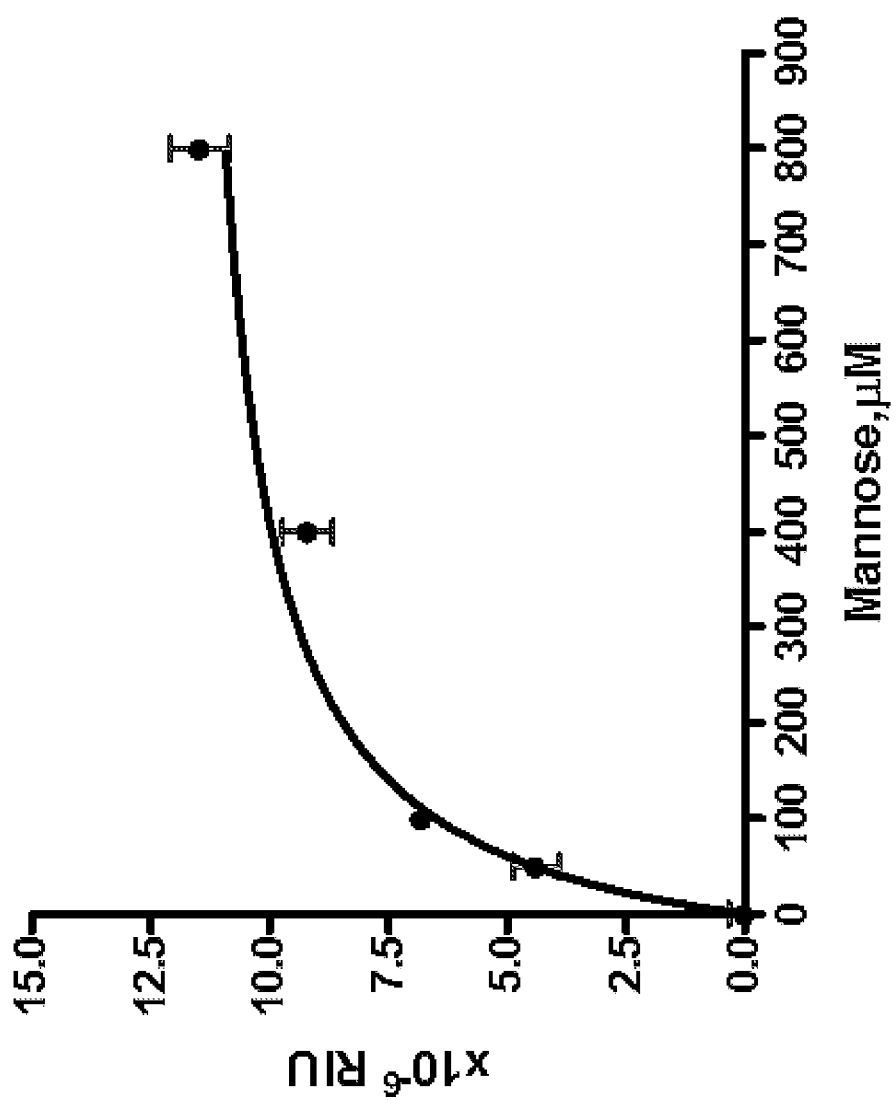
FIG. 20 shows representative data illustrating label-free, free-solution detection of mannose in buffer using a RI detector.

Table 10 and FIG. 20 displays the result for the detection of mannose by RI sensing using the label-free and free-solution binding of mannose to Con A in buffer. The results using BSI are shown for comparison.

TABLE 10

| Parameters | RI detector | BSI |
|---|---|---|
| [ConA] | 4 μM | 2 μM |
| Bmax($10^{-6}$RIU) | 12.04 ± 0.59 | 15.5 |
| Kd (μM) | 81.63 ± 14.65 | 96 |
| $R^2$ | 0.9594 | | c. Detection of Benzene Sulfonamide Spiked Buffer Solutions Using CAII and a RI Detector A stock solution of benzene sulfonamide was prepared at a concentration of 1 mM in buffer (1% DMSO+PBS). This solution was then used to perform serial dilutions with buffer. The final benzene sulfonamide concentrations were 0.625, 1.25, 2.5, 5 and 10 μM.

Two stock solutions of CAII were prepared (20 nM and 100 nM). To prepare binding samples 2.5 mL of CAII were combined with 2.5 mL of each benzene sulfonamide solution to insure that there was an excess of probe with respect to the target concentration. This dilution step led to the final benzene sulfonamide concentrations being equal to 0.3125, 0.625, 1.25, 2.5, and 5 μM and final CAII concentrations of 50 nM and 10 nM.

Non-binding reference samples were also prepared by combining 2.5 mL of each benzene sulfonamide-spiked sample with 2.5 mL of buffer.

Once all samples were combined, they were incubated in the refrigerator overnight. At this point data collection commenced by directly injecting 1 mL of the sample through the flow cell. After temperature equilibration to 35° C., the measurement was taken and recorded.

The procedure involved measuring the reference sample first, followed by the binding sample, with rinsing in between each trial as detailed above. This entire procedure was performed on each sample (spiked concentration), starting with the lowest concentration and ending with the highest concentration. The entire set of measurements was then repeated for three trials.

Figure 21A:
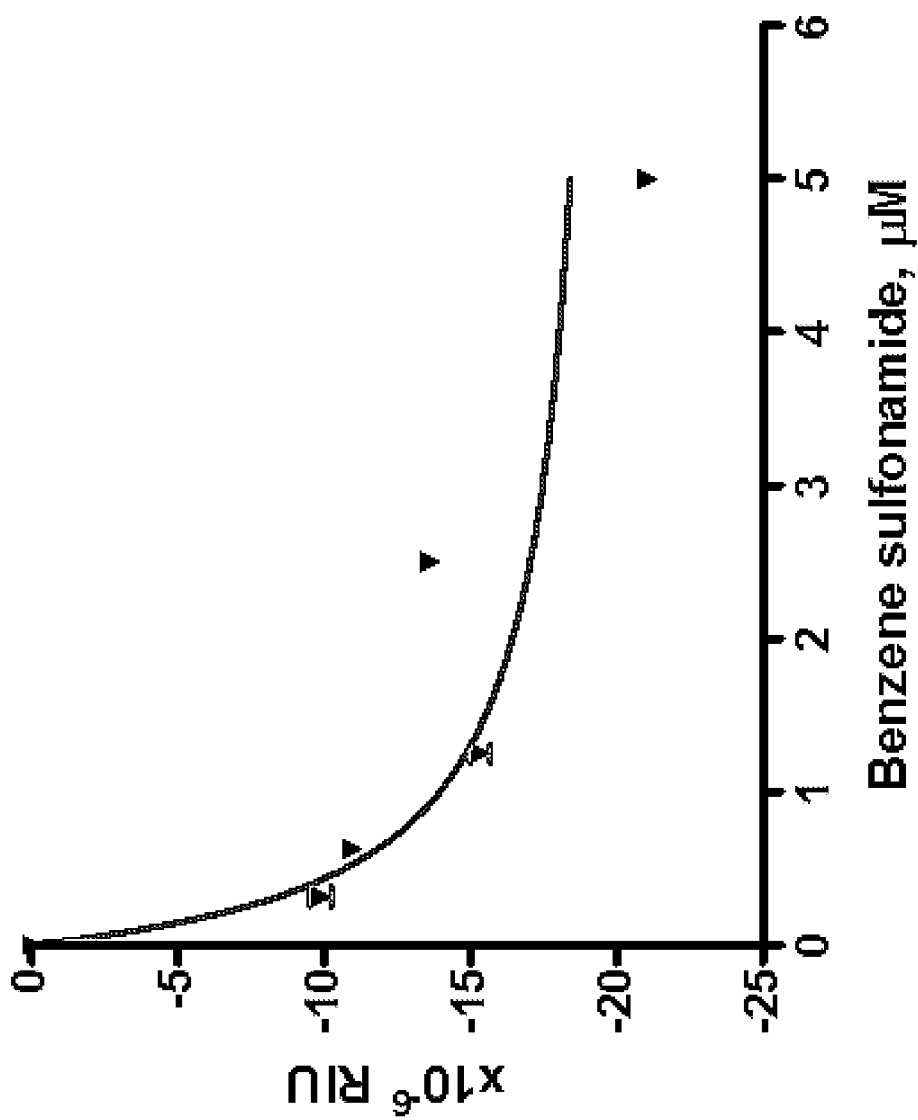
FIG. 21A and FIG. 21B show representative data illustrating label-free, free-solution detection of benzene sulfonamide in buffer binding to 50 nM CAII (21A) and 10 nM CAII (21B) using a RI detector.
Figure 21B:
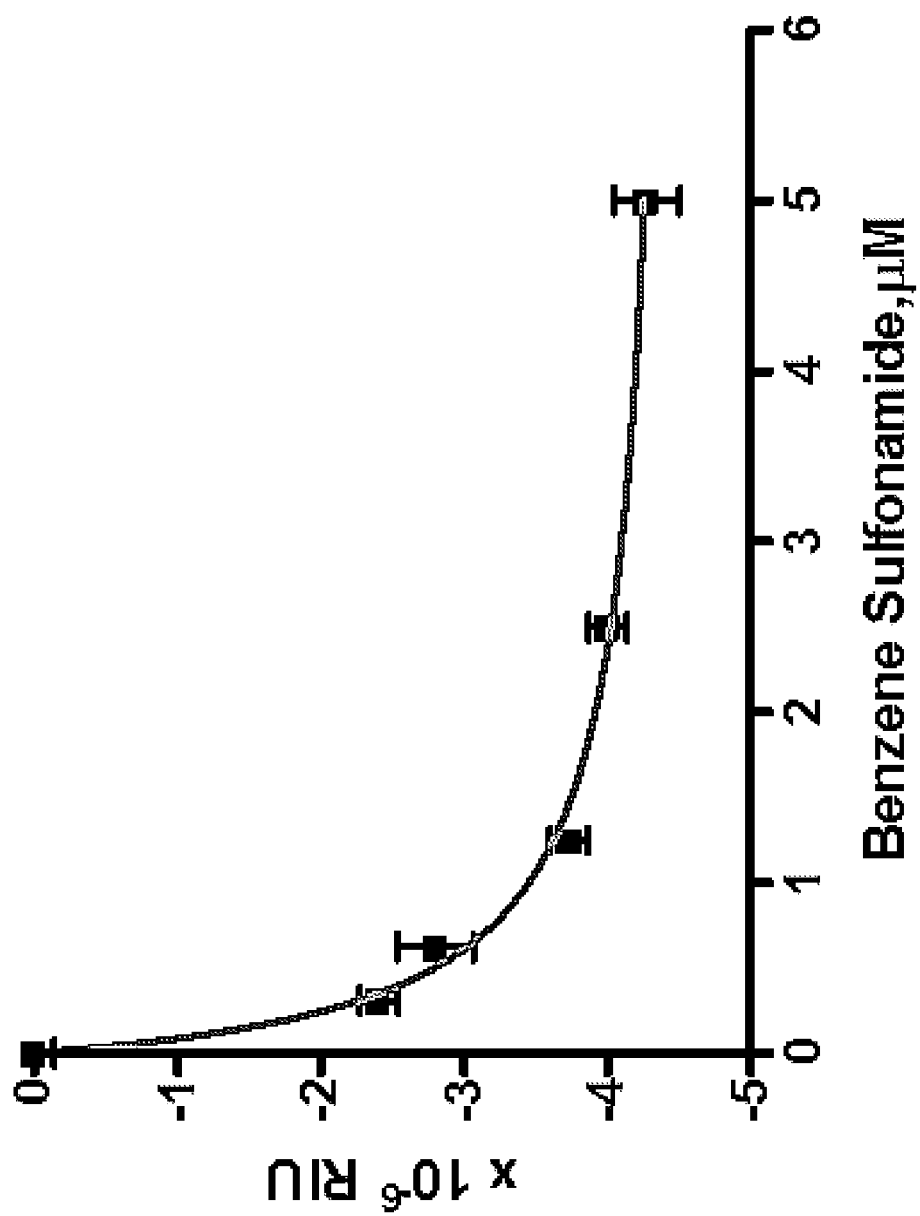

Table 11, FIG. 21A, and FIG. 21B display the results for the detection of benzene sulfonamide by RI sensing using the label-free and free-solution binding of benzene sulfonamide to CAII in buffer. The results using BSI are shown for comparison.

TABLE 11

| Parameters | RI detector | | BSI |
|---|---|---|---|
| [CAII] | 50 nM | 10 nM | 10 nM |
| Bmax($10^{-6}$RIU) | 19.98 ± 1.29 | 4.52 ± 0.165 | 13.81 |
| Kd (μM) | 0.43 ± 0.11 | 0.31 ± 0.051 | 0.57 ± 0.09 |
| $R^2$ | 0.9076 | 0.9636 | | d. Detection of Acetazolamide Spiked Buffer Solutions Using CAII and a RI Detector A stock solution of azetazolamide was prepared at a concentration of 1 mM in buffer (1% DMSO+PBS). This solution was then used to perform serial dilutions with buffer. The final azetazolamide concentrations were 0.0315, 0.0625, 0.125, 0.25, and 0.5 μM.

Two stock solutions of CAII were prepared, each at 5 nM. To prepare binding samples 2.5 mL of CAII were combined with 2.5 mL of each azetazolamide solution to insure that there was an excess of probe with respect to the target concentration. This dilution step led to the final azetazolamide concentrations being equal to 0.0078, 0.0315, 0.0625, 0.125, and 0.25 μM and final CAII concentrations of 2.5 nM each.

Non-binding reference samples were also prepared by combining 2.5 mL of each azetazolamide-spiked sample with 2.5 mL of buffer.

Once all samples were combined, they were incubated in the refrigerator overnight. At this point data collection commenced by directly injecting 1 mL of the sample through the flow cell. After temperature equilibration to 35° C., the measurement was taken and recorded.

The procedure involved measuring the reference sample first, followed by the binding sample, with rinsing in between each trial as detailed above. This entire procedure was performed on each sample (spiked concentration), starting with the lowest concentration and ending with the highest concentration. The entire set of measurements was then repeated for three trials.

Figure 22A:
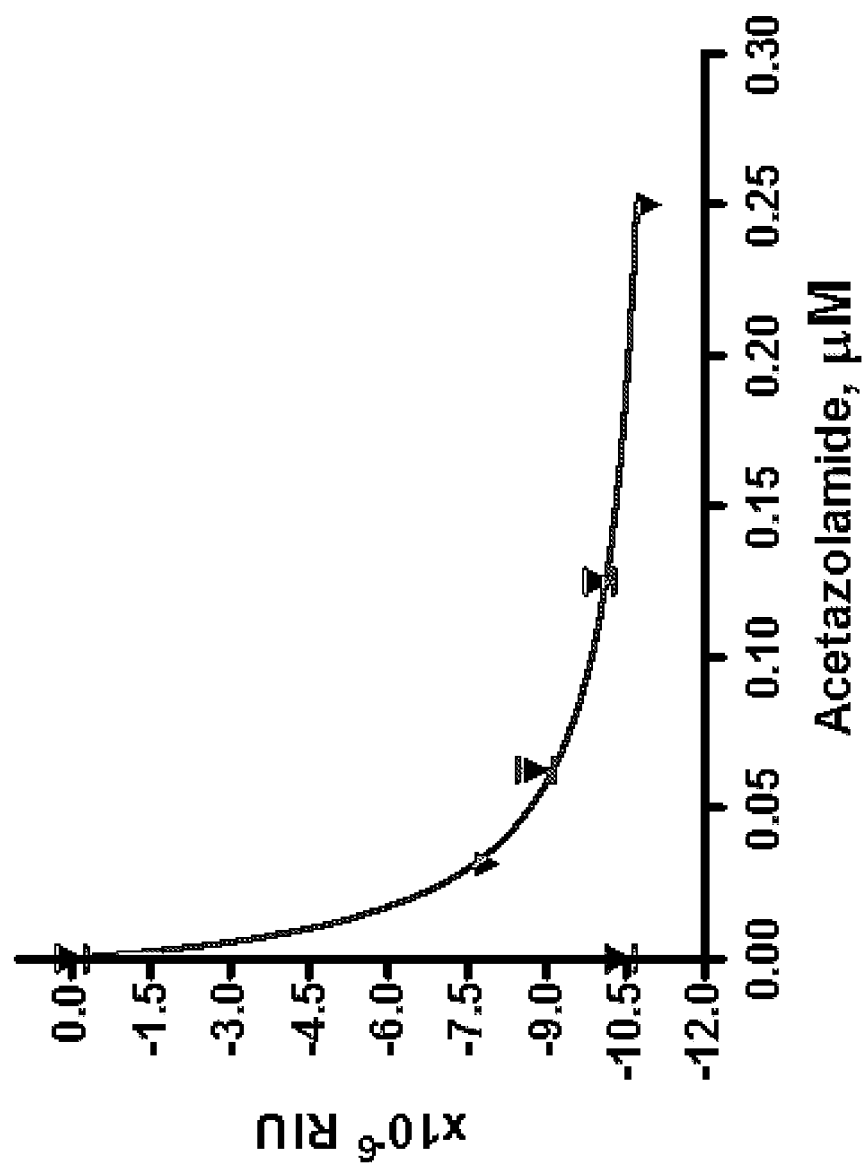
FIG. 22A and FIG. 22B show representative data illustrating label-free, free-solution detection of acetazolamide in buffer using a RI detector.
Figure 22B:
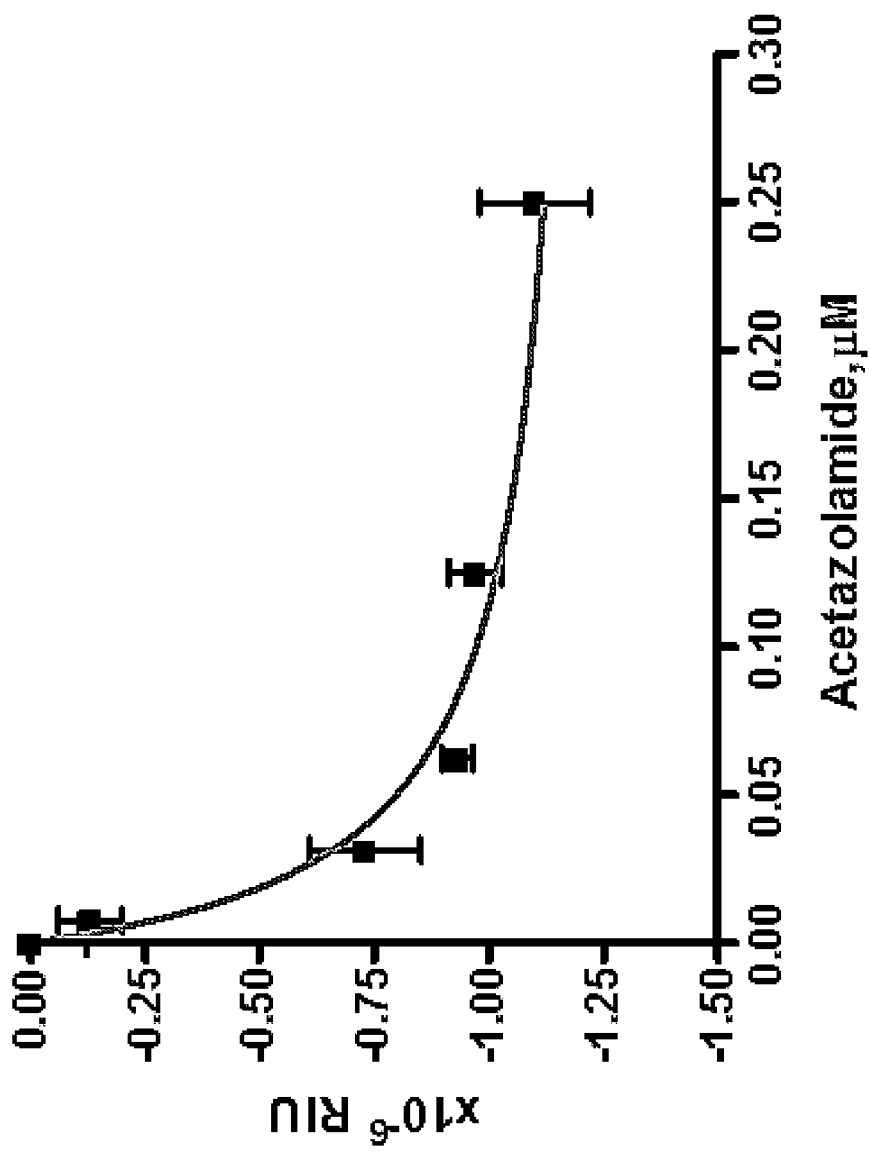

Table 12, FIG. 22A, and FIG. 22B display the results for the detection of azetazolamide by RI sensing using the label-free and free-solution binding of azetazolamide to CAII in buffer. The results using BSI are shown for comparison.

TABLE 12

| Parameters | RI detector | | BSI |
|---|---|---|---|
| [CaII] | 2.5 nM | 2.5 nM | 0.5 nM |
| Bmax($10^{-6}$RIU) | 11.36 ± 2.93 | 1.25 ± 0.12 | 28.7 |
| Kd (μM) | 0.015 ± 0.022 | 0.028 ± 0.009 | 0.011 ± 0.001 |
| $R^2$ | 0.9897 | 0.8828 | |

It will be apparent to those skilled in the art that various modifications and variations can be made in the present invention without departing from the scope or spirit of the invention. Other aspects of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A free-solution analytical method comprising detecting molecular interactions between a first non-immobilized analyte and a second non-immobilized analyte, wherein the detection is performed by refractive index sensing other than backscattering interferometry, or by circular dichroism, wherein at least one of the analytes is present in an amount of less than about $1.0 \times 10^{-6}$ M.

2. The method of claim 1, wherein the detection is performed by refractive index sensing other than forward scattering or side scattering interferometry.

3. The method of claim 1, wherein both analytes are unlabeled.

4. The method of claim 1, wherein each of the analytes is present in an amount of less than about $1.0 \times 10^{-6}$ M.

5. The method of claim 1, wherein detecting comprises one or more of:
    (a) determining an equilibrium constant, a dissociation constant, a dissociation rate, or an association rate;
    (b) calculating a change in hydrodynamic volume, entropy, or enthalpy;
    (c) determining the concentration of the first and/or second analyte;
    (d) identifying the presence of the first and/or second analyte; and
    (e) identifying the presence of a third analyte.

6. The method of claim 1, wherein refractive index sensing is via a hand-held refractive index sensing device.

7. The method of claim 1, wherein refractive index sensing is via a RI detectors based on the angle of deviation method of measurement, a RI detectors based on the Fresnel method of RI measurement, a Christiansen effect detector, an interferometer detector, or a differential refractometer detector.

8. A free-solution analytical method comprising the steps of:
(a) providing a refractive index sensor for reception of a fluid sample to be analyzed;
(b) introducing a first sample comprising a first non-immobilized analyte to be analyzed and a second sample comprising a second non-immobilized analyte to be analyzed onto the sensor, wherein the first analyte is allowed to interact with the second analyte;
(c) interrogating the fluid sample with light;
(d) detecting the light after interaction with the fluid sample, wherein the detected light is not backscattered; and
(e) detecting a molecular interaction between the first and second analyte wherein at least one of the analytes is present in an amount of less than about $1.0 \times 10^{-6}$ M.

9. The method of claim 8, wherein the sample is positioned inside a channel formed in a substrate, the channel has a longitudinal direction and a transverse direction, and the light is elongated in the longitudinal direction of the channel.

10. The method of claim 9, wherein the light is incident on at least a portion of the channel greater than 4 mm in length along the longitudinal direction.

11. The method of claim 8, wherein the light is not scattered.

12. The method of claim 8, wherein the first and/or second analyte is a complex.

13. The method of claim 8, wherein the molecular interaction is the formation of one or more covalent bonds, electrostatic bonds, hydrogen bonds, or hydrophobic interactions.

14. The method of claim 8, wherein the first and/or second analyte is one or more of an antibody, an antigen, a protein, a small molecule, a drug, a receptor, a cell, an oligonucleotide, a carbohydrate, an enzyme, a substrate, a DNA, an aptamer, a RNA, a nucleic acid, a biomolecule, a molecular imprint, a protein mimetic, an antibody derivative, a lectin, a cell membrane, an ion, a virus particle, a bacteria, and a micro-RNA.

15. The method of claim 8, wherein the molecular interaction is a binding event between one or more of antibody-antigen, protein-protein, small molecule-small molecule, small molecule-protein, drug-receptor, antibody-cell, virus-cell, virus-protein, bacteria-cell, bacteria-protein, virus-DNA, virus-RNA, bacteria-DNA, bacteria-RNA, protein-cell, oligonucleotide-cell, carbohydrate-cell, cell-cell, enzyme-substrate, protein-DNA, protein-aptamer, DNA-DNA, RNA-DNA, DNA-RNA, protein-RNA, small molecule-nucleic acid, biomolecule-molecular imprint, biomolecule-protein mimetic, biomolecule-antibody derivatives, lectin-carbohydrate, biomolecule-carbohydrate, small molecule-cell membrane, ion-protein, and protein-protein.

16. The method of claim 8, wherein the molecular interaction lacks a change in mass.

17. The method of claim 8, wherein the first and second sample are introduced simultaneously.

18. The method of claim 8, wherein the first and second sample are introduced sequentially.

19. A free-solution analytical method comprising detecting a molecular change in an analyte, wherein the detection is performed by refractive index sensing other than back-scattering interferometry, wherein detecting a molecular change comprises determining the degree of polymerization, protein folding, protein aggregation, blood oxygenation, the conformational state of an ion channel or membrane protein, or the hydration state of an ion channel or membrane protein, and wherein the analyte is present in an amount of less than about $1.0 \times 10^{-6}$.

20. The method of claim 19, wherein the detection is performed by refractive index sensing other than forward scattering or side scattering interferometry.

21. The method of claim 1, wherein at least one of the analytes is present in an amount of less than about $1.0 \times 10^{-9}$ M.

22. The method of claim 1, wherein each of the analytes is present in an amount of less than about $1.0 \times 10^{-9}$ M.

23. The method of claim 8, wherein each of the analytes is present in an amount of less than about $1.0 \times 10^{-6}$ M.

24. The method of claim 8, wherein at least one of the analytes is present in an amount of less than about $1.0 \times 10^{-9}$ M.

25. The method of claim 8, wherein each of the analytes is present in an amount of less than about $1.0 \times 10^{-9}$ M.

26. The method of claim 19, wherein the analyte is present in an amount of less than about $1.0 \times 10^{-9}$ M.

* * * * *